(12) United States Patent
Romano et al.

(10) Patent No.: US 10,124,051 B2
(45) Date of Patent: Nov. 13, 2018

(54) MENINGOCOCCUS SEROGROUP X CONJUGATE

(71) Applicant: NOVARTIS AG, Basel (CH)

(72) Inventors: Maria Rosaria Romano, Pontedera (IT); Francesca Micoli, Florence (IT); Francesco Berti, Siena (IT); Roberto Adamo, Colle di Val d'Elsa (IT); Paolo Costantino, Monteriggioni (IT)

(73) Assignee: GLAXOSMITHKLINE BIOLOGICALS SA (BE)

( * ) Notice: Subject to any disclaimer, the term of this patent is extended or adjusted under 35 U.S.C. 154(b) by 9 days.

(21) Appl. No.: 14/401,024

(22) PCT Filed: May 22, 2013

(86) PCT No.: PCT/EP2013/060447
§ 371 (c)(1),
(2) Date: Nov. 13, 2014

(87) PCT Pub. No.: WO2013/174832
PCT Pub. Date: Nov. 28, 2013

(65) Prior Publication Data
US 2015/0104479 A1    Apr. 16, 2015

Related U.S. Application Data

(60) Provisional application No. 61/650,025, filed on May 22, 2012, provisional application No. 61/698,677, filed on Sep. 9, 2012, provisional application No. 61/799,528, filed on Mar. 15, 2013.

(51) Int. Cl.
| | | |
|---|---|---|
| *A61K 39/095* | (2006.01) | |
| *A61K 45/06* | (2006.01) | |
| *G01N 30/88* | (2006.01) | |
| *A61K 47/48* | (2006.01) | |
| *A61K 39/385* | (2006.01) | |
| *A61K 47/64* | (2017.01) | |
| *A61K 39/00* | (2006.01) | |

(52) U.S. Cl.
CPC .......... *A61K 39/095* (2013.01); *A61K 39/385* (2013.01); *A61K 45/06* (2013.01); *A61K 47/4833* (2013.01); *A61K 47/48261* (2013.01); *A61K 47/646* (2017.08); *A61K 2039/6037* (2013.01); *G01N 2030/8827* (2013.01); *G01N 2030/8836* (2013.01)

(58) Field of Classification Search
CPC ................. A61K 9/014; A61K 39/095; A61K 2039/6037; A61K 47/4833; A61K 2039/627; A61K 2039/70; A61K 39/02; A61K 39/385; A61K 45/06; A61K 47/48261; C07H 15/04; C07H 1/00; C07H 1/02; C07H 3/06; C07K 14/33; C07K 14/22

USPC ......................................................... 424/400
See application file for complete search history.

(56) References Cited

U.S. PATENT DOCUMENTS

| | | |
|---|---|---|
| 4,057,685 A | 11/1977 | McIntire |
| 4,197,290 A | 4/1980 | Yoshida |
| 4,711,779 A | 12/1987 | Porro et al. |
| 5,057,540 A | 10/1991 | Kensil et al. |
| 5,306,492 A | 4/1994 | Porro |
| 5,916,588 A | 6/1999 | Popescu et al. |
| 6,090,406 A | 7/2000 | Popescu et al. |
| 6,146,902 A | 11/2000 | McMaster |
| 6,207,646 B1 | 3/2001 | Krieg et al. |
| 6,239,116 B1 | 5/2001 | Krieg et al. |
| 6,299,884 B1 | 10/2001 | Van Nest et al. |
| 6,429,199 B1 | 8/2002 | Krieg et al. |
| 6,451,325 B1 | 9/2002 | Van Nest et al. |
| 8,858,964 B2 * | 10/2014 | Vournakis ............ A61K 9/0014 424/400 |
| 9,198,928 B2 * | 12/2015 | Vournakis ............ A61K 9/0014 |

(Continued)

FOREIGN PATENT DOCUMENTS

| | | |
|---|---|---|
| CN | 103917245 A | 7/2014 |
| EP | 0109942 A2 | 5/1984 |

(Continued)

OTHER PUBLICATIONS

Bundle, DR et al, Journal of Biological Chemistry, 1974, vol. 249, pp. 4797-4801.*
Gagneux et al., Clonal groupings in serogroup X Neisseria meningitidis. Emerg Infect Dis. May 2002;8(5):462-6.
Garrido et al., Quantitative proton nuclear magnetic resonance evaluation and total assignment of the capsular polysaccharide Neisseria meningitidis serogroup X. J Pharm Biomed Anal. Nov. 2012;70:295-300.
Pajak et al., The adjuvant OM-174 induces both the migration and maturation of murine dendritic cells in vivo. Vaccine. Feb. 14, 2003;21(9-10):836-42.
Gerber et al., Human papillomavirus virus-like particles are efficient oral immunogens when coadministered with *Escherichia coli* heat-labile enterotoxin mutant R192G or CpG DNA. J Virol. May 2001;75(10):4752-60.

(Continued)

*Primary Examiner* — S. Devi
(74) *Attorney, Agent, or Firm* — Lisa Matovcik

(57) ABSTRACT

The invention provides a conjugate of a *Neisseria meningitidis* serogroup X capsular polysaccharide and a carrier molecule. The conjugate is typically made by (a) oxidizing a primary hydroxyl group in the capsular polysaccharide, to give an oxidized polysaccharide with an aldehyde group; and (b) coupling the oxidized polysaccharide to a carrier molecule via the aldehyde group, thereby giving the conjugate. The conjugate may be part of an immunogenic composition. This composition may comprise one or more further antigens, particularly capsular polysaccharides from serogroups A, W135, C and Y and conjugated forms thereof. The composition may be in an aqueous formulation. The composition is useful as a vaccine, e.g. for raising an immune response in a mammal. The invention also provides processes for making the conjugate.

11 Claims, 22 Drawing Sheets

Specification includes a Sequence Listing.

(56) References Cited

U.S. PATENT DOCUMENTS

| | | | | |
|---|---|---|---|---|
| 2013/0129789 A1* | 5/2013 | Vournakis | ............ | A61K 9/0014 424/400 |
| 2016/0047106 A1* | 2/2016 | Henderson | ............ | E02D 27/50 52/223.13 |

FOREIGN PATENT DOCUMENTS

| | | |
|---|---|---|
| EP | 0372501 A2 | 6/1990 |
| EP | 0378881 A1 | 7/1990 |
| EP | 0427347 A1 | 5/1991 |
| EP | 0471177 A2 | 2/1992 |
| EP | 0477508 A1 | 4/1992 |
| EP | 0594610 A1 | 5/1994 |
| EP | 0626169 A2 | 11/1994 |
| EP | 0689454 A1 | 1/1996 |
| EP | 0735898 A1 | 10/1996 |
| EP | 0761231 A1 | 3/1997 |
| EP | 0835318 A2 | 4/1998 |
| WO | 9314837 A1 | 12/1990 |
| WO | 9101146 A1 | 2/1991 |
| WO | 9317712 A2 | 9/1993 |
| WO | 9400153 A1 | 1/1994 |
| WO | 9403208 A1 | 2/1994 |
| WO | 9517211 A1 | 6/1995 |
| WO | 9611711 A1 | 4/1996 |
| WO | 9633739 A1 | 10/1996 |
| WO | 9640242 A1 | 12/1996 |
| WO | 9701640 A2 | 1/1997 |
| WO | 9840100 A1 | 9/1998 |
| WO | 9842375 A1 | 10/1998 |
| WO | 9842721 A1 | 10/1998 |
| WO | 9857659 A1 | 12/1998 |
| WO | 9858668 A2 | 12/1998 |
| WO | 9911241 A1 | 3/1999 |
| WO | 9927105 A2 | 6/1999 |
| WO | 9927960 A1 | 6/1999 |
| WO | 9928475 A2 | 6/1999 |
| WO | 9940936 A2 | 8/1999 |
| WO | 9942130 A1 | 8/1999 |
| WO | 9944636 A2 | 9/1999 |
| WO | 9952549 A1 | 10/1999 |
| WO | 9962923 A2 | 12/1999 |
| WO | 0007621 A2 | 2/2000 |
| WO | 0010599 A2 | 3/2000 |
| WO | 0023105 A2 | 4/2000 |
| WO | 0027994 A2 | 5/2000 |
| WO | 0037494 A2 | 6/2000 |
| WO | 0038711 A2 | 7/2000 |
| WO | 0053221 A1 | 9/2000 |
| WO | 0056360 A2 | 9/2000 |
| WO | 0056365 A1 | 9/2000 |
| WO | 0061761 A2 | 10/2000 |
| WO | 0121152 A1 | 3/2001 |
| WO | 0121207 A2 | 3/2001 |
| WO | 0172337 A1 | 10/2001 |
| WO | 0195935 A1 | 12/2001 |
| WO | 0202606 A2 | 1/2002 |
| WO | 0226757 A2 | 4/2002 |
| WO | 0234771 A2 | 5/2002 |
| WO | 02058737 A2 | 8/2002 |
| WO | 02091998 A2 | 11/2002 |
| WO | 03007985 A2 | 1/2003 |
| WO | 03009869 A1 | 2/2003 |
| WO | 03024480 A2 | 3/2003 |
| WO | 03024481 A2 | 3/2003 |
| WO | 03035836 A2 | 5/2003 |
| WO | 03093306 A2 | 11/2003 |
| WO | 2004011027 A1 | 2/2004 |
| WO | 2004018646 A2 | 3/2004 |
| WO | 2004041157 A2 | 5/2004 |
| WO | 2004060308 A2 | 7/2004 |
| WO | 2004064759 A2 | 8/2004 |
| WO | 2004092209 A2 | 10/2004 |
| WO | 2005000345 A2 | 1/2005 |
| WO | 2005/020964 * | 3/2005 | ............... A61K 9/50 |
| WO | 2005090985 A1 | 9/2005 | |
| WO | 2005114171 A2 | 12/2005 | |
| WO | 2007/084247 * | 7/2007 | ............... A61K 48/00 |
| WO | 2008061953 A1 | 5/2008 | |
| WO | 2008/102173 * | 8/2008 | ............... A61K 39/00 |
| WO | 2011/023764 * | 3/2011 | ............ A61K 39/095 |
| WO | 2011/130646 * | 10/2011 | ............... A61K 31/70 |
| WO | 2012/061400 * | 5/2012 | ............... C07K 1/18 |
| WO | 2013038375 A2 | 3/2013 | |
| WO | 2013068949 A1 | 5/2013 | |

OTHER PUBLICATIONS

Gerlich et al., Protective potential of hepatitis B virus antigens other than the S gene protein. Vaccine. Mar. 1990; 8 Suppl. 1):S63-S68.

Geysen et al., Use of peptide synthesis to probe viral antigens for epitopes to a resolution of a single amino acid. Proc Natl Acad Sci U S A. Jul. 1984;81(13):3998-4002.

Gluck et al., New technology platforms in the development of vaccines for the future. Vaccine. Dec. 20, 2002;20 Suppl 5:B10-6.

Goldblatt, Recent developments in bacterial conjugate vaccines. J Med Microbiol. Jul. 1998;47(7):563-7.

Gustafsson et al., A controlled trial of a two-component acellular, a five-component acellular, and a whole-cell pertussis vaccine. N Engl J Med. Feb. 8, 1996;334(6):349-55. Erratum in: N Engl J Med May 2, 1996;334(18):1207.

Hardy et al., Monosaccharide analysis of glycoconjugates by anion exchange chromatography with pulsed amperometric detection. Anal Biochem. Apr. 1988;170(1):54-62.

Hermanson, The Chemistry of Reactive Groups. Bioconjugate Techniques, 2nd Edition. Academic Press, London, Chapter 2, pp. 169-212 (2008).

Hopp, Retrospective: 12 years of antigenic determinant predictions, and more. Pept Res. Jul.-Aug. 1993;6(4):183-90.

Hoskins et al., Genome of the bacterium *Streptococcus pneumoniae* strain R6. J Bacteriol. Oct. 2001;183 (19):5709-17.

Hsu et al., Prospects for a hepatitis C virus vaccine. Clin Liver Dis. Nov. 1999;3(4):901-15.

Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;71 (2)176-81.

Ichiman et al., The relationship of capsular-type of *Staphylococcus epidermidis* to virulence and induction of resistance in the mouse. J Appl Bacteriol. Oct. 1981;51(2):229-41.

Ilan, Technology evaluation: naked DNA. Curr Opin Mol Ther. Feb. 1999;1(1):116-20.

Inzana, Purification and partial characterization of the capsular polymer of Haemophilus pleuropneumoniae serotype 5. Infect Immun. Jul. 1987;55(7):1573-9.

Iwarson, New approaches to hepatitis A and B vaccines. APMIS. May 1995;103(5):321-6.

Jakobsen et al., Intranasal immunization with pneumococcal conjugate vaccines with LT-K63, a nontoxic mutant of heat-Labile enterotoxin, as adjuvant rapidly induces protective immunity against lethal pneumococcal infections in neonatal mice. Infect Immun. Mar. 2002;70(3):1443-52.

Jameson et al., The antigenic index: a novel algorithm for predicting antigenic determinants. Comput Appl Biosci. Mar. 1988;4(1):181-6.

Jedrzejas, Pneumococcal virulence factors: structure and function. Microbiol Mol Biol Rev. Jun. 2001;65(2):187-207.

Johnson et al., Synthesis and biological evaluation of a new class of vaccine adjuvants: aminoalkyl glucosaminide 4-phosphates (AGPs). Bioorg Med Chem Lett. Aug. 2, 1999;9(15):2273-8.

Jones et al., Use and validation of NMR assays for the identity and O-acetyl content of capsular polysaccharides from Neisseria meningitidis used in vaccine manufacture. J Pharm Biomed Anal. Nov. 7, 2002;30(4)1233-47.

Niikura et al., Chimeric recombinant hepatitis E virus-like particles as an oral vaccine vehicle presenting foreign epitopes. Virology. Feb. 15, 2002;293(2):273-80.

(56) References Cited

OTHER PUBLICATIONS

Jones, Resiquimod 3M. Curr Opin Investig Drugs. Feb. 2003;4(2):214-8.
Kalman et al., Comparative genomes of Chlamydia pneumoniae and C. trachomatis. Nat Genet. Apr. 1999;21(4):385-9.
Kandimalla et al., Divergent synthetic nucleotide motif recognition pattern: design and development of potent immunomodulatory oligodeoxyribonucleotide agents with distinct cytokine induction profiles. Nucleic Acids Res. May 1, 2003;31(9):2393-400.
Kandimalla et al., Secondary structures in CpG oligonucleotides affect immunostimulatory activity. Biochem Biophys Res Commun. Jul. 11, 2003;306(4):948-53.
Kandimalla et al., Toll-like receptor 9: modulation of recognition and cytokine induction by novel synthetic CpG DNAs. Biochem Soc Trans. Jun. 2003;31(Pt 3):654-8.
Kato et al., Oxidation process of water-soluble starch in TEMPO-mediated system. Carbohydrate Polymers. Jan. 2003; 51(1):69-75.
Kiang et al., Simultaneous determination of glucosamine and glucosamine 4-phosphate in Lipid A with high-performance anion-exchange chromatography (HPAEC). Carbohydr Res. Nov. 1998;312(1-2):73-6.
Micoli et al., Production of a conjugate vaccine for Salmonella enterica serovar Typhi from Citrobacter Vi. Vaccine. Jan. 20, 2012;30(5):853-61.
Krieg, CpG motifs: the active ingredient in bacterial extracts? Nat Med. Jul. 2003;9(7):831-5.
Krieg, From A to Z on CpG. Trends Immunol. Feb. 2002;23(2):64-5.
Kuo et al., Characterization of a recombinant pneumolysin and its use as a protein carrier for pneumococcal type 18C conjugate vaccines. Infect Immun. Jul. 1995;63(7):2706-13.
Lei et al., Quantification of free polysaccharide in meningococcal polysaccharide-diphtheria toxoid conjugate vaccines. Dev Biol (Basel). 2000;103:259-64.
Lemercinier et al., Full 1H NMR assignment and detailed O-acetylation patterns of capsular polysaccharides from Neisseria meningitidis used in vaccine production. Carbohydr Res. Dec. 24, 1996;296:83-96.
Lenz et al., Papillomavirus-like particles induce acute activation of dendritic cells. J Immunol. May 1, 2001;166 (9):5346-55.
Lieberman et al., Safety and immunogenicity of a serogroups A/C Neisseria meningitidis oligosaccharide-protein conjugate vaccine in young children. A randomized controlled trial. JAMA. May 15, 1996;275(19):1499-503.
Lindberg, Glycoprotein conjugate vaccines. Vaccine. Oct. 1, 1999;17 Suppl 2:S28-36.
Maksyutov et al., ADEPT: a computer program for prediction of protein antigenic determinants. Comput Appl Biosci. Jun. 1993;9(3):291-7.
McCluskie et al., Parenteral and mucosal prime-boost immunization strategies in mice with hepatitis B surface antigen and CpG DNA. FEMS Immunol Med Microbiol. Feb. 18, 2002;32(3)179-85.
McMichael, Vaccines for Moraxella catarrhalis. Vaccine. Dec. 8, 2000;19 Suppl 1:S101-7.
Meister et al., Two novel T cell epitope prediction algorithms based on MHC-binding motifs; comparison of predicted and published epitopes from *Mycobacterium tuberculosis* and HIV protein sequences. Vaccine. Apr. 1995;13(6):581-91.
Meraldi et al., OM-174, a new adjuvant with a potential for human use, induces a protective response when administered with the synthetic C-terminal fragment 242-310 from the circumsporozoite protein of Plasmodium berghei. Vaccine. Jun. 2, 2003;21(19-20):2485-91.
Michon et al., Multivalent pneumococcal capsular polysaccharide conjugate vaccines employing genetically detoxified pneumolysin as a carrier protein. Vaccine. Nov. 1998;16(18):1732-41.
Angelin et al., Direct, Mild, and Selective Synthesis of Unprotected Dialdo-Glycosides. Eur J Org Chem. 2006; 4323-4326; DOI: 10.1002/ejoc.200600288.

Apostolopoulos et al., The evolution of DNA vaccines. Curr Opin Mol Ther. Aug. 2000;2(4):441-7.
Armand et al., Tetravalent meningococcal polysaccharide vaccine groups A, C, Y, W 135: clinical and serological evaluation. J Biol Stand. Oct. 1982;10(4):335-9.
Baraldo et al., N19 polyepitope as a carrier for enhanced immunogenicity and protective efficacy of meningococcal conjugate vaccines. Infect Immun. Aug. 2004;72(8):4884-7.
Baudner et al., Enhancement of protective efficacy following intranasal immunization with vaccine plus a nontoxic LTK63 mutant delivered with nanoparticles. Infect Immun. Sep. 2002;70(9):4785-90.
Beignon et al., The LTR72 mutant of heat-labile enterotoxin of *Escherichia coli* enhances the ability of peptide antigens to elicit CD4(+) T cells and secrete gamma interferon after coapplication onto bare skin. Infect Immun. Jun. 2002;70(6):3012-9.
Bell, Hepatitis A vaccine. Pediatr Infect Dis J. Dec. 2000;19(12):1187-8.
Bera et al., Design and synthesis of unnatural heparosan and chondroitin building blocks. J Org Chem. May 6, 2011;76(9):3181-93.
Bergquist et al., Antibody responses in serum and lung to intranasal immunization with Haemophilus influenzae type b polysaccharide conjugated to cholera toxin B subunit and tetanus toxoid. APMIS. Aug. 1998;106(8):800-6.
Berti et al., Relative stability of meningococcal serogroup A and X polysaccharides. Vaccine. Oct. 5, 2012;30(45):6409-15.
Bhagat et al., CpG penta- and hexadeoxyribonucleotides as potent immunomodulatory agents. Biochem Biophys Res Commun. Jan. 24, 2003;300(4):853-61.
Blackwell et al., CpG-A-induced monocyte IFN-gamma-inducible protein-10 production is regulated by plasmacytoid dendritic cell-derived IFN-alpha. J Immunol. Apr. 15, 2003;170(8):4061-8.
Brusic et al., Prediction of MHC class II-binding peptides using an evolutionary algorithm and artificial neural network. Bioinformatics. 1998;14(2):121-30.
Bundle et al., Determination of the structure and conformation of bacterial polysaccharides by carbon 13 nuclear magnetic resonance. Studies on the group-specific antigens of Neisseria meningitidis serogroups A and X. J Biol Chem. Apr. 10, 1974;249(7):2275-81.
Bundle et al., The synthesis of 2-acetamido-2-deoxy-alpha-D-glucopyranose 4-phosphate. Can J Biochem. Sep. 1974;52(9):723-5.
Buttery et al., Designing meningitis vaccines. J R Coll Physicians Lond. Mar.-Apr. 2000;34(2):163-8.
Cadoz et al., Tetravalent (A, C, Y, W 135) meningococcal vaccine in children: immunogenicity and safety. Vaccine. Sep. 1985;3(3):340-2.
Campbell et al., Safety, reactogenicity, and immunogenicity of a tetravalent meningococcal polysaccharide-diphtheria toxoid conjugate vaccine given to healthy adults. J Infect Dis. Dec. 15, 2002;186(12):1848-51.
Carter, Epitope mapping of a protein using the Geysen (PEPSCAN) procedure. Methods Mol Biol. 1994;36:207-23.
CDC: Center for Disease Control, Control and prevention of meningococcal disease: recommendations of the Advisory Committee on Immunization Practices (ACIP). MMWR Recomm Rep., retrieved online at: https://www.cdc.gov/mmwr/preview/mmwrhtml/00046263.htm Feb. 14, 1997;46(RR-5):1-10.
CDC: Center for Disease Control, Notice to Readers Availability of New Rabies Vaccine for Human Use. MMWR Weekly. Jan. 1998; 47(1):12, 19. retrieved online at: https://www.cdc.gov/mmwr/preview/mmwrhtml/00050848.htm.
Chen et al., A first meningococcal meningitis case caused by serogroup X Neisseria meningitidis strains in China. Chin Med J (Engl). Apr. 5, 2008;121(7):664-6.
Chen et al., Microdetermination of Phosphorus, Anal Chem, 1956. 28(11):1756-1758.
Constantino et al. Development and phase 1 clinical testing of a conjugate vaccine against meningococcus A and C. Vaccine. 1992;10(10):691-8.
Constantino et al., Size fractionation of bacterial capsular polysaccharides for their use in conjugate vaccines. Vaccine. Mar. 5, 1999;17(9-10)1251-63.

(56) References Cited

OTHER PUBLICATIONS

Constantino et al., The design of semi-synthetic and synthetic glycoconjugate vaccines. Expert Opin Drug Discov. Oct. 2011;6(10):1045-66.
Cox et al., ISCOMs and other saponin based adjuvants. Adv Drug Deliv Rev. Jul. 6, 1998;32(3):247-271.
Dale, Group A streptococcal vaccines. Infect Dis Clin North Am. Mar. 1999;13(1):227-43.
Davenport et al., An empirical method for the prediction of T-cell epitopes. Immunogenetics. 1995;42(5):392-7.
Davis, DNA vaccines for prophylactic or therapeutic immunization against hepatitis B virus. Mt Sinai J Med. Mar. 1999;66(2):84-90.
De Lalla et al., Cutting edge: identification of novel T cell epitopes in Lol p5a by computational prediction. J Immunol. Aug. 15, 1999;163(4):1725-9.
Debenham et al., TCP- and Phthalimide-Protected n-Pentenyl Glucosaminide Precursors for the Synthesis of Nodulation Factors as Illustrated by the Total Synthesis of NodRf-III (C18:1, MeFuc). J Org Chem. 1997; 62(14):4591-4600.
Delrieu et al., Emergence of epidemic Neisseria meningitidis serogroup X meningitis in Togo and Burkina Faso. PLoS One. 2011;6(5):e19513.
Dick et al., Glycoconjugates of bacterial carbohydrate antigens. A survey and consideration of design and preparation factors. Contrib Microbiol Immunol. 1989;10:48-114.
Domenighini et al., Identification of errors among database sequence entries and comparison of correct amino acid sequences for the heat-labile enterotoxins of *Escherichia coli* and Vibrio cholerae. Mol Microbiol. Mar. 1995;15(6)1165-7.
Donnelly et al., Antigen presentation and DNA vaccines. Am J Respir Crit Care Med. Oct. 2000;162(4 Pt 2):S190-3.
Donnelly et al., DNA vaccines. Annu Rev Immunol. 1997;15:617-48.
Dreesen, A global review of rabies vaccines for human use. Vaccine. 1997 Spring;15 Suppl:S2-6.
Dubensky et al., Delivery systems for gene-based vaccines. Mol Med. Sep. 2000;6(9):723-32.
Egan et al., Structural studies and chemistry of bacterial capsular polysaccharides. Investigations of phosphodiester-linked capsular polysaccharides isolated from Haemophilus influenzae types a, b, c, and f: NMR spectroscopic identification and chemical modification of end groups and the nature of base-catalyzed hydrolytic depolymerization. J Am Chem. 1982, 104(10):2898-2910.
Evans et al., Enhancement of antigen-specific immunity via the TLR4 ligands MPL adjuvant and Ribi.529. Expert Rev Vaccines. Apr. 2003;2(2):219-29.
Falugi et al., Rationally designed strings of promiscuous CD4(+) T cell epitopes provide help to Haemophilus influenzae type b oligosaccharide: a model for new conjugate vaccines. Eur J Immunol. Dec. 2001;31(12):3816-24.
Feller et al., Identifying antigenic T-cell sites. Nature. Feb. 21, 1991;349(6311):720-1.
Ferretti et al., Complete genome sequence of an M1 strain of *Streptococcus pyogenes*. Proc Natl Acad Sci U S A. Apr. 10, 2001;98(8):4658-63.
Frash, Advances in Biotechnological Processes: Bacterial Vaccines. A. Mizrahi (Ed.), Wiley-Liss, Mar. 1990; vol. 13, pp. 123-145.
Frey et al., Comparison of the safety, tolerability, and immunogenicity of a MF59-adjuvanted influenza vaccine and a non-adjuvanted influenza vaccine in non-elderly adults. Vaccine. Oct. 1, 2003;21(27-30):4234-7.
Andrianov et al., Preparation of hydrogel microspheres by coacervation of aqueous polyphosphazene solutions. Biomaterials. Jan.-Feb. 1998;19(1-3):109-15.
Agarwal et al., Recent trends in drug delivery systems: intranasal drug delivery. Indian J Exp Biol. Jan. 1999;37(1):6-16.
Ahmad et al., Conjugated polysaccharide vaccines. Infect Dis Clin North Am. Mar. 1999;13(1):113-33.
Almeida et al., Nasal delivery of vaccines. J Drug Target. 1996;3(6):455-67.

Paoletti, Potency of clinical group B streptococcal conjugate vaccines. Vaccine. Feb. 28, 2001;19(15-16):2118-26.
Partidos et al., Heat-labile enterotoxin of *Escherichia coli* and its site-directed mutant LTK63 enhance the proliferative and cytotoxic T-cell responses to intranasally co-immunized synthetic peptides. Immunol Lett. Apr. 15, 1999;67(3):209-16.
Payne et al., Protein release from polyphosphazene matrices. Adv Drug Deilv Rev. May 4, 1998;31(3):185-196.
Peppoloni et al., Mutants of the *Escherichia coli* heat-labile enterotoxin as safe and strong adjuvants for intranasal delivery of vaccines. Expert Rev Vaccines. Apr. 2003;2(2):285-93.
Pine et al., Intranasal immunization with influenza vaccine and a detoxified mutant of heat labile enterotoxin from *Escherichia coli* (LTK63). J Control Release. Dec. 13, 2002;85(1-3):263-70.
Pinto et al., Cellular immune responses to human papillomavirus (HPV)-16 L1 in healthy volunteers immunized with recombinant HPV-16 L1 virus-like particles. J Infect Dis. Jul. 15, 2003;188(2):327-38.
Pizza et al., LTK63 and LTR72, two mucosal adjuvants ready for clinical trials. Int J Med Microbiol. Oct. 2000;290 (4-5):455-61.
Pizza et al., Mucosal vaccines: non toxic derivatives of LT and CT as mucosal adjuvants. Vaccine. Mar. 21, 2001;19(17-19):2534-41.
Plotkin et al., Meningococcal Vaccines. Vaccines, Fifth Edition, Saunders Elsevier, Chapter 19 (2008).
Podda, The adjuvanted influenza vaccines with novel adjuvants: experience with the MF59-adjuvanted vaccine. Vaccine. Mar. 21, 2001;19(17-19):2673-80.
Raddrizzani et al., Epitope scanning using virtual matrix-based algorithms. Brief Bioinform. May 2000;1(2):179-89.
Ramsay et al., Efficacy of meningococcal serogroup C conjugate vaccine in teenagers and toddlers in England. Lancet. Jan. 20, 2001;357(9251):195-6.
Rappuoli et al., Towards third-generation whooping cough vaccines. Trends Biotechnol. Jul. 1991;9(7):232-8.
Ravenscroft et al., Size determination of bacterial capsular oligosaccharides used to prepare conjugate vaccines. Vaccine. Jul. 16, 1999;17(22):2802-16.
Read et al., Genome sequences of Chlamydia trachomatis MoPn and Chlamydia pneumoniae AR39. Nucleic Acids Res. Mar. 15, 2000;28(6):1397-406.
Rennels et al., Dose escalation, safety and immunogenicity study of a tetravalent meningococcal polysaccharide diphthena conjugate vaccine in toddlers. Pediatr Infect Dis J. Oct. 2002;21(10):978-9.
Roberts et al., Prediction of HIV peptide epitopes by a novel algorithm. AIDS Res Hum Retroviruses. May 1, 1996;12(7):593-610.
Robinson et al., DNA vaccines for viral infections: basic studies and applications. Adv Virus Res. 2000;55:1-74.
Robinson et al., DNA vaccines. Semin Immunol. Oct. 1997;9(5):271-83.
Ross et al., Identification of vaccine candidate antigens from a genomic analysis of Porphyromonas gingivalis. Vaccine. Jul. 20, 2001;19(30):4135-42.
Ruan et al., Protein D of Haemophilus influenzae. A novel bacterial surface protein with affinity for human IgD. J Immunol. Nov. 15, 1990;145(10):3379-84.
Rubin, Pneumococcal vaccine. Pediatr Clin North Am. Apr. 2000;47(2):269-85.
Ryan et al., Mutants of *Escherichia coli* heat-labile toxin act as effective mucosal adjuvants for nasal delivery of an acellular pertussis vaccine: differential effects of the nontoxic AB complex and enzyme activity on Th1 and Th2 cells. Infect Immun. Dec. 1999;67(12):6270-80.
Scharton-Kersten et al., Transcutaneous immunization with bacterial ADP-ribosylating exotoxins, subunits, and unrelated adjuvants. Infect Immun. Sep. 2000;68(9):5306-13.
Scott-Taylor et al., DNA vaccines. Expert Opin Investig Drugs. Mar. 2000;9(3):471-80.
Shirai et al., Comparison of Outer Membrane Protein Genes omp and pmp in the Whole Genome Sequences of Chlamydia pneumoniae Isolates from Japan and the United States. J Infect Dis. 2000; 181(Suppl. 3):S524-S527.

(56) References Cited

OTHER PUBLICATIONS

Singh et al., A novel bioadhesive intranasal delivery system for inactivated influenza vaccines. J Control Release. Feb. 23, 2001;70(3):267-76.

Sjolander et al., Uptake and adjuvant activity of orally delivered saponin and ISCOM™ vaccines. Advanced Drug Delivery Reviews. Dec. 1998; 34(2-3):321-338.

Smith, Comparison of biosequences. Advances in Applied Mathematics, Dec. 1981; 2(4):482-489.

Stanley, Imiquimod and the imidazoquinolones: mechanism of action and therapeutic potential. Clin Exp Dermatol. Oct. 2002;27(7):571-7.

Sutter et al., Poliovirus vaccines. Progress toward global poliomyelitis eradication and changing routine immunization recommendations in the United States. Pediatr Clin North Am. Apr. 2000;47(2):287-308.

Teodorovic, Synthesis of oligosaccharides related to the capsular polysaccharide of Neisseria meningitidis serotype A, Doctoral Thesis; Stockholm University, Faculty of Science, Department of Organic Chemistry, 40 pages, 2005.

Tiesjema et al., Enhanced stability of meningococcal polysaccharide vaccines by using lactose as a menstruum for lyophilization. Bull World Health Organ, 1977, 55(1):43-48.

Ugozzoli et al., Combinations of protein polysaccharide conjugate vaccines for intranasal immunization. J Infect Dis. Nov 1, 2002;186(9)1358-61.

Vodopija et al., Reactivity and immunogenicity of bivalent (AC) and tetravalent (ACW135Y) meningococcal vaccines containing O-acetyl-negative or O-acetyl-positive group C polysaccharide. Infect Immun. Nov. 1983;42(2):599-604.

Wang et al., High-performance liquid chromatography of sialic acid-containing oligosaccharides and acidic monosaccharides. Anal Biochem. Nov. 1, 1990;190(2):182-7.

Watson, Pneumococcal conjugate vaccines. Pediatr Infect Dis J. Apr. 2000;19(4):331-2.

Welling et al., Prediction of sequential antigenic regions in proteins. FEBS Lett. Sep. 2, 1985;188(2):215-8.

Xie et al., Characterization of size, structure and purity of serogroup X Neisseria meningitidis polysaccharide, and development of an assay for quantification of human antibodies. Vaccine. Aug. 31, 2012;30(40):5812-23.

Zimmerman et al., Poliovirus vaccine options. Am Fam Physician. Jan. 1, 1999;59(1):113-8, 125-6.

Zon et al., Hydrolytic stability of pneumococcal group 6 (type 6A and 6B) capsular polysaccharides. Infect Immun. Jul. 1982;37(1):89-103.

\* cited by examiner

Acquity UPLC BEH200 1.7 μm (4.6 x 150 mm), 214 nm detection,
100mM NaCl 100mM NaPi 30% $CH_3CN$ pH 7.2; Vtot 4.343 min

FIGURE 3
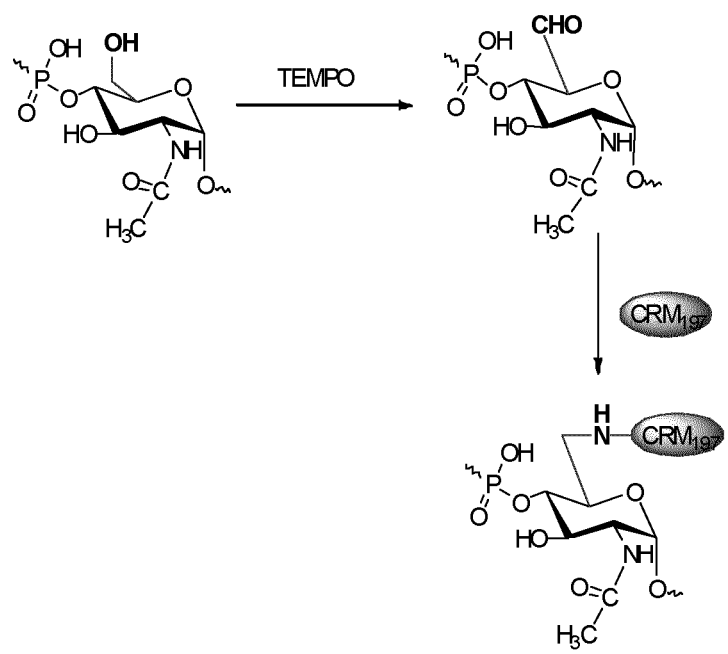
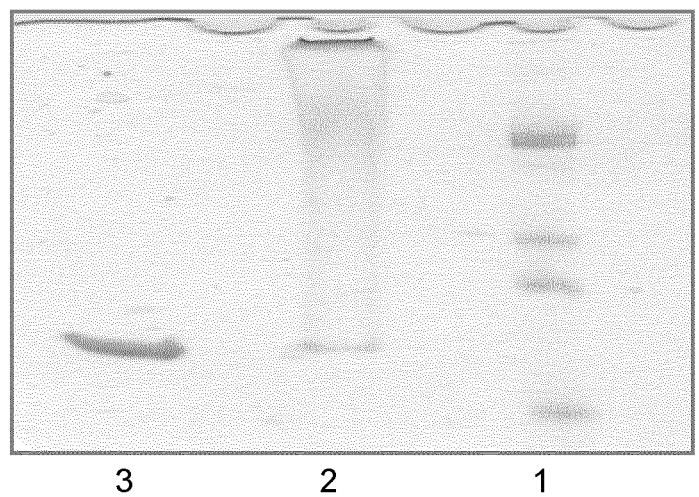
1. Marker
2. MenX-CRM$_{197}$
3. CRM$_{197}$

FIGURE 5
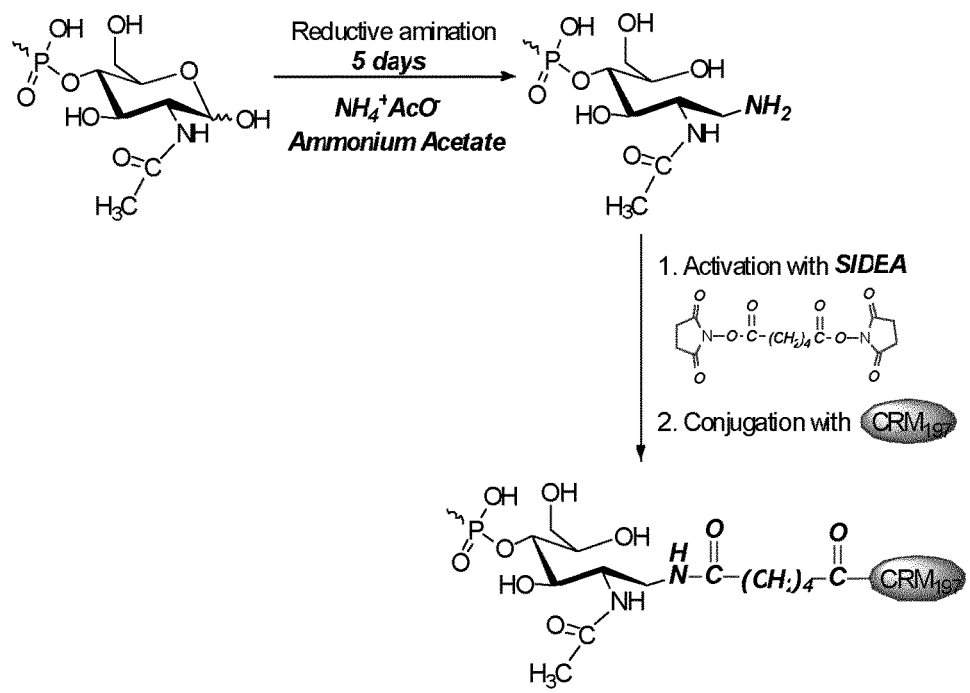
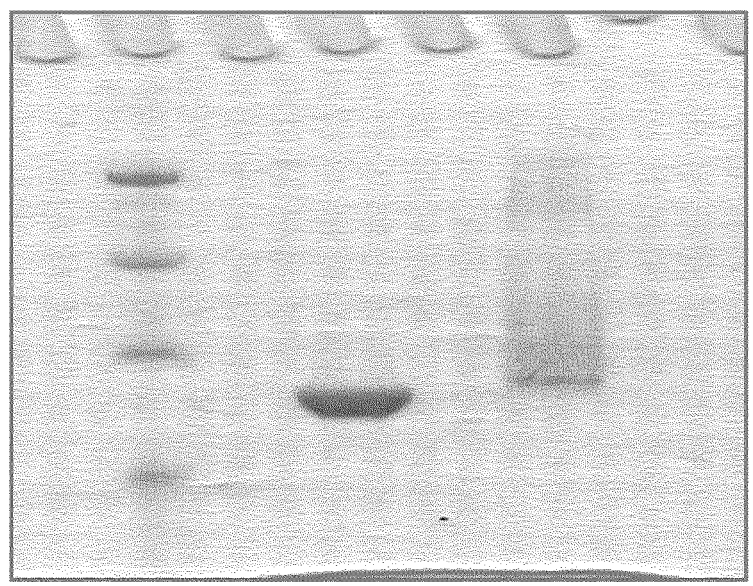
1. Marker
2. CRM$_{197}$
3. MenX-CRM$_{197}$

FIGURE 6
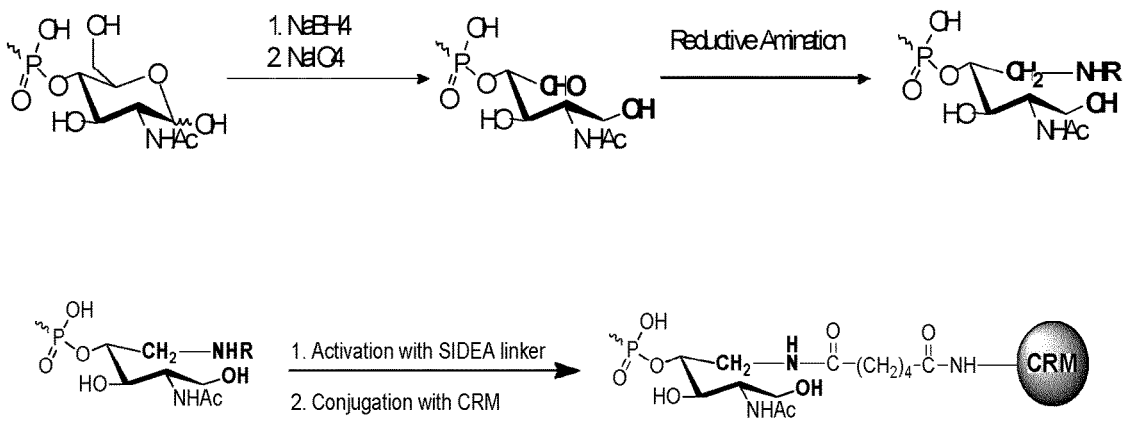
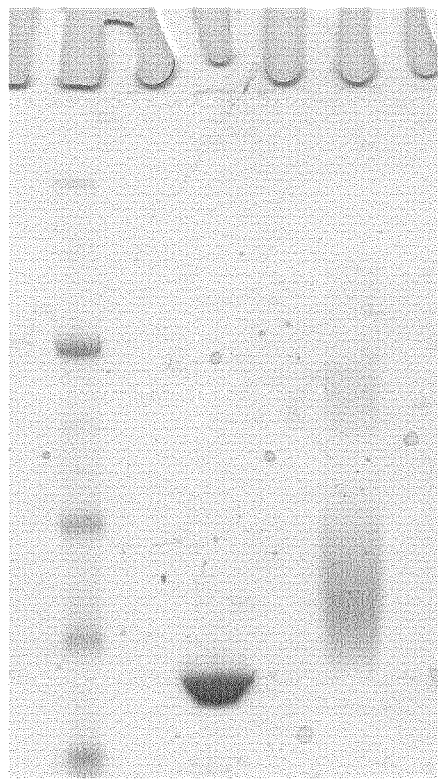
SDS-Page 7%TA
1. Marker
2. $CRM_{197}$
3. MenX-$CRM_{197}$
1  2  3

1. Marker
2. CRM$_{197}$
3. MenX-CRM$_{197}$

FIGURE 13
A)
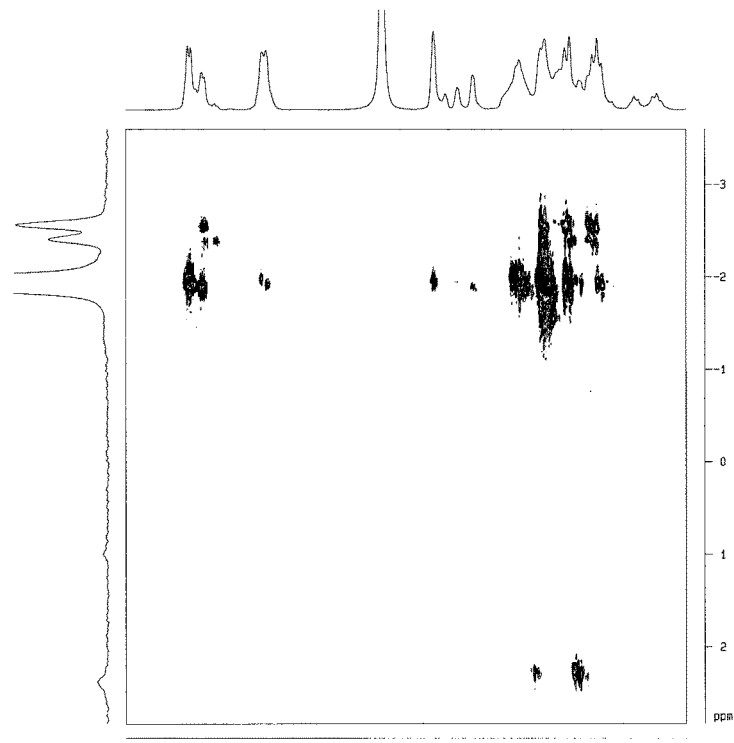
B)
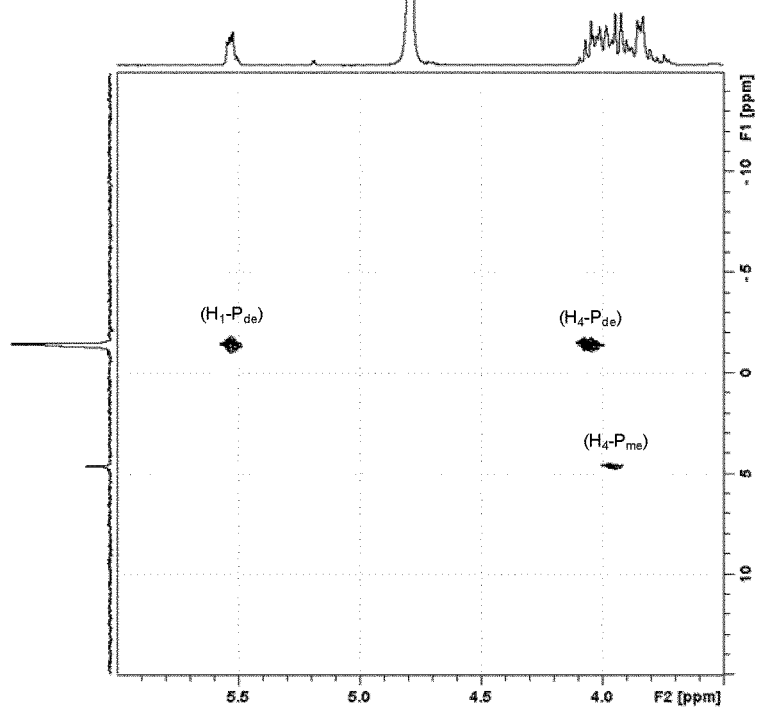

FIGURE 14
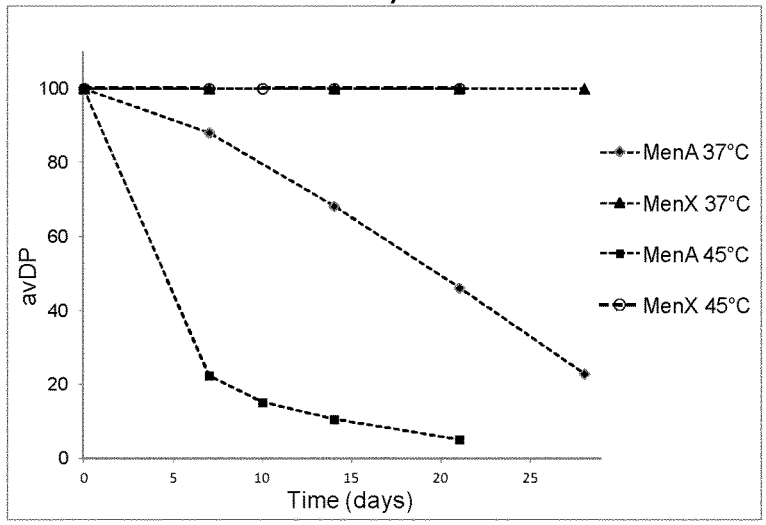
A)
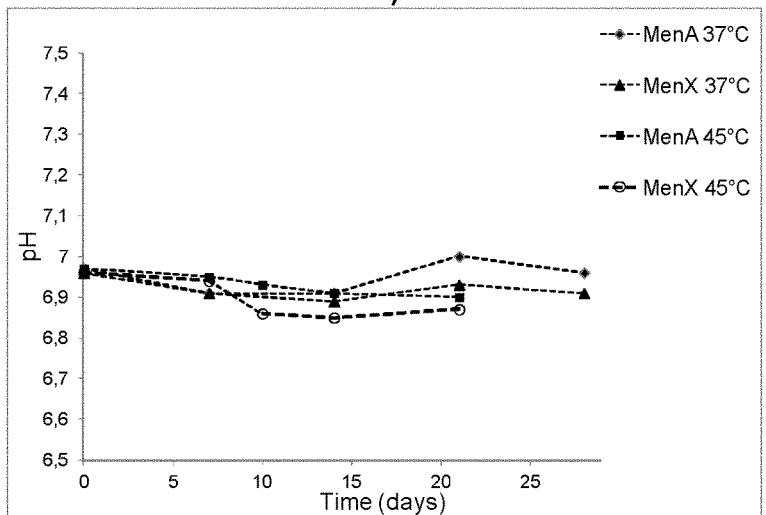
B)
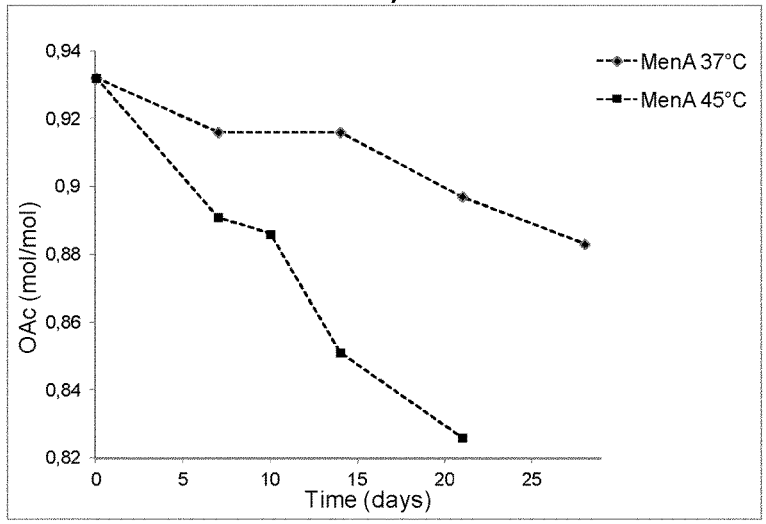
C)

FIGURE 15
A)
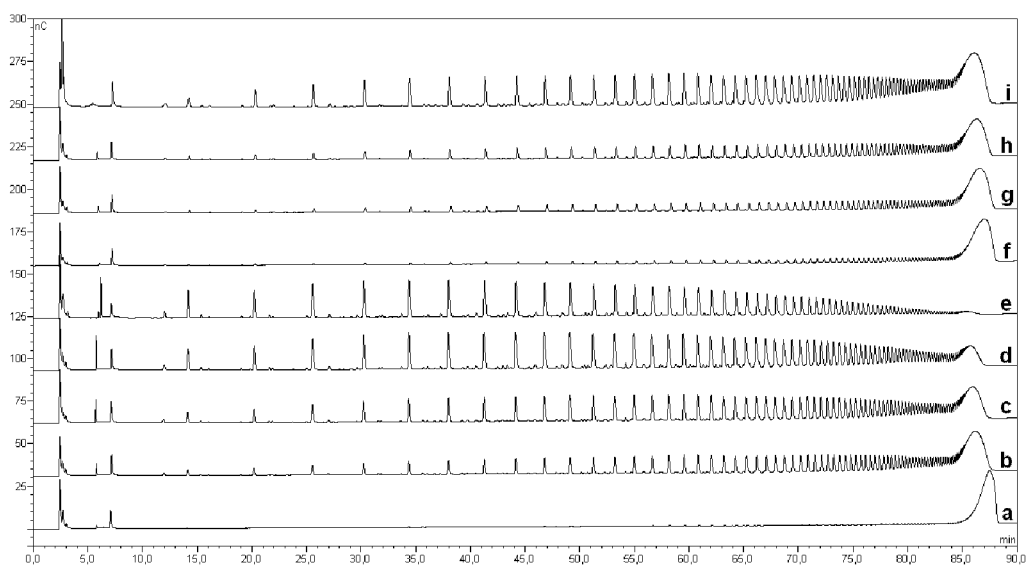
B)
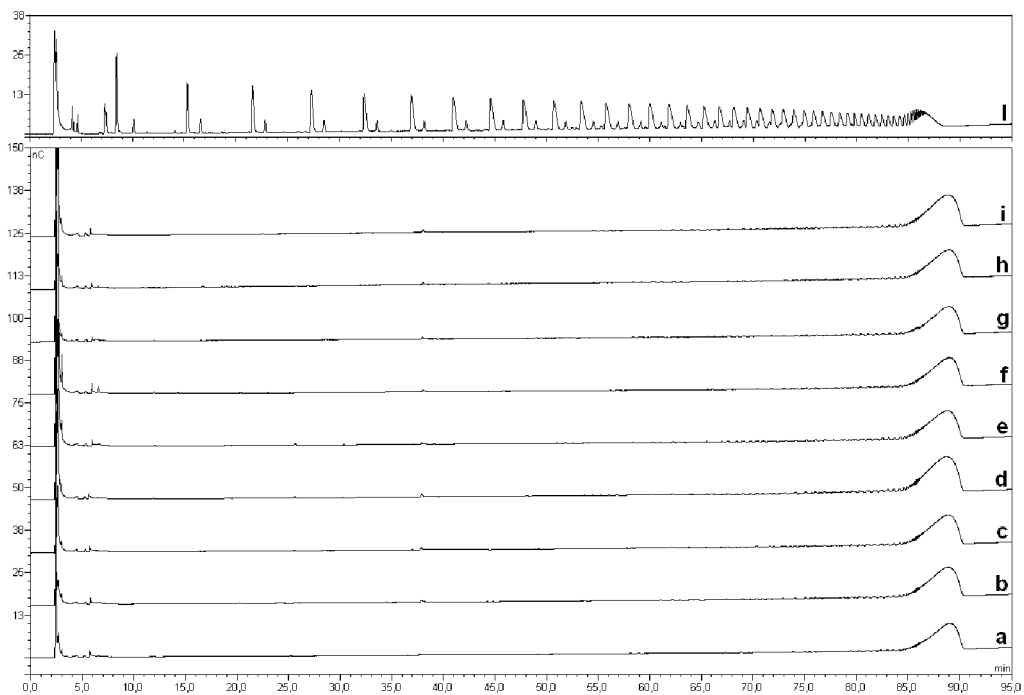

FIGURE 17
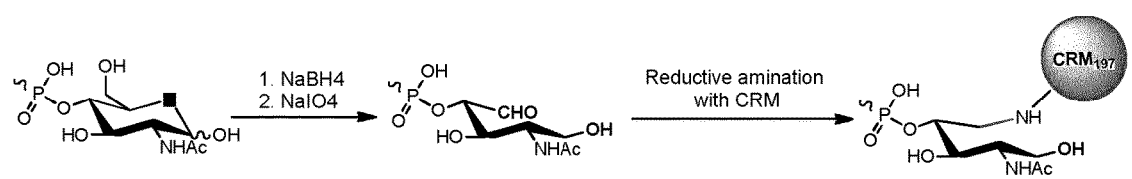
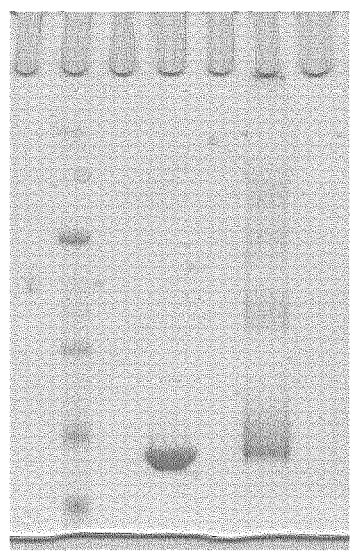
SDS-Page 3-8%TA
1. Marker
2. CRM$_{197}$
3. MenX-CRM$_{197}$
1   2   3

MENINGOCOCCUS SEROGROUP X CONJUGATE

RELATED APPLICATIONS

This application is the U.S. National Phase of International Patent Application No. PCT/EP2013/060447 filed May 22, 2013 and published in English, which claims the benefit of U.S. Provisional Application No. 61/650,025, filed May 22, 2012; U.S. Provisional Application No. 61/698,677, filed Sep. 9, 2012; and U.S. Provisional Application No. 61/799,528, filed Mar. 15, 2013. The entire contents of the foregoing applications are incorporated herein by reference for all purposes.

SEQUENCE LISTING

The application contains a Sequence Listing which was filed with International Patent Application No. PCT/EP2013/060447. The sequence listing is hereby incorporated by reference in its entirety.

TECHNICAL FIELD

This invention is in the field of bacterial capsular saccharides, particularly *Neisseria meningitidis* serogroup X capsular polysaccharides. The polysaccharides may be conjugated to carriers in order to form conjugates. The polysaccharides and conjugates are useful for immunisation, particularly in aqueous formulations.

BACKGROUND ART

The capsular saccharides of bacteria have been used for many years in vaccines against capsulated bacteria. As saccharides are T-independent antigens, however, they are poorly immunogenic. Conjugation to a carrier can convert T-independent antigens into T-dependent antigens, thereby enhancing memory responses and allowing protective immunity to develop. The most effective saccharide vaccines are therefore based on glycoconjugates, and the prototype conjugate vaccine was against *Haemophilus influenzae* type b ('Hib') [e.g. see chapter 14 of ref. 86].

Based on the organism's capsular polysaccharide, twelve serogroups of *N. meningitidis* have been identified (A, B, C, H, I, K, L, 29E, W135, X, Y and Z). Group A is the pathogen most often implicated in epidemic disease in sub-Saharan Africa. Serogroups B and C are responsible for the vast majority of cases in USA and in most developed countries. Serogroups W135 and Y are responsible for the remaining cases in USA and developed countries. A tetravalent vaccine of capsular polysaccharides from serogroups A, C, Y and W135 has been known for many years [1,2]. Although effective in adolescents and adults, it induces a poor immune response and short duration of protection and cannot be used in infants [e.g. ref. 3] because polysaccharides are T cell-independent antigens that induce a weak immune response which cannot be boosted. The polysaccharides in this vaccine are not conjugated [4]. Conjugate vaccines against serogroup C have been approved for human use, and include Menjugate™ [5], Meningitec™ and NeisVac-C™. Mixtures of conjugates from serogroups A+C are known [6-8] and mixtures of conjugates from serogroups A+C+W135+Y have been reported [9-13].

The structure of the group X capsular polysaccharide has been known since the 1970s [14] and this serogroup has been associated with a number of outbreaks of meningococcal disease, e.g. in sub-Saharan Africa and China [15,16]. Serogroup X is known to have a significantly higher attack rate than serogroup A among children below 5 years of age. Although the need for a vaccine against this serogroup has been recognised for many years [17], no effective vaccine has been developed. Conjugate vaccines against serogroup X have been proposed [17,18], but it remains unknown whether such conjugates would be immunogenic or protective against this serogroup.

Accordingly, there remains a need for conjugates of serogroup X capsular polysaccharides. Moreover, there remains a need for conjugates that can be used for vaccination against diseases caused by this serogroup.

The structure of the group X capsular polysaccharide consists of N-acetylglucosamine-4-phosphate residues held together by α1-4 phosphodiester bonds without O-acetyl groups [19]: {→4)-D-GlcpNAc-α-(1→OPO3→} (FIG. 1). Based on the similarity between their structures, a biosynthetic relationship between MenA and MenX capsular polysaccharides has been postulated [14]. MenA capsular polysaccharide tends to hydrolyse significantly in aqueous solution [20]. This instability is thought to be caused by the presence of a phosphodiester linkage involving the anomeric position and of the N-Acetyl group in position 2 of mannosamine, which can assist departure of a phosphomonoester group [21]. Another possibility is that the hydroxyl groups at position 4 of the N-acetylmannosamine subunits interact with the phosphodiester groups facilitating hydrolysis via an internal participation mechanism, as seen in the capsular polysaccharide of type 6A pneumococcus [22] and *Haemophilus influenzae* type b [23]. The similarity in the structures of the MenX and MenA capsular polysaccharides, particularly their common anomeric phosphodiester linkage, means that the MenX polysaccharide may suffer from similar stability problems when in aqueous solution. The intrinsic instability of the MenA capsular polysaccharide in aqueous solution means that it is often presented in a lyophilized form when contained in vaccines (e.g. in the polysaccharide vaccine Mencevax™ and the conjugate vaccines MenAfriVac™, Menveo™ and Nimenrix™). Although the MenX capsular polysaccharide could similarly be presented in a lyophilised form to improve its stability, an aqueous formulation would be more convenient. The only vaccine containing a MenA capsular polysaccharide conjugate in an aqueous formulation is Menactra™, but this vaccine requires storage at low temperatures. Such cold storage is expensive and presents practical difficulties in many of the countries where MenA and MenX outbreaks are common (e.g. sub-Saharan Africa).

Accordingly, there is a need for aqueous formulations of serogroup X capsular polysaccharides and conjugates thereof, particularly aqueous formulations that do not require refrigeration.

The development of a vaccine against MenX requires a method for polysaccharide quantification that can be used as an in-process assay and/or for the characterization of the final vaccine. The presence of phosphate groups in the MenX capsular polysaccharide means that the polysaccharide can be quantified by a colorimetric method that measures total phosphorus content [24]. However, this method lacks selectivity and therefore would not be suitable for certain in-process applications, e.g. for the analysis of polysaccharide in phosphate buffers or in the presence of phosphate-containing impurities. A more selective method would be NMR, which has been proposed already for MenX polysaccharide quantification [25]. However, this approach requires pure samples and a large amount of material.

Reference 26 demonstrates an alternative approach, where the MenX polysaccharide is quantified by HPAEC-PAD, which is more sensitive than NMR and more selective than measuring phosphate content. The authors of ref. 26 quantified the MenX polysaccharide by hydrolysing the sample to make glucosamine, and comparing the amount of glucosamine released against a calibration curve derived from an N-acetyl-glucosamine-6-phosphate quantitative standard. However, glucosamine may be present because of contamination, leading to inaccurate results. Accordingly, there is a need for alternative or improved methods for assaying the MenX polysaccharide, and in particular for methods that are more selective for MenX.

DISCLOSURE OF THE INVENTION

The invention is based in part on methods for conjugating a serogroup X capsular polysaccharide to a carrier molecule. The inventors have found that the resulting conjugates are immunogenic and capable of inducing a bactericidal antibody response. Serogroup X conjugates are therefore useful in immunogenic compositions, and in particular in vaccines. The inventors have also discovered that it is possible to combine serogroup X capsular polysaccharide antigens, e.g. serogroup X conjugates, with other antigens without losing the immune response to serogroup X. In particular, serogroup X conjugates may be combined with other conjugates, e.g. conjugates comprising other bacterial capsular saccharide antigens. Serogroup X conjugates are particularly suitable for combination with conjugates comprising capsular saccharide antigens from other *N. meningitidis* serogroups, e.g. serogroups A, C, W135 and Y. In these combinations, not only does the serogroup X conjugate retain its immunogenicity, but the serogroup A, C, W135 and/or Y conjugates also retain their immunogenicity. Furthermore, the inventors have also found that despite its structural similarity to the serogroup A capsular polysaccharide, the capsular polysaccharide from serogroup X is surprisingly stable in solution. Serogroup X capsular polysaccharides and conjugates thereof may therefore be particularly suitable for use in aqueous formulations.

In a first aspect, the invention provides a conjugate of a *Neisseria meningitidis* serogroup X capsular polysaccharide and a carrier molecule. The inventors have found that particularly stable conjugates of a serogroup X capsular polysaccharide and a carrier molecule may be made using the process of the first embodiment of the second aspect of the invention described below. For example, the conjugates may contain less than 50% free saccharide after 28 days at 37° C. The % free saccharide may be determined as described in Stability study (2) below. Accordingly, within the first aspect of the invention, the invention provides a conjugate of a serogroup X capsular polysaccharide and a carrier molecule comprising less than 50% free saccharide after 28 days at 37° C. The conjugate may in particular comprise less than 25% free saccharide, particularly less than 20% free saccharide and more particularly less than 15% free saccharide, e.g. about 10% free saccharide.

In a second aspect, the invention provides processes for preparing a conjugate of a serogroup X capsular polysaccharide and a carrier molecule, in particular the processes of the first, second and third embodiments described below. The second aspect also provides the process of the fourth embodiment described below. The conjugate of the first aspect of the invention is typically obtained or obtainable by one of these processes. However, the conjugate of the first aspect may alternatively be made by any suitable method. When the conjugate of the invention is made by one of these other methods, the method typically does not involve one or both of the following steps: a) coupling the polysaccharide to a linker, to form a polysaccharide-linker intermediate in which the free terminus of the linker is an ester group, particularly wherein the coupling takes place indirectly, i.e. with an additional linker that is used to derivatise the polysaccharide prior to coupling to the linker; and b) reductive amination by reacting a carbonyl group at the reducing terminus of the polysaccharide with a primary amine group at one terminus of a linker.

In a third aspect, the invention provides a pharmaceutical composition comprising (a) a serogroup X capsular polysaccharide, particularly in the form of a conjugate of the first aspect of the invention, and (b) a pharmaceutically acceptable carrier. The composition is typically in an aqueous formulation.

In other aspects, the invention provides intermediates that are useful in the processes of the invention and processes for preparing these intermediates. The invention also provides uses of the conjugate of the invention, e.g. within immunogenic compositions and, in particular, vaccines, and for raising an immune response in a mammal.

In a first embodiment of the second aspect of the invention, the invention provides a process for preparing a conjugate of a serogroup X capsular polysaccharide and a carrier molecule, comprising the steps of: (a) oxidising a primary hydroxyl group in the capsular polysaccharide, to give an oxidised polysaccharide with an aldehyde group; and (b) coupling the oxidised polysaccharide to a carrier molecule via the aldehyde group, thereby giving the conjugate. This process is thought to be particularly suitable (e.g. in terms of yield) for relatively long polysaccharides, e.g. those with a degree of polymerisation (DP) of between 20 and 200, particularly between 60 and 100 (e.g. between 70 and 90, particularly around 80). This process also contains relatively few steps, making it easier to scale-up to an industrial setting. The resulting conjugates may also be more stable, particularly compared to conjugates in which the polysaccharide is linked to the carrier via its reducing terminus. The coupling in step (b) is typically direct, e.g. by reductive amination between the aldehyde group and a primary amine group on the carrier molecule. As part of the first aspect of the invention, the invention also provides a conjugate obtained or obtainable by this process. The invention also provides the individual steps (a) and (b) of this process; and the oxidised polysaccharide intermediate obtained or obtainable by step (a) of this process.

In a second embodiment of the second aspect of the invention, the invention provides a process for preparing a conjugate of a serogroup X capsular polysaccharide and a carrier molecule, comprising the steps of: (a) reductive amination of the reducing terminus of the capsular polysaccharide, to give a modified polysaccharide with a primary amine group bonded to the C-1 atom of the terminal subunit by a covalent bond; and (b) coupling the modified polysaccharide to a carrier molecule via the primary amine group, thereby giving the conjugate. This process is particularly suitable for relatively short polysaccharides e.g. polysaccharides with a DP between 5 and 50, particularly between 10 and 20, e.g. about 15. The coupling in step (b) is typically indirect, e.g. via a linker. As part of the first aspect of the invention, the invention also provides a conjugate obtained or obtainable by this process. The invention also provides the individual steps (a) and (b) of this process; and the modified polysaccharide intermediate obtained or obtainable by step (a) of this process.

In a third embodiment of the second aspect of the invention, the invention provides a process for preparing a conjugate of a serogroup X capsular polysaccharide and a carrier molecule, comprising the steps of: (a) reduction of the reducing terminus of the capsular polysaccharide, to give a modified polysaccharide with two vicinal hydroxyl groups at that terminus; (b) oxidative cleavage of the vicinal hydroxyl groups, to give a further modified polysaccharide with an aldehyde group at the terminus; (c) reductive amination of the aldehyde group, to give a further modified polysaccharide with a primary amine group at the terminus and (d) coupling the further modified polysaccharide to a carrier molecule via the primary amine group, thereby giving the conjugate. This process may provide a better yield than the processes of the first and second embodiment, particularly for relatively short polysaccharides e.g. polysaccharides with a DP between 5 and 50, particularly between 10 and 20, e.g. about 15. The coupling in step (d) is typically indirect, e.g. via a linker. As part of the first aspect of the invention, the invention also provides a conjugate obtained or obtainable by this process. The invention also provides the individual steps (a), (b), (c) and (d) of this process and the combinations of steps (a) and (b), (b) and (c), (c) and (d), (a), (b) and (c) and (b), (c) and (d); and the modified polysaccharide intermediates obtained or obtainable by steps (a), (b) or (c) of this process.

In a fourth embodiment of the second aspect of the invention, the invention provides a process for preparing a conjugate of a serogroup X capsular polysaccharide and a carrier molecule, comprising the steps of: (a) reduction of the reducing terminus of the capsular polysaccharide, to give a modified polysaccharide with two vicinal hydroxyl groups at that terminus; (b) oxidative cleavage of the vicinal hydroxyl groups, to give a further modified polysaccharide with an aldehyde group at the terminus; (c) direct coupling of the further modified polysaccharide to the carrier molecule by reductive amination of the aldehyde group with a primary amine group on the carrier molecule, thereby giving the conjugate. As part of the first aspect of the invention, the invention also provides a conjugate obtained or obtainable by this process. The invention also provides the individual steps (a), (b) and (c) of this process and the combinations of steps (a) and (b) and (b) and (c); and the modified polysaccharide intermediates obtained or obtainable by steps (a) or (b) of this process.

The inventors have also developed a method for assaying serogroup X capsular polysaccharide. The method involves the detection of glucosamine-4-phosphate, which is characteristic of the MenX polysaccharide and not usually present in impurities. Accordingly, in a yet further aspect, the invention provides a method for assaying a sample suspected to contain serogroup X capsular polysaccharide, comprising the steps of: (i) hydrolysing any serogroup X capsular polysaccharide in the sample, to give a hydrolysate; (ii) subjecting the hydrolysate to liquid chromatography; and (iii) detecting any glucosamine-4-phosphate separated in step (ii).

In a further aspect, the invention provides processes and reagents useful for preparing N-acetylglucosamine-4-phosphate. This compound may be used as an analytical standard in the method for assaying serogroup X capsular polysaccharide described above.

The Capsular Polysaccharide

The invention involves the capsular polysaccharide of *N. meningitidis* serogroup X. The structure of the group X capsular polysaccharide consists of N-acetylglucosamine-4- phosphate residues held together by α1-4 phosphodiester bonds without O-acetyl groups [19]: {→4)-D-GlcpNAc-α-(1→OPO3→}(FIG. 1).

The capsular polysaccharide can be purified by known techniques, for example by the method described in ref. 19. In general, meningococcal capsular polysaccharides are prepared by a process comprising the steps of polysaccharide precipitation (e.g. using a cationic detergent), ethanol fractionation, cold phenol extraction (to remove protein) and ultracentrifugation (to remove LPS) [e.g. ref. 27]. However, a preferred process for the serogroup X capsular polysaccharide is described in ref. 10. This process involves polysaccharide precipitation followed by solubilisation of the precipitated polysaccharide using a lower alcohol. Precipitation can be achieved using a cationic detergent such as tetrabutylammonium and cetyltrimethylammonium salts (e.g. the bromide salts), or hexadimethrine bromide and myristyltrimethylammonium salts. Cetyltrimethylammonium bromide ('CTAB') is typically used [28]. Solubilisation of the precipitated material can be achieved using a lower alcohol such as methanol, propan-1-ol, propan-2-ol, butan-1-ol, butan-2-ol, 2-methyl-propan-1-ol, 2-methyl-propan-2-ol, diols, etc., but ethanol is particularly suitable for solubilising CTAB-polysaccharide complexes. Ethanol is preferably added to the precipitated polysaccharide to give a final ethanol concentration (based on total content of ethanol and water) of between 50% and 95%.

After re-solubilisation, the polysaccharide may be further treated to remove contaminants. This is particularly important in situations where even minor contamination is not acceptable (e.g. for human vaccine production). This will typically involve one or more steps of filtration e.g. depth filtration, filtration through activated carbon may be used, size filtration and/or ultrafiltration.

Once filtered to remove contaminants, the polysaccharide may be precipitated for further treatment and/or processing. This can be conveniently achieved by exchanging cations (e.g. by the addition of calcium or sodium salts).

The invention is not limited to polysaccharides purified from natural sources, however, and the polysaccharides may be obtained by other methods, such as total or partial synthesis, e.g. by the enzymatic synthesis described in ref. 29.

The polysaccharide may be chemically modified relative to the capsular polysaccharide as found in nature. For example, the polysaccharide may be de-N-acetylated (partially or fully), N-propionated (partially or fully), etc. De-acetylation may occur before, during or after conjugation, but typically occurs before conjugation. The degree of N-acetylation of the serogroup X capsular polysaccharide used in the invention may be 0-100%, 50-100%, 75-100%, 80-100%, 90-100%, or 95-100%. Typically, the degree of N-acetylation is 100%. The degree of N-acetylation of the polysaccharide can be determined by any method known in the art, for example, by proton NMR (e.g. as described in references 30 and 31.

Capsular polysaccharides will generally be used in the form of oligosaccharides. These are conveniently formed by fragmentation of purified capsular polysaccharide (e.g. by hydrolysis), which will usually be followed by purification of the fragments of the desired size.

Fragmentation of polysaccharides is preferably performed to give a final average degree of polymerisation (DP) in the oligosaccharide of between 20 and 200, particularly between 60 and 100 (e.g. between 70 and 90, particularly around 80). The inventors have found that polysaccharides of this length are particularly suitable for use in the process of the first embodiment described above. However, the inventors have found that shorter polysaccharides may also be used, e.g. polysaccharides with a DP between 5 and 50, particularly between 10 and 20, e.g. about 15. The inventors have found that polysaccharides of this length are particularly suitable for use in the process of the second and third embodiments described above. DP can conveniently be measured by ion exchange chromatography, NMR or by colorimetric assays [32].

The polysaccharide may be sized in order to obtain a desired range of polysaccharide sizes [33]. This can be achieved in various ways, such as ultrafiltration followed by ion-exchange chromatography.

The Carrier Molecule

The invention involves the use of carrier molecules, which are typically proteins. In general, covalent conjugation of saccharides to carriers enhances the immunogenicity of saccharides as it converts them from T-independent antigens to T-dependent antigens, thus allowing priming for immunological memory. Conjugation is particularly useful for paediatric vaccines [e.g. ref. 34] and is a well known technique [e.g. reviewed in refs. 35 to 43].

Preferred carrier proteins are bacterial toxins, such as diphtheria or tetanus toxins, or toxoids or mutants thereof, particularly diphtheria toxoid or tetanus toxoid. The inventors have found that the CRM197 diphtheria toxin mutant [44] is particularly suitable. Protein D from *H. influenzae* [45-47] may also be used.

Other suitable carrier proteins include the *N. meningitidis* outer membrane protein complex [48], synthetic peptides [49,50], heat shock proteins [51,52], pertussis proteins [53, 54], cytokines [55], lymphokines [55], hormones [55], growth factors [55], human serum albumin (typically recombinant), artificial proteins comprising multiple human CD4⁻ T cell epitopes from various pathogen-derived antigens [56] such as N19 [57], pneumococcal surface protein PspA [58], pneumolysin [59] or its non-toxic derivatives [60], iron-uptake proteins [61], toxin A or B from *C. difficile* [62], a GBS protein [63], a GAS protein [64] etc.

Other suitable carrier proteins are described in ref. 65, in particular the carrier protein of SEQ ID NO: 9 in that document. These carrier proteins are also described in ref. 66, and further details are provided in the section "Exemplary carrier proteins" below.

Oxidation

In step (a) of the process of the first embodiment described above, a primary hydroxyl group in the capsular polysaccharide is oxidised to give an aldehyde group. The primary hydroxyl group is bonded to the C-6 atom of a MenX capsular polysaccharide subunit by a covalent bond, such that the step proceeds as follows:

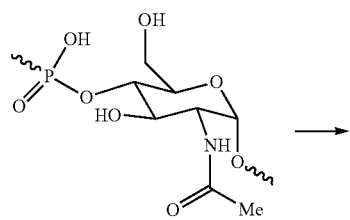

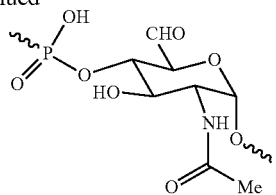

This step may involve oxidation of more than one such primary hydroxyl group, resulting in the introduction of more than one aldehyde group along the polysaccharide chain. For example, the inventors have found that suitable conjugates can be prepared by oxidising the primary hydroxyl group on between 1-50%, particularly 1-20% and more particularly 1-10%, e.g. about 4-8%, of residues within the serogroup X polysaccharide. Hydroxyl groups may be converted to aldehydes by various oxidation reactions (e.g. Swern oxidation, Dess-Martin oxidation, $Cr^{VI}$ oxidations, etc.). However the inventors have found that the TEMPO (2,2,6,6-tetramethylpiperidinyloxy radical)-mediated oxidation is particularly suitable. TEMPO-mediated oxidation is described in of ref. 67. To prevent oxidation of the aldehyde group to a carboxyl group, TEMPO-mediated oxidation is preferably carried out in non-aqueous conditions, e.g. using a DMF solvent as described in ref. 68. The skilled person would be capable of identifying suitable conditions for oxidation. For example, the inventors have found that treatment of polysaccharide with TEMPO (0.06 eq relative to the MenX repeating subunit), $NaHCO_3$ (9 eq relative to the MenX repeating subunit) and TCC (trichloroisocyanuric acid, 2 eq relative to the MenX repeating subunit) at 0° C. overnight is suitable.

Oxidative Cleavage

In step (b) of the process of the third and fourth embodiments described above, two vicinal hydroxyl groups in the capsular polysaccharide undergo oxidative cleavage to give an aldehyde group:

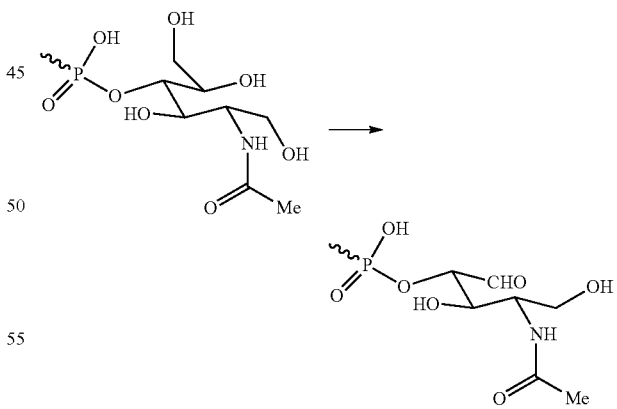

Oxidative cleavage (e.g. using $NaIO_4$, $Pb(OAc)_4$, etc.) is well known in the art. The inventors have found that reacting the polysaccharide at 6-8 mg/ml in 10 mM NaPi buffer at pH 7.2 with $NaIO_4$ (10 eq relative to the molecular weight of MenX, solid) for 1.5 hours at room temperature is suitable.

Reduction

In step (a) of the process of the third and fourth embodiments described above, the reducing terminus of the capsular polysaccharide is reduced to give a modified polysaccharide with two vicinal hydroxyl groups at the terminus:

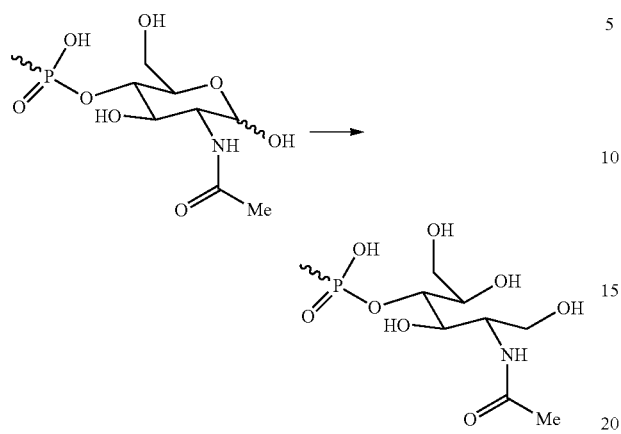

Reduction of polysaccharides (e.g. using NaBH$_4$, etc.) is well known in the art. The inventors have found that reacting the polysaccharide at 15 mg/ml in 10 mM NaPi buffer at pH 8 with NaBH$_4$ (12 eq relative to the molecular weight of MenX, solid) for 1.5 hours at room temperature is suitable.

Reductive Amination

In step (a) of the process of the second embodiment described above, the reducing terminus of the capsular polysaccharide is subjected to reductive amination to give a modified polysaccharide with a primary amine group bonded to the C-1 atom of the terminal subunit by a covalent bond:

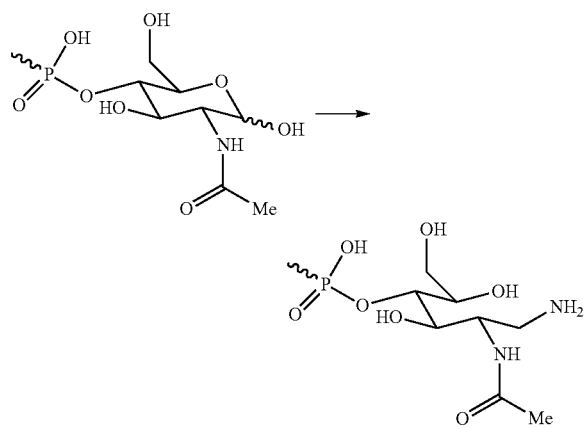

Reductive amination is a standard technique in organic chemistry. For example, the aldehyde group at the reducing terminus may be converted into a primary amine group using ammonia. This can conveniently be achieved using an ammonium salt (e.g. ammonium chloride or ammonium acetate) in combination with an appropriate reducing agent (e.g. cyanoborohydrides, such as sodium cyanoborohydride NaBH$_3$CN; borane-pyridine; sodium triacetoxyborohydride; borohydride exchange resin). The skilled person would be capable of identifying suitable conditions for reductive amination.

Reductive amination is also carried out in step (c) of the process of the third embodiment described above, to give a modified polysaccharide with a primary amine group at the terminus. For example, the aldehyde group may be converted into a primary amine group as described above. The reductive amination may therefore result in a modified polysaccharide with a primary amine group bonded to the C-5 atom of the terminal subunit by a covalent bond:

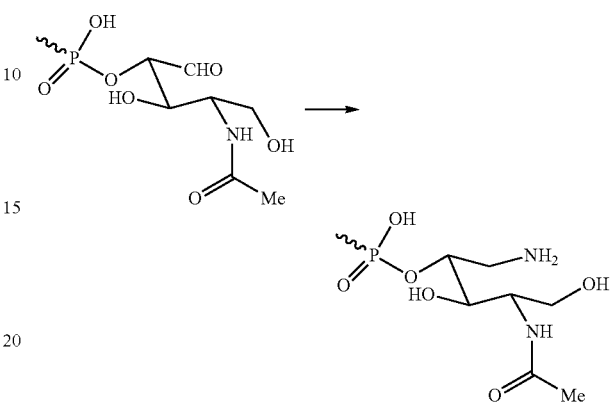

However, in other examples of the third embodiment, the reductive amination is between the aldehyde group and a terminal primary amine group of a linker. The linker is a bifunctional linker that provides a first terminal primary amine group for reacting with the aldehyde group and a second terminal primary amine group to act as the primary amine group at the terminus of the modified polysaccharide. For example, a bifunctional linker of the formula $X_1$-L-$X_2$ may be used as the linker, where $X_1$ comprises a primary amine group that can react with the aldehyde group; $X_2$ comprises a primary amine group; and L is a linking moiety in the linker. Typical L groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —(CH$_2$)$_4$—. Homobifunctional linkers of the formula X-L-X are particularly suitable as the linker, where the two X groups are the same as each other; and where L is a linking moiety in the linker. A typical X group is a —NHNH$_2$ group. L typically has formula -L'-L$^2$-L'-, where L' is carbonyl. Typical L$^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$), particularly —(CH$_2$)$_4$—. A typical linker is thus adipic acid dihydrazide (ADH). Shorter linkers may also be used, e.g. carbodihydrazine (CDH, i.e. X-L-X, wherein X is —NHNH$_2$ and L is carbonyl).

Reductive amination is also carried out in step (c) of the process of the fourth embodiment described above, to give the conjugate. The reductive amination is between the aldehyde group of the further modified polysaccharide and a primary amine group on the carrier molecule.

Coupling to a Carrier Molecule

The coupling of the oxidised polysaccharide to the carrier molecule via the aldehyde group in step (b) of the first embodiment described above may be direct or via a linker. However, the coupling is preferably direct because this involves fewer synthetic steps. The coupling of the modified polysaccharide to the carrier molecule via the primary amine group in step (b) of the second embodiment described above may also be direct or via a linker. In this embodiment, a linker is typically used to provide space between the polysaccharide and the carrier molecule. The coupling of the modified polysaccharide to the carrier molecule via the primary amine group in step (d) of the third embodiment described above may also be direct or via a linker. In this embodiment, a linker is typically used, once again to provide space between the polysaccharide and the carrier molecule. For all three embodiments, any suitable conjugation reaction can be used, with any suitable linker if desired.

Attachment of the polysaccharide or linker-derivatised polysaccharide to the carrier is typically via a primary amine (—$NH_2$) group e.g. in the side chain of a lysine or residue in a carrier protein, or of an arginine residue. Attachment to the carrier may also be via a sulphydryl (—SH) group e.g. in the side chain of a cysteine residue.

For the process of the first embodiment described above, the inventors have found that direct coupling may be conveniently achieved by reacting the aldehyde group in the oxidised polysaccharide with an amine group in the carrier by reductive amination. Direct coupling of this nature is therefore preferred in this embodiment. As discussed above, reductive amination is a standard technique, and has been used extensively in the production of conjugates of capsular polysaccharides for vaccine use. In one approach, an aldehyde group in the oxidised polysaccharide reacts with an amine group in the carrier. This can conveniently be achieved by combining the polysaccharide with the carrier in the presence of an appropriate reducing agent (e.g. cyanoborohydrides, such as sodium cyanoborohydride $NaBH_3CN$; borane-pyridine; sodium triacetoxyborohydride; borohydride exchange resin; etc.). The skilled person would be capable of identifying suitable conditions for reductive amination. For example, the inventors have found that treatment of oxidised polysaccharide with 10 mg/ml CRM197 at a 4:1 w/w ratio and $NaBH_3CN$ at a 1:1 w/w ratio in a NaPi 10 mM pH 7.2 buffer is suitable. This mixture may be left for 72 hours with slow stirring at 37° C. to effect the reductive amination. If desired, coupling via a linker may be used in this embodiment, e.g. by reacting the aldehyde group in the oxidised polysaccharide with an amine group in the linker by reductive amination, or by converting the aldehyde group into an amine group by reductive amination to provide an amine group for attachment of the linker.

In the processes of all embodiments, coupling via a linker may be made using any known procedure. For example, when the polysaccharide comprises an aldehyde group (e.g. the aldehyde group generated in step (a) of the process of the first embodiment described above), a bifunctional linker may be used to provide a first group for coupling to the aldehyde group and a second group for coupling to the carrier. For example, a bifunctional linker of the formula $X_1$-L-$X_2$ may be used, where $X_1$ can react with the aldehyde; $X_2$ can react with the carrier; and L is a linking moiety in the linker. A typical $X_1$ group is an amine group. Typical L groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$— or —$(CH_2)_3$—. Similarly, when the polysaccharide comprises a primary amine group (e.g. the primary amine group generated in step (a) of the process of the second embodiment or the primary amine group generated in step (c) of the process of the third embodiment), a bifunctional linker may be used to provide a first group for coupling to the amine group and a second group for coupling to the carrier (typically for coupling to an amine in the carrier). For example, a homobifunctional linker of the formula X-L-X may be used, where the two X groups are the same as each other and can react with the amines; and where L is a linking moiety in the linker. A typical X group is N-oxysuccinimide. L typically has formula -L'-$L^2$-L'-, where L' is carbonyl. Typical $L^2$ groups are straight chain alkyls with 1 to 10 carbon atoms (e.g. $C_1$, $C_2$, $C_3$, $C_4$, $C_5$, $C_6$, $C_7$, $C_8$, $C_9$, $C_{10}$) e.g. —$(CH_2)_4$—. A typical linker is thus adipic acid N-hydroxysuccinimide diester (SIDEA):

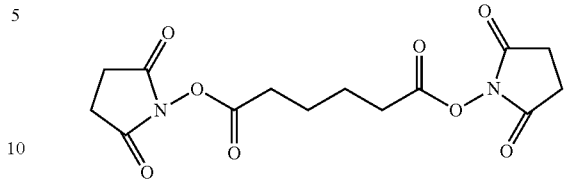

Other X groups are those which form esters when combined with HO-L-OH, such as norborane, p-nitrobenzoic acid, and sulfo-N-hydroxysuccinimide. Further bifunctional linkers reactive with amines for use with the invention include acryloyl halides (e.g. chloride) [70], haloacylhalides [71], disuccinimidyl glutarate, disuccinimidyl suberate, ethylene glycol bis[succinimidylsuccinate], etc.

The linker will generally be added in molar excess to the polysaccharide. The linker/polysaccharide reaction will generally take place in an aprotic solvent (e.g. DMSO, ethanol acetate, etc.), as the linkers are typically insoluble in water. Where water-soluble linkers are used, however, then a wider range of solvents is available, including protic solvents such as water. Suitable linkers include sulphonated forms, such as sulphonated SIDEA:

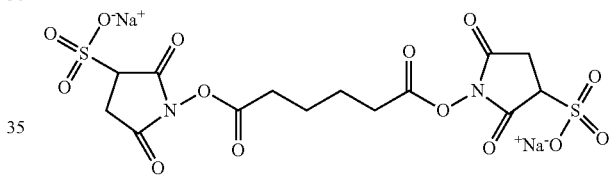

When a linker is used, the conjugate will comprise a linker moiety. This moiety originates neither in the polysaccharide nor the carrier, but is a third molecule used during conjugate preparation, and can readily be distinguished from both the polysaccharide and carrier protein in a final conjugate product. The linker moiety may include atoms such as carbon, hydrogen, oxygen and/or nitrogen. Linkers that comprise carbon and hydrogen are typical, and linkers that further comprise oxygen and/or nitrogen are also typically used. Linkers that include nitrogen atoms may include a carbon atom bonded to a nitrogen atom, which in turn is bonded to a second carbon atom (—C—N—C—). Linkers that include an oxygen atom typically include it as part of a carbonyl group. Linker moieties with a molecular weight of between 30-500 Da are typical. Linkers containing two carbonyl groups are also typical.

A particularly useful linker moiety is —NH—C(O)—$(CH_2)_n$—C(O)—, wherein n is 1, 2, 3, 4, 5, 6, 7, 8, 9 or 10. The value of n is typically 4. The terminal —NH— in this linker is usually attached to a carbon atom from the polysaccharide moiety. The terminal —C(O)— is usually attached to a nitrogen atom in an amino acid side chain in the carrier. A preferred linker moiety can conveniently be introduced by a process involving: reaction of an —$NH_2$ group in the polysaccharide with a bifunctional linker that is a diester (e.g. a disuccinimidyl ester) of a dioic acid (e.g. of adipic acid, HOOC—$(CH_2)_4$—COOH); and reductive amination of the product (see FIG. 6).

Other chemistries that can be used to attach a linker to a —NH$_2$ group in the polysaccharide, include:

acryloylation (e.g. by reaction with acryloyl chloride), followed by Michael-type addition to either the ε-NH$_2$ of an amino acid side chain or to a —SH of a cysteine side chain [70]. The resulting linker is —NH—C(O)—(CH$_2$)$_2$— (propionamido).

reaction with a haloacylhalide, followed by reaction with the ε-NH$_2$ of an amino acid side chain or to a —SH of a cysteine side chain [71]. The linker is —NH—C(O)—CH$_2$—.

Conjugates with a polysaccharide:protein ratio (w/w) of between 1:20 (i.e. excess protein) and 20:1 (i.e. excess polysaccharide) are typically produced by the method of the invention. Ratios of 1:10 to 1:1 are preferred, particularly ratios between 1:2 and 1:1 and, most preferably, about 1:1.5. For conjugates made by the process of the first embodiment of the second aspect of the invention, a typical ratio is between 0.1 and 1.0, more particularly between 0.2 and 0.4, e.g. about 0.35. For conjugates made by the process of the second embodiment of the second aspect of the invention, a typical ratio is between 0.1 and 1.0, more particularly between 0.1 and 0.3, e.g. about 0.22. For conjugates made by the process of the third embodiment of the second aspect of the invention, a typical ratio is between is between 0.1 and 1.0, more particularly between 0.1 and 0.3, e.g. about 0.21.

Compositions may include a small amount of free carrier [72]. When a given carrier protein is present in both free and conjugated form in a composition of the invention, the unconjugated form is preferably no more than 5% of the total amount of the carrier protein in the composition as a whole, and more preferably present at less than 2% by weight.

After conjugation, free and conjugated polysaccharides can be separated. There are many suitable methods, including hydrophobic chromatography, tangential ultrafiltration, diafiltration etc. [see also refs. 73 & 74, etc.].

Combinations of Conjugates and Other Antigens

As well as providing individual conjugates as described above, the invention provides a composition comprising a conjugate of the invention and one or more further antigens. The composition is typically an immunogenic composition.

The further antigen(s) may comprise further conjugates. In these embodiments, it is possible to use more than one carrier for the different conjugates in the composition, e.g. to reduce the risk of carrier suppression. Typically, the same carrier is used for all conjugates, including the conjugate of the invention. However, the inventors have found that the use of a different carrier for the conjugate of the invention may reduce immune interference when the conjugate is combined with further conjugate(s). Accordingly, in some embodiments, the conjugate of the invention uses one carrier (particularly tetanus toxoid or SEQ ID NO: 9 of ref. 65 and ref. 66), while the further conjugate(s) use a different carrier (particularly CRM197).

A single carrier protein might carry more than one polysaccharide antigen [75,76]. To achieve this goal, different polysaccharides can be mixed prior to the conjugation process. Typically, however, there are separate conjugates for each polysaccharide, with the different polysaccharides being mixed after conjugation. The separate conjugates are typically based on the same carrier, as discussed above.

The further antigen(s) may in particular be selected from the group consisting of serogroup A capsular polysaccharide, serogroup C capsular polysaccharide, serogroup Y capsular polysaccharide and serogroup W135 capsular polysaccharide. Typically, the further antigen(s) selected from this group are each separately conjugated to a carrier protein. Preferred carrier proteins are bacterial toxins, such as diphtheria or tetanus toxins, or toxoids or mutants thereof, particularly diphtheria toxoid or tetanus toxoid. The inventors have found that the CRM197 diphtheria toxin mutant is particularly suitable. Protein D from *H. influenzae* may also be used. Typically, the same carrier protein is used for all of the conjugates, optionally including the conjugate of the invention. The inventors have found that the CRM197 diphtheria toxin mutant is particularly suitable, although diphtheria toxoid and tetanus toxoid may also be used. As noted above, the inventors have found that the use of a different carrier for the conjugate of the invention may reduce immune interference when the conjugate is combined with further conjugate(s). Accordingly, in some embodiments, the conjugate of the invention uses one carrier (particularly tetanus toxoid or SEQ ID NO: 9 of ref. 65 and ref. 66), while the further conjugate(s) uses a different carrier (particularly CRM197).

The following combinations are specifically envisaged for use in the invention:

1) a conjugate of the invention and a conjugate of a serogroup A capsular polysaccharide and a carrier protein;
2) a conjugate of the invention and a conjugate of a serogroup W135 capsular polysaccharide and a carrier protein;
3) a conjugate of the invention, a conjugate of a serogroup A capsular polysaccharide and a carrier protein, and a conjugate of a serogroup W135 capsular polysaccharide and a carrier protein; and
4) a conjugate of the invention, a conjugate of a serogroup A capsular polysaccharide and a carrier protein, a conjugate of a serogroup C capsular polysaccharide and a carrier protein, a conjugate of a serogroup W135 capsular polysaccharide and a carrier protein, and a conjugate of a serogroup Y capsular polysaccharide and a carrier protein.

By including antigens from serogroup X and serogroup A and/or serogroup W135, compositions comprising combinations 1)-3) can provide protection against the serogroups that cause the majority of *N. meningitidis* disease in Africa. Such combinations are therefore particularly preferred. Although the addition of further antigens, e.g. the antigens from serogroups C and Y included in combination 4), may provide additional protection, the benefit of this additional protection may not outweigh the additional costs involved. Accordingly, in some embodiments of the invention, the composition does not contain an antigen from serogroup C, particularly a conjugate of a serogroup C capsular polysaccharide and a carrier protein. Similarly, in the same or other embodiments of the invention, the composition does not contain an antigen from serogroup Y, particularly a conjugate of a serogroup Y capsular polysaccharide and a carrier protein.

The further antigen(s) may comprise additional bacterial, viral or parasitic antigens. These may be selected from the following:

a saccharide antigen from *Streptococcus pneumoniae* [e.g. refs. 77-79; chapters 22 & 23 of ref. 86].

an antigen from hepatitis A virus, such as inactivated virus [e.g. 80, 81; chapter 15 of ref. 86].

an antigen from hepatitis B virus, such as the surface and/or core antigens [e.g. 81,82; chapter 16 of ref. 86].

an antigen from hepatitis C virus [e.g. 83].

an antigen from *Bordetella pertussis*, such as pertussis holotoxin (PT) and filamentous haemagglutinin (FHA)

from *B. pertussis*, optionally also in combination with pertactin and/or agglutinogens 2 and 3 [e.g. refs. 84 & 85; chapter 21 of ref. 86].

a diphtheria antigen, such as a diphtheria toxoid [e.g. chapter 13 of ref. 86].

a tetanus antigen, such as a tetanus toxoid [e.g. chapter 27 of ref. 86].

a saccharide antigen from *Haemophilus influenzae* B [e.g. chapter 14 of ref. 86]

an antigen from *Chlamydia pneumoniae* [e.g. 87, 88, 89, 90, 91, 92, 93].

an antigen from *Chlamydia trachomatis* [e.g. 94].

an antigen from *Porphyromonas gingivalis* [e.g. 95].

polio antigen(s) [e.g. 96, 97; chapter 24 of ref. 86] such as IPV.

rabies antigen(s) [e.g. 98] such as lyophilised inactivated virus [e.g. 99, RabAvert™]

measles, mumps and/or rubella antigens [e.g. chapters 19, 20 and 26 of ref. 86].

influenza antigen(s) [e.g. chapters 17 & 18 of ref. 86], such as the haemagglutinin and/or neuraminidase surface proteins.

an antigen from *Moraxella catarrhalis* [e.g. 100].

an antigen from *Streptococcus pyogenes* (group A streptococcus) [e.g. 101, 102, 103].

an antigen from *Streptococcus agalactiae* (group B streptococcus) [e.g. 64, 104-106].

an antigen from *S. epidermidis* [e.g. type I, II and/or III capsular polysaccharide obtainable from strains ATCC-31432, SE-360 and SE-10 as described in refs. 107, 108 and 109.

Where a saccharide or carbohydrate antigen is used, it is typically conjugated to a carrier in order to enhance immunogenicity. Conjugation of *H. influenzae* B, meningococcal and pneumococcal saccharide antigens is well known.

Toxic protein antigens may be detoxified where necessary (e.g. detoxification of pertussis toxin by chemical and/or genetic means [85]).

Where a diphtheria antigen is included in the composition it is typical also to include tetanus antigen and pertussis antigens. Similarly, where a tetanus antigen is included it is typical also to include diphtheria and pertussis antigens. Similarly, where a pertussis antigen is included it is typical also to include diphtheria and tetanus antigens.

Antigens may be adsorbed to an aluminium salt.

Antigens in the composition will typically be present at a concentration of at least 1 µg/ml each. In general, the concentration of any given antigen will be sufficient to elicit an immune response against that antigen.

As an alternative to using proteins antigens in the composition of the invention, nucleic acid encoding the antigen may be used [e.g. refs. 110 to 118]. Protein components of the compositions of the invention may thus be replaced by nucleic acid (usually DNA e.g. in the form of a plasmid) that encodes the protein.

In practical terms, there may be an upper limit to the number of antigens included in compositions of the invention. The number of antigens in a composition of the invention may be less than 20, less than 19, less than 18, less than 17, less than 16, less than 15, less than 14, less than 13, less than 12, less than 11, less than 10, less than 9, less than 8, less than 7, less than 6, less than 5, less than 4, or less than 3.

Pharmaceutical Compositions and Methods

The invention provides a pharmaceutical composition comprising (a) a serogroup X capsular polysaccharide, particularly in the form of a conjugate of the invention, and (b) a pharmaceutically acceptable carrier. Typical 'pharmaceutically acceptable carriers' include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [119], trehalose [120], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 121.

Compositions of the invention may be in an aqueous formulation (i.e. solutions or suspensions) or in a dried form (e.g. lyophilised). Aqueous formulations are preferred because the inventors have found that the serogroup X capsular polysaccharide is surprisingly stable in an aqueous environment. If a dried vaccine is used then it will be reconstituted into an aqueous formulation prior to injection. Lyophilisation of conjugate vaccines is known in the art e.g. the Menjugate™ product is presented in lyophilised form, whereas NeisVac-C™ and Meningitec™ are presented in aqueous form. To stabilise conjugates during lyophilisation, it may be typical to include a sugar alcohol (e.g. mannitol) or a disaccharide (e.g. sucrose or trehalose) e.g. at between 1 mg/ml and 30 mg/ml (e.g. about 25 mg/ml) in the composition. After reconstitution, these stabilisers may be present in the aqueous formulation.

Compositions may be presented in vials, or they may be presented in ready-filled syringes. The syringes may be supplied with or without needles. A syringe will include a single dose of the composition, whereas a vial may include a single dose or multiple doses.

Aqueous formulations of the invention are also suitable for reconstituting other vaccines from a lyophilised form. Where a composition of the invention is to be used for such extemporaneous reconstitution, the invention provides a kit, which may comprise two vials, or may comprise one ready-filled syringe and one vial, with the contents of the syringe being used to reactivate the contents of the vial prior to injection.

Compositions of the invention may be packaged in unit dose form or in multiple dose form. For multiple dose forms, vials are preferred to pre-filled syringes. Effective dosage volumes can be routinely established, but a typical human dose of the composition has a volume of 0.5 ml e.g. for intramuscular injection.

The pH of the composition is typically between 6 and 8, e.g. about 7. Stable pH may be maintained by the use of a buffer. Typical buffers, e.g. for use in the aqueous formulations of the invention, are phosphate salts. For example, a mixture of anhydrous dibasic sodium phosphate and monobasic sodium phosphate is typical. A suitable concentration is 10 mM anhydrous dibasic sodium phosphate and 10 mM monobasic sodium phosphate. If a composition comprises an aluminium hydroxide salt, it is typical to use a histidine buffer [122]. The composition may be sterile and/or pyrogen-free. Compositions of the invention may be isotonic with respect to humans.

Compositions of the invention are immunogenic, and are more preferably vaccine compositions. Vaccines according to the invention may either be prophylactic (i.e. to prevent infection) or therapeutic (i.e. to treat infection), but will typically be prophylactic. Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials.

Within each dose, the quantity of an individual saccharide antigen will generally be between 1-50 µg (measured as mass of saccharide) e.g. about 1 µg, about 2.5 µg, about 4 µg, about 5 µg, or about 10 µg.

*N. meningitidis* affects various areas of the body and so the compositions of the invention may be prepared in various forms. For example, the compositions may be prepared as injectables, either as aqueous solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 123 & 124]. Success with nasal administration of pneumococcal saccharides [125,126], Hib saccharides [127], MenC saccharides [128], and mixtures of Hib and MenC saccharide conjugates [129] has been reported.

Compositions of the invention may include an antimicrobial, particularly when packaged in multiple dose format.

Compositions of the invention may comprise detergent e.g. a TWEEN (polysorbate), such as TWEEN 80. Detergents are generally present at low levels e.g. <0.01%.

Compositions of the invention may include sodium salts (e.g. sodium chloride) to give tonicity. A concentration of 2-20 mg/ml, e.g. about 10±2 mg/ml or about 5±1 mg/ml (particularly about 4.25 mg) NaCl is typical.

Compositions of the invention will generally include a buffer. A phosphate buffer is typical.

Compositions of the invention will generally be administered in conjunction with other immunoregulatory agents. In particular, compositions will usually include one or more adjuvants. Such adjuvants include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 130], or mixtures of different mineral compounds (e.g. a mixture of a phosphate and a hydroxide adjuvant, optionally with an excess of the phosphate), with the compounds taking any suitable form (e.g. gel, crystalline, amorphous, etc.), and with adsorption to the salt(s) being typical. The mineral containing compositions may also be formulated as a particle of metal salt [131].

Aluminum salts may be included in vaccines of the invention such that the dose of $Al^{3+}$ is between 0.2 and 1.0 mg per dose.

A typical aluminium phosphate adjuvant is amorphous aluminium hydroxyphosphate with $PO_4/Al$ molar ratio between 0.84 and 0.92, included at 0.6 mg $Al^{3+}$/ml. Adsorption with a low dose of aluminium phosphate may be used e.g. between 50 and 100 µg $Al^{3+}$ per conjugate per dose. Where an aluminium phosphate it used and it is desired not to adsorb an antigen to the adjuvant, this is favoured by including free phosphate ions in solution (e.g. by the use of a phosphate buffer).

B. Oil Emulsions

Oil emulsion compositions suitable for use as adjuvants in the invention include squalene-water emulsions, such as MF59 (5% Squalene, 0.5% TWEEN 80, and 0.5% SPAN 85, formulated into submicron particles using a microfluidizer) [Chapter 10 of ref. 130; see also refs. 132-134]. MF59 is used as the adjuvant in the FLUAD influenza virus trivalent subunit vaccine.

Particularly useful adjuvants for use in the compositions are submicron oil-in-water emulsions. Preferred submicron oil-in-water emulsions for use herein are squalene/water emulsions optionally containing varying amounts of MTP-PE, such as a submicron oil-in-water emulsion containing 4-5% w/v squalene, 0.25-1.0% w/v TWEEN 80 (polyoxyelthylenesorbitan monooleate), and/or 0.25-1.0% SPAN 85 (sorbitan trioleate), and, optionally, N-acetylmuramyl-L-alanyl-D-isogluatminyl-L-alanine-2-(1'-2'-dipalmitoyl-s-n-glycero-3-hydroxyphosphophoryloxy)-ethylamine (MTP-PE). Submicron oil-in-water emulsions, methods of making the same and immunostimulating agents, such as muramyl peptides, for use in the compositions, are described in detail in references 132 and 135-136.

Complete Freund's adjuvant (CFA) and incomplete Freund's adjuvant (IFA) may also be used as adjuvants in the invention.

C. Saponin Formulations [Chapter 22 of Ref. 130]

Saponin formulations may also be used as adjuvants in the invention. Saponins are a heterologous group of sterol glycosides and triterpenoid glycosides that are found in the bark, leaves, stems, roots and even flowers of a wide range of plant species. Saponins isolated from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref. 137. Saponin formulations may also comprise a sterol, such as cholesterol [138].

Combinations of saponins and cholesterols can be used to form unique particles called immunostimulating complexs (ISCOMs) [chapter 23 of ref. 130]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 138-140. Optionally, the ISCOMS may be devoid of additional detergent(s) [141].

A review of the development of saponin based adjuvants can be found in refs. 142 & 143.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 144-149. Virosomes are discussed further in, for example, ref. 150

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 151. Such "small particles" of 3dMPL are small enough to be sterile filtered through a 0.22 µm membrane [151]. Other non-toxic LPS derivatives include monophosphoryl lipid A mimics, such as aminoalkyl glucosaminide phosphate derivatives e.g. RC-529 [152,153].

Lipid A derivatives include derivatives of lipid A from *Escherichia coli* such as OM-174. OM-174 is described for example in refs. 154 & 155.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 156, 157 and 158 disclose possible analog substitutions e.g. replacement of guanosine with 2'-deoxy-7-deazaguanosine. The adjuvant effect of CpG oligonucleotides is further discussed in refs. 159-164.

The CpG sequence may be directed to TLR9, such as the motif GTCGTT or TTCGTT [165]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 166-168. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 165 & 169-171.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 172 and as parenteral adjuvants in ref. 173. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 174-181. Numerical reference for amino acid substitutions is preferably based on the alignments of the A and B subunits of ADP-ribosylating toxins set forth in ref. 182, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [183], etc.) [184], interferons (e.g. interferon-γ), macrophage colony stimulating factor, and tumor necrosis factor.

G. Bioadhesives and Mucoadhesives

Bioadhesives and mucoadhesives may also be used as adjuvants in the invention. Suitable bioadhesives include esterified hyaluronic acid microspheres [185] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [186].

H. Microparticles

Microparticles may also be used as adjuvants in the invention. Microparticles (i.e. a particle of ~100 nm to ~150 µm in diameter, more preferably ~200 nm to ~30 µm in diameter, and most preferably ~500 nm to ~10 µm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref. 130)

Examples of liposome formulations suitable for use as adjuvants are described in refs. 187-189.

J. Polyoxyethylene Ether and Polyoxyethylene Ester Formulations

Adjuvants suitable for use in the invention include polyoxyethylene ethers and polyoxyethylene esters [190]. Such formulations further include polyoxyethylene sorbitan ester surfactants in combination with an octoxynol [191] as well as polyoxyethylene alkyl ethers or ester surfactants in combination with at least one additional non-ionic surfactant such as an octoxynol [192]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polvphosphazene (PCPP)

PCPP formulations are described, for example, in refs. 193 and 194.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 195 and 196.

N. Thiosemicarbazone Compounds.

Examples of thiosemicarbazone compounds, as well as methods of formulating, manufacturing, and screening for compounds all suitable for use as adjuvants in the invention include those described in ref. 197. The thiosemicarbazones are particularly effective in the stimulation of human peripheral blood mononuclear cells for the production of cytokines, such as TNF-α.

O. Tryptanthrin Compounds.

Examples of tryptanthrin compounds, as well as methods of formulating, manufacturing, and screening for compounds all suitable for use as adjuvants in the invention include those described in ref. 198. The tryptanthrin compounds are particularly effective in the stimulation of human peripheral blood mononuclear cells for the production of cytokines, such as TNF-α.

The invention may also comprise combinations of aspects of one or more of the adjuvants identified above. For example, the following combinations may be used as adjuvant compositions in the invention: (1) a saponin and an oil-in-water emulsion [199]; (2) a saponin (e.g. QS21)+a non-toxic LPS derivative (e.g. 3dMPL) [200]; (3) a saponin (e.g. QS21)+a non-toxic LPS derivative (e.g. 3dMPL)+a cholesterol; (4) a saponin (e.g. QS21)+3dMPL+IL-12 (optionally+a sterol) [201]; (5) combinations of 3dMPL with, for example, QS21 and/or oil-in-water emulsions [202]; (6) SAF, containing 10% squalane, 0.4% TWEEN 80, 5% pluronic-block polymer L121, and thr-MDP, either microfluidized into a submicron emulsion or vortexed to generate a larger particle size emulsion. (7) RIBI. adjuvant system (RAS), (RIBI Immunochem) containing 2% squalene, 0.2% TWEEN 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

Other substances that act as immunostimulating agents are disclosed in chapter 7 of ref. 130.

The use of aluminium salt adjuvants is particularly useful, and antigens are generally adsorbed to such salts. The Menjugate™ and NeisVac™ conjugates use a hydroxide adjuvant, whereas Meningitec™ uses a phosphate adjuvant. It is possible in compositions of the invention to adsorb some antigens to an aluminium hydroxide but to have other antigens in association with an aluminium phosphate. Typically, however, only a single salt is used, e.g. a hydroxide or a phosphate, but not both. Not all conjugates need to be adsorbed i.e. some or all can be free in solution.

Methods of Treatment

The invention also provides a method for raising an immune response in a mammal, comprising administering a pharmaceutical composition of the invention to the mammal. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides a composition of the invention for use as a medicament. The medicament is preferably able to raise an immune response in a mammal (i.e. it is an immunogenic composition) and is more preferably a vaccine.

The invention also provides the use of a conjugate of the invention in the manufacture of a medicament for raising an immune response in a mammal.

Preferred compositions of the invention can confer an antibody titre in a patient that is superior to the criterion for seroprotection for each antigenic component for an acceptable percentage of human subjects. Antigens with an associated antibody titre above which a host is considered to be seroconverted against the antigen are well known, and such titres are published by organisations such as WHO. Preferably more than 80% of a statistically significant sample of subjects is seroconverted, more preferably more than 90%, still more preferably more than 93% and most preferably 96-100%.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Exemplary Carrier Proteins

As discussed above, the inventors have found that the carrier proteins described in ref. 65 and ref. 66 are particularly suitable for use as a carrier molecule in the invention, especially the protein of SEQ ID NO: 9 in those documents (which is also SEQ ID NO: 9 herein).

These carrier molecules comprise a spr0096 antigen and a spr2021 antigen. Typically, the carrier molecule comprises the spr0096 antigen and the spr2021 antigen as a single polypeptide chain (a "hybrid" polypeptide). The spr0096 antigen, spr2021 antigen and the nature of the hybrid polypeptide are described in more detail below.

spr0096 Antigen

The original 'spr0096' polypeptide sequence was annotated in reference 203 as 'hypothetical protein' (see GI:15902140). For reference purposes, the amino acid sequence of full length spr0096 as found in the R6 strain is given as SEQ ID NO: 1 herein.

The spr0096 antigen of the invention comprises at least one CD4$^+$ T cell epitope. CD4$^+$ T cells help B lymphocytes to produce antibodies against antigens [204]. T-cell epitopes can be identified empirically (e.g. using PEPSCAN [205, 206] or similar methods), or they can be predicted (e.g. using the Jameson-Wolf antigenic index [207], matrix-based approaches [208], TEPITOPE [209], neural networks [210], OptiMer & EpiMer [211,212], ADEPT [213], Tsites [214], hydrophilicity [215], antigenic index [216] or the methods disclosed in reference 217, etc.).

Preferred spr0096 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These spr0096 polypeptides include variants of SEQ ID NO: 1 (e.g. SEQ ID NO: 2; see below). Preferred fragments of (b) comprise at least one CD4+ T cell epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 1 while retaining at least one CD4+ T cell epitope of SEQ ID NO: 1. Other fragments omit one or more protein domains. One suitable fragment is SEQ ID NO: 14, which omits the natural leader peptide sequence. The spr0096 antigen may consist of a single CD4+ T cell epitope from SEQ ID NO: 1.

A variant form of spr0096, with an insert near its C-terminus relative to SEQ ID NO: 1, is SEQ ID NO: 2 herein. The use of this variant for immunisation is reported in reference 218 (SEQ ID NO: 150 therein), where it is annotated as a LysM domain protein. Thus a spr0096 antigen for use with the invention may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more). These polypeptides include variants of SEQ ID NO: 2. Preferred fragments of (b) comprise at least one CD4+ T cell epitope from SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 2 while retaining at least one CD4+ T cell epitope of SEQ ID NO: 2. Other fragments omit one or more protein domains. One suitable fragment is SEQ ID NO: 15, which omits the natural leader peptide sequence. Immunogenic fragments of SEQ ID NO: 2 are identified in table 1 of reference 218. The spr0096 antigen may consist of a single CD4+ T cell epitope from SEQ ID NO: 2.

A spr0096 antigen may be used in the form of a dimer e.g. a homodimer.

spr2021 Antigen

The original 'spr2021' polypeptide sequence was annotated in reference 203 as 'General stress protein GSP-781' (see GI:15904062). For reference purposes, the amino acid sequence of full length spr2021 as found in the R6 strain is given as SEQ ID NO: 3 herein.

The spr2021 antigen of the invention comprises at least one CD4+ T cell epitope.

Preferred spr2021 antigens for use with the invention comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These spr2021 polypeptides include variants of SEQ ID NO: 3. Preferred fragments of (b) comprise at least one CD4+ T cell epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one CD4+ T cell epitope of SEQ ID NO: 3. Other fragments omit one or more protein domains. One suitable fragment is SEQ ID NO: 4, which omits the natural leader peptide sequence. The spr0096 antigen may consist of a single CD4+ T cell epitope from SEQ ID NO: 3.

Reference 218 annotates spr2021 as a secreted 45 kDa protein with homology to GbpB and discloses its use as an immunogen (SEQ ID NO: 243 therein; SP2216). Immunogenic fragments of spr2021 are identified in table 1 of reference 218 (page 73). Another useful fragment of spr2021 is disclosed as SEQ ID NO: 1 of reference 219 (amino acids 28-278 of SEQ ID NO: 3 herein).

Hybrid Polypeptide

Typically, the spr0096 antigen and spr2021 antigen are expressed as a single polypeptide chain (a 'hybrid' polypeptide). Hybrid polypeptides can be represented by the formula $NH_2$-A-{-X-L-}$_n$-B—COOH, wherein: A is an optional N-terminal amino acid sequence; B is an optional C-terminal amino acid sequence; n is an integer of 2 or more (e.g. 2, 3, 4, 5, 6, etc.); each X is an amino acid sequence of an spr0096 antigen or an spr2021 antigen (as described above), wherein at least one X is an spr0096 antigen and at least one X is an spr2021 antigen; and L is an optional linker amino acid sequence. Usually n is 2. When n is 2, $X_1$ is usually an spr0096 antigen and $X_2$ is usually an spr2021 antigen. When n is more than 2, each spr0096 antigen (when more than one is present) may be the same or different and each spr2021 antigen (when more than one is present) may be the same or different.

The spr0096 antigen or spr2021 antigen that is the amino acid sequence of each X is as defined above. Where these antigens are defined in terms of (a) having 50% or more identity (e.g. 60%, 65%, 70%, 75%, 80%, 85%, 90%, 91%, 92%, 93%, 94%, 95%, 96%, 97%, 98%, 99%, 99.5% or more) to a given sequence; and/or (b) comprising a fragment of at least 'n' consecutive amino acids of a given sequence, wherein 'n' is 7 or more (e.g. 8, 10, 12, 14, 16, 18, 20, 25, 30, 35, 40, 50, 60, 70, 80, 90, 100, 150, 200, 250 or more), the level of identity in (a) and the value of 'n' in (b) may be the same for each X.

The leader peptide sequence in the wild-type form of each —X— moiety may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of {—X-L-}, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more), and histidine tags (i.e. $His_n$ where n=3, 4, 5, 6, 7, 8, 9, 10 or more). Other suitable linker amino acid sequences will be apparent to those skilled in the art. A useful linker is GSGGGG (SEQ ID NO:5) or GSGSGGGG (SEQ ID NO:6), with the Gly-Ser dipeptide being formed from a BamHI restriction site, thus aiding cloning and manipulation, and the $(Gly)_4$ tetrapeptide being a typical poly-glycine linker. Other suitable linkers, particularly for use as the final $L_n$ are a Leu-Glu dipeptide or SEQ ID NO: 7.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more). Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include sequences to direct protein trafficking, short peptide sequences which facilitate cloning or purification (e.g. comprising histidine tags i.e. $His_n$ where n=3, 4, 5, 6, 7, 8, 9, 10 or more, such as SEQ ID NO: 8), or sequences which enhance protein stability. Other suitable C-terminal amino acid sequences will be apparent to those skilled in the art.

Examples of hybrids include polypeptides that comprise an amino acid sequence of spr0096-spr2021 (e.g. SEQ ID NO: 9) or spr2021-spr0096 (e.g. SEQ ID NO: 10). The hybrid may also comprise an amino acid sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9 or 10. Typically, the hybrid comprises an amino acid sequence of SEQ ID NO: 9. The hybrid may also comprise an amino acid sequence having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9.

In particular embodiments, the carrier molecule comprises (a) one or more (e.g. 1, 2, 3, 4, 5, etc.) $CD4^+$ T cell epitopes from SEQ ID NO: 2; and (b) one or more (e.g. 1, 2, 3, 4, 5, etc.) $CD4^+$ T cell epitopes from SEQ ID NO: 3.

Method for Assaying a Sample

In a particular aspect, the invention provides a method for assaying a sample suspected to contain serogroup X capsular polysaccharide, comprising the steps of: (i) hydrolysing any serogroup X capsular polysaccharide in the sample, to give a hydrolysate; (ii) subjecting the hydrolysate to liquid chromatography; and (iii) detecting any glucosamine-4-phosphate separated in step (ii).

The method can be used for quantifying serogroup X capsular polysaccharide in the sample. In this way, it is possible to determine the concentration of the polysaccharide in the sample. Typically, the quantification involves comparison with a N-acetylglucosamine-4-phosphate standard. However, other standards may be used, including glucosamine-6-phosphate.

Although the method has been developed for serogroup X capsular polysaccharide, it is suitable for any substance with glucosamine-4-phosphate in its structure, e.g. bacterial lipid A. Accordingly, the invention also provides a method for assaying a sample suspected to contain a substance with glucosamine-4-phosphate in its structure, comprising the steps of: (i) hydrolysing any substance with glucosamine-4-phosphate in its structure in the sample, to give a hydrolysate; (ii) subjecting the hydrolysate to liquid chromatography; and (iii) detecting any glucosamine-4-phosphate separated in step (ii).

Sample

The sample is typically a vaccine, e.g. when the method is used for polysaccharide quantification in the characterization of a vaccine product. However, the method can also be used as an in-process assay during vaccine manufacture. In these embodiments, the sample will be a process intermediate from the manufacturing process. The method of the invention is capable of quantifying very low concentrations of serogroup X capsular polysaccharide ($\geq 0.5$ µg/ml) and is therefore suitable for assaying serogroup X capsular polysaccharide in small samples, e.g. taken in-process during a manufacturing process. The method is also specific for serogroup X capsular polysaccharide, even when impurities are present. The sample may therefore be a fermentation broth, or a supernatant taken from a fermentation broth.

The sample may contain free (unconjugated) serogroup X capsular polysaccharide and/or conjugated serogroup X capsular polysaccharide. Thus the method may be used to assay polysaccharide prepared from a bacterium, polysaccharide after purification, polysaccharide prior to conjugation, and/or polysaccharide after conjugation.

In a sample containing conjugated serogroup X capsular polysaccharide, a comparison of levels of free polysaccharide to the total polysaccharide in a sample (i.e. the ratio of unconjugated polysaccharide:(unconjugated+conjugated) polysaccharide) can be used to determine stability. High levels of unconjugated polysaccharide are undesirable. A time-series of such assays can reveal if a conjugate is stable e.g. during storage. The level of free polysaccharide can also be used to check if a conjugation reaction has gone to completion.

The sample will typically be aqueous, but may have been reconstituted into aqueous form from a dried form e.g. from a lyophilisate. Thus the sample may contain lyophilisation stabilizers. These stabilizers include substances such as sugar alcohols (e.g. mannitol, etc.), disaccharides (e.g. sucrose, trehalose, etc.), and other simple saccharides. An advantage of the methods of the invention is that they can assay serogroup X capsular polysaccharide against a background of impurities, without requiring any pre-separation of the polysaccharide and the impurities.

The sample may be diluted prior to analysis. After analysis, the level of polysaccharide in the sample can then be related to the level in the original undiluted material. Dilution is useful, for example, to ensure that analysis of a sample gives a result within a desired portion of a calibration curve. In addition to serogroup X capsular polysaccharide, the sample may contain other bacterial capsular saccharides e.g. from *Haemophilus influenzae* type B, from other meningococcal serogroups (e.g. A, C, W135 and/or Y), from *Streptococcus pneumoniae*, etc.

Samples may also include other components, such as non-antigen components often found in vaccines. For example, these may include carriers, adjuvants, excipients, buffers, etc., as described above.

In some situations, it is useful to spike the sample with a known amount of the analyte in question e.g. to add a known quantity of serogroup X capsular polysaccharide, either in conjugated or unconjugated form. Spiking studies can be useful for calibration, and for studying sensitivity, variability, recovery, etc.

Hydrolysis

The method involves hydrolysis of the serogroup X capsular polysaccharide. Typical hydrolysis methods involve acid hydrolysis e.g. using trifluoroacetic acid (TFA). The inventors have found that particularly effective conditions are treatment with 2M TFA for between 2 and 3 (e.g. 2.5) hours at 100° C. These conditions allow good release of the polysaccharide's monomer subunits, without their degradation. However, shorter or longer treatments, e.g. for between 1 and 6 hours, are also possible.

Total serogroup X capsular polysaccharide can be prepared from a sample including conjugated polysaccharide by subjecting the whole sample to hydrolysis, as described above. If measurement of only conjugated or unconjugated serogroup X capsular polysaccharide is desired, however, then conjugated and unconjugated polysaccharide should be separated from each other prior to hydrolysis. Suitable separation techniques include selective precipitation, size-based methods, solid-phase extraction [220], etc.

Liquid Chromatography

The results of serogroup X capsular polysaccharide hydrolysis are analysed by liquid chromatography. Thus the methods of the invention will typically utilize a liquid chromatography column, and will involve analysing the output of such a column.

Various liquid chromatography columns can be used, but the invention will typically be used with high performance liquid chromatography (HPLC). The invention is particularly useful for analysing the results of separation by high performance anion exchange chromatography (HPAEC) or by high performance cation exchange chromatography (HPCEC). HPAEC is a common technique used for saccharide characterisation, often in combination with pulsed amperometric detection (PAD) [221,222] to detect and quantify the polysaccharide. Suitable HPAEC-PAD systems are provided by DIONEX Corporation (Sunnyvale, Calif.) e.g. the BIOLC system. In these systems, the eluate from a HPAEC column is analysed using PAD i.e. based on electrical current. At suitable (high) pH, carbohydrates can be electrocatalytically oxidised at the surface of electrodes by applying a positive potential. The current generated is this way is proportional to the carbohydrate concentration, allowing detection and quantification of the carbohydrate by amperometry. Compared with simple amperometric detection, PAD intersperses short pulses of a cleaning and regeneration potential with the standard detecting potential, thereby avoiding difficulties that arise when oxidation products of analytes foul the electrodes.

Non-amperometric methods can be combined with PAD for analyzing eluates e.g. see ref. 223.

Thus the hydrolysed serogroup X capsular polysaccharide can be subjected to HPAEC for separation and the separated materials can be detected and, optionally, quantified by PAD. As shown in the examples below, HPAEC-PAD can separate hydrolysed glucosamine-4-phosphate residues from other background materials in a sample.

Preferred columns are those that spontaneously retain saccharides such that they have to be eluted from the column. Elution from the chromatography column can be an isocratic elution or a gradient elution. Eluents including hydroxide and/or acetate salts are typical eluents used during HPAEC-PAD analysis of saccharides. It is also possible, however, to use anions such as nitrate, chloride, etc. Sodium salts are typically used. For eluting analytes from AEC columns then the eluent will generally be basic e.g. the pH will be $>8$, $>9$, $>10$, $>11$, $>12$, $>13$, etc. Hydroxide salts (e.g. NaOH) can be used to achieve the desired pH.

Eluates may be subjected to chemical suppression of hydroxide ions, particularly where the ions interfere with an analytical detection technique that is being used. A micromembrane suppressor can conveniently be used, such as the MMS products from DIONEX. The 'MMS III' product uses continuous chemical suppression to enhance analyte conductivities while decreasing eluent conductivity, and enables direct conductivity detection with ion-exchange applications using isocratic or gradient elution over wide concentration ranges.

Suitable HPAEC columns for use with the invention are the "CARBOPAC" columns marketed by DIONEX, such as the PA1 [10 μm diameter polystyrene substrate 2% crosslinked with divinylbenzene, agglomerated with 500 nm MicroBead quaternary ammonium functionalized latex (5% crosslinked)], PA100, PA20, PA10 [10 .mu.m diameter ethylvinylbenzene substrate 55% crosslinked with divinylbenzene, agglomerated with 460 nm MicroBead difunctional quaternary ammonium ion (5% crosslinked)], PA200 or MA1 columns.

Analytical HPAEC columns can be used in conjunction with pre-columns and/or trap columns. For instance, a PA10 analytical column can be used in conjunction with an inline PA10 guard column, and/or an inline trap (pre-treatment) column. Such columns can remove materials that would otherwise interfere with analyses e.g. an "AMINOTRAP" column can remove amino acids prior to saccharide analysis. Borate traps can also be used. AminoTrapA typical AMINOTRAP resin has a 10 .μm diameter substrate (ethylvinylbenzene 55% crosslinked with divinylbenzene) grafted with difunctional quaternary ammonium anion exchange sites, whereas a typical BORATETRAP has a 20 μm diameter high capacity resin with very high selectivity for borate.

The PA1 and PA10 columns are both anion-exchange columns designed to be used with PAD to deliver high resolution separations of mono- and disaccharides, and the resins in both are 10 μm diameter nonporous beads covered with a fine latex of functionalized MicroBeads. Their pellicular resin structure permits excellent mass transfer, resulting in high resolution chromatography and rapid re-equilibration. Whereas PA1 is an all-purpose column suitable for determining monosaccharides and disaccharides in a variety of matrices, and is the column of choice for high resolution separations of linear polysaccharides, PA10 is optimized to determine the amino, neutral, and acidic monosaccharides that are found in the carbohydrate moieties of mammalian glycoproteins. The main difference between the PA1 and PA10 columns is that the resin in PA1 is polystyrene 2% crosslinked with divinylbenzene, but in PA10 it is ethylvinylbenzene 55% crosslinked with divinylbenzene.

To date, the most preferred HPAEC separation method for serogroup X capsular polysaccharide involves a CARBOPAC PA1 column (4×250 mm) combined with a Guard PA1 pre-column (4×50 mm).

After elution and detection, the invention may include the further step of determining a characteristic of any serogroup X capsular polysaccharide that was identified in the sample e.g. its DP (typically an average DP), its molecular weight, its purity, etc.

Preparation of N-acetylglucosamine-4-phosphate

In a further aspect, the invention provides processes and reagents useful for preparing N-acetylglucosamine-4-phosphate. As discussed above, this compound can be used as an analytical standard in the method for assaying serogroup X capsular polysaccharide.

In a first embodiment of this aspect, the invention provides a process comprising N-deprotecting a compound of formula A and N-acylating the deprotected compound to give a compound of formula B;

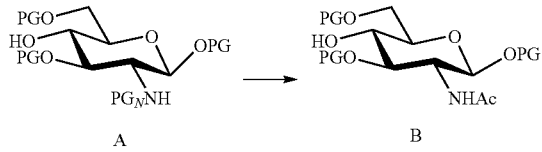

wherein PG is an oxygen protecting group; $PG_N$ is a nitrogen protecting group and all the PG groups are the same. PG and $PG_N$ may be any suitable protecting group, for example as described in reference 224.

In a second embodiment of this aspect, the invention provides a process for introducing an organophosphate group into a compound of formula B to give a compound of formula C:

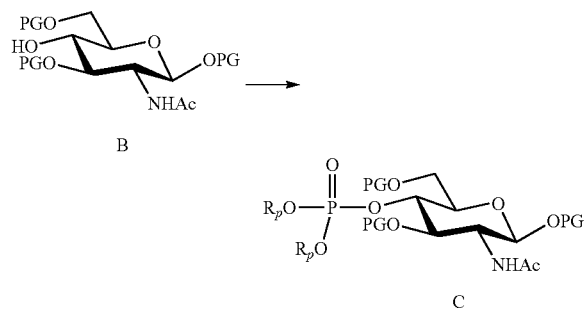

wherein both $R_P$ groups are the same and $R_P$ is either H or an arylmethyl phosphate protecting group, for example as described in reference 224; or the $R_P$ groups are joined together to form a single arylmethyl protecting group, for example o-xylenyl. PG is as defined above and all the PG groups are the same. Where $R_P$ is H, the compound of formula B is typically reacted with a phosphorylating reagent and an oxidising agent. The phosphorylating agent may be salicyl chlorophosphite, typically in the presence of pyridine and pivaloyl chloride. The phosphorylating agent may also be $PCl_3$ followed by water or aqueous $NaHCO_3$. The oxidising agent may be $I_2$ or mCPBA, typically $I_2$. Where the $R_P$ groups are joined together to form a single protecting group, the compound of formula B is typically reacted with an o-xylene containing organophosphorus reagent and then an oxidising agent. The o-xylene containing organophosphorus reagent is typically a phosphoramidite such as N-diethyl-1,5-dihydro-3H-2,3,4-benzodioxaphosphine-3-amine. The oxidising agent may be $I_2$ or mCPBA, typically mCPBA. Where the $R_P$ groups are not joined together to form a single protecting group, the compound of formula B is typically reacted with a pyrophosphate reagent containing the $R_P$ groups. A suitable pyrophosphate reagent is tetrabenzylpyrophospate, in which case $R_P$ is a benzyl group.

In a third embodiment of this aspect, the invention provides a process comprising deprotecting a compound of formula C to give N-acetylglucosamine-4-phosphate:

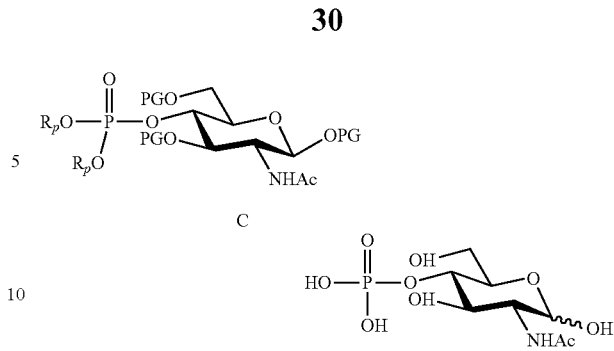

PG and $R_P$ are as defined above and all PG groups are the same. Typically, when $R_P$ is a phosphate protecting group, all the PG groups and the $R_P$ group are removed in the same step, for example by hydrogenolysis.

In further embodiments of this aspect, the invention provides a process comprising the first embodiment followed by the second embodiment; the second embodiment followed by the third embodiment and the first embodiment followed by the second embodiment followed by the third embodiment. Where these embodiments include the first embodiment, the first embodiment may be preceded by the further embodiment described below.

In a further embodiment of this aspect, the invention provides a process for making a compound of formula A above, the process comprising reducing a compound of formula Z to give a compound of formula A':

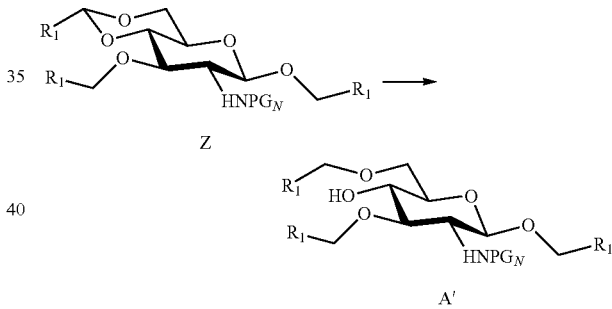

wherein $R_1$ is phenyl or phenyl substituted with one or more groups selected from alkyl, such as methyl or ethyl; O-alkyl, such as O-methyl; and nitro, such that the $R_1CH_2$— moiety in formula A' is a substituted or unsubstituted benzyl ether oxygen protecting group. The protecting group may for example be any suitable protecting group described in reference 224. In particular, the protecting group may be benzyl, p-methoxybenzyl, 3,4-dimethoxybenzyl, 2,6-dimethoxybenzyl, o-nitrobenzyl, p-nitrobenzyl, and is typically benzyl. $PG_N$ is a nitrogen protecting group as defined above. Typical $PG_N$ groups are phthalimide; carbamates such as Boc and Fmoc; nosyl, tosyl and mesyl. Particularly, $PG_N$ is phthalimide. Typically, the reaction comprises reacting a compound of formula Z, wherein $R_1$ is phenyl and $PG_N$ is a pthalimide group, with a boron containing compound and a Lewis acid in an organic solvent to give a compound of formula A'. The boron containing compound may be a borohydirde reagent such as trialkylaminoborane, particularly triethylaminoborane or trimethylaminoborane, and is typically trimethylaminoborane. The Lewis acid may be $AlCl_3$ or a boron containing Lewis acid, such as a boron trifluoride complex, and is typically $BF_3.Et_2O$. The organic solvent may be a chlorinated organic solvent, for example CHCl₃ or CH₂Cl₂ or a non-chlorinated solvent, and is typically acetonitrile. The reaction may be carried out in a temperature range of from about −10 to about 10° C., from about −5 to about 5° C., typically at about 0° C.

An example of the first embodiment of this aspect comprises step i) N-deprotecting a compound of formula A' and step ii) N-acylating the deprotected compound to give a compound of formula B':

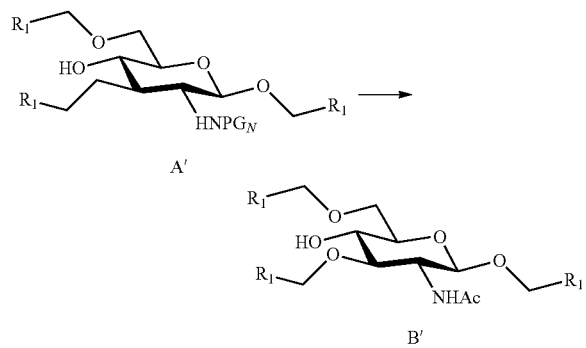

A'

B' wherein $R_1$ and $PG_N$ are as defined above. Typically, the reaction comprises reacting a compound of formula A' wherein $PG_N$ is phthalimide in step i) with 1,2-diaminoethane in an alcoholic solvent such as MeOH or EtOH, typically EtOH. Step i) is usually carried out between room temperature and the reflux point of the solvent, for example at a temperature of about 25° C. or more, from about 25 to about 80° C., from about 35 to about 80° C., from about 45 to about 80° C., from about 55 to about 80° C., from about 65 to about 80° C., from about 75 to about 80° C. typically about 80° C. or about the refluxing point of the solvent. Step ii) includes adding an acylating agent. The acylating agent may be any suitable acylating agent, typically Ac₂O with an amine base such as pyridine or triethylamine or imidazole. Alternatively the acylating agent may be about a 4:1 mixture of EtOH:Ac₂O. Step ii) may be carried out at about room temperature, for example at about 25° C. Typically there is no purification step between steps i) and ii), for example only solvent from step i) is removed before step ii) performed.

An example of the second embodiment of this aspect comprises introducing an organophosphate group into a compound of formula B' to give a compound of formula C':

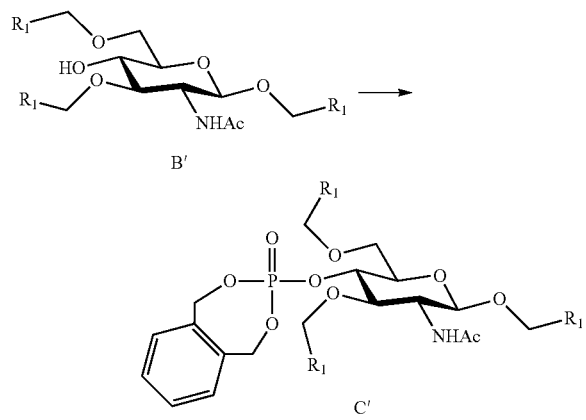

B'

C' wherein $R_1$ is as defined above. Typically, the compound of formula B' is first reacted with an o-xylene containing organophosphorus reagent, e.g. a phosphoramidite such as N-diethyl-1,5-dihydro-3H-2,3,4-benzodioxaphosphine-3-amine, in the presence of an amine base, typically 1H-tetrazole, in an organic solvent such as THF or CH₂Cl₂, typically CH₂Cl₂. An oxidising agent, such as I₂ in pyridine and water or mCPBA, is then added. The mCPBA is usually used at a temperature of from about −20° C. to about 20° C., from about −15° C. to about 15° C., from about −10° C. to about 10° C., from about −5° C. to about 5° C., and typically about 0° C. The mCPBA is usually added to the same reaction solvent as was used in the first step. The completion of the first step may be detected, for example by TLC analysis, before the mCPBA is added.

A further example of the second embodiment of this aspect comprises introducing an organophosphate group into a compound of formula B' to give a compound of formula C'':

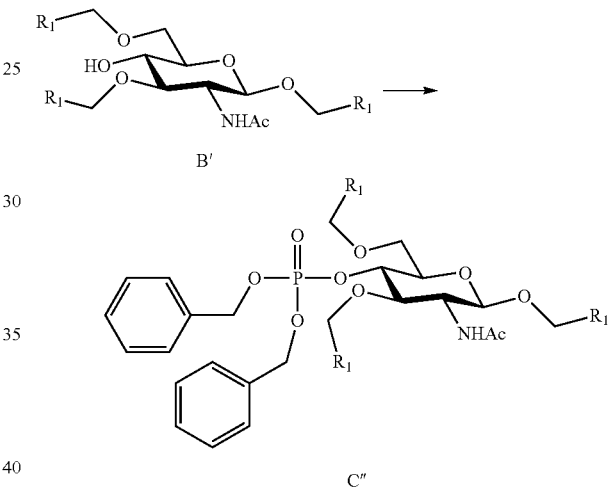

B'

C'' wherein $R_1$ is as defined above. Typically, the compound of formula B' is reacted with a pyrophosphate reagent, e.g. tetrabenzylpyrophosphate. The reaction is carried out in the presence of a base, suitable bases are lithium amides such as LDA or LiHMDS. The reaction is carried out in an organic solvent, for example a chlorinated solvent such as CH₂Cl₂ or an ether solvent, typically diethyl ether or THF. Typically, the reaction is carried out below about 0° C., for example about −10° C., about −20° C., about −30° C., about −40° C., about −50° C., about −60° C., about −70° C., suitably about −80° C. then about −30° C.

A further example of the second embodiment of this aspect comprises introducing an organophosphate group into a compound of formula B' to give a compound of formula C''':

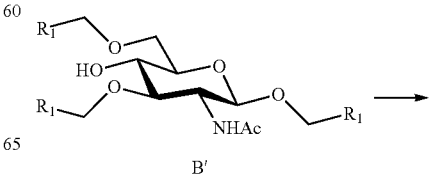

B'

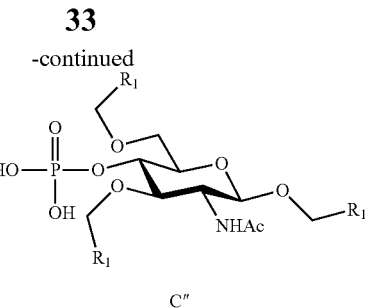

C'' wherein $R_1$ is as defined above. Typically, the compound of formula B' is phosphorylated with a suitable phosphorylating reagent and oxidising agent. Typical phosphorylating reagents are salicyl chlorophosphite or $PCl_3$ and water or aqueous $NaHCO_3$. When the phosphorylating agent is salicyl chlorophosphite, the reaction is typically carried out in a pyridine solvent and pivaloyl chloride is typically present. The reaction is usually carried out at room temperature, for example about 25° C. An oxidising agent such as $I_2$ in pyridine and water, or mCPBA is then added, typically $I_2$. The reaction is typically cooled to below about 0° C. before addition of the oxidant, for example to about −10° C., about −20° C., about −30° C., about −40° C., about −50° C., typically about −40° C. Oxidation is typically completed at a temperature of about 0° C. The $I_2$ is typically added as a solution in pyridine/water. The concentration of the solution is typically about 0.1 to 1 M, about 0.2 to 0.9 M, about 0.3 to 0.8 M, about 0.4 to 0.7 M, suitably about 0.5M. The ratio of pyridine to water is typically about 10:1 to 30:1, about 12:1 to about 28:1, about 14:1 to about 26:1 about 16:1 to about 24:1, about 18:1 to about 22:1, suitably about 19:1. The oxidant is usually added to the same reaction solvent as was used in the first step. The completion of the first step may be detected, for example by TLC analysis, before the oxidant is added. The compound of formula C''' is usually isolated as a salt, typically the di-triethylammonium salt.

When the phosphorylating agent is $PCl_3$ and water or aqueous $NaHCO_3$, the reaction is typically carried out in an organic solvent such as MeCN. Water or aqueous $NaHCO_3$ is added after $PCl_3$, suitably at room temperature. An oxidising agent such as $I_2$ or mCPBA is then added, typically $I_2$. Usually, the solvents are removed before the addition of the oxidant and a new solvent is added. The new solvent is typically a mixture of pyridine and triethylamine. The pyridine to triethylamine ratio is typically about 2:1 to about 8:1, suitably about 4:1. $I_2$ is typically added as a solution in pyridine water. The concentration of the solution is typically about 0.1 to 1 M, about 0.2 to 0.9M, about 0.3 to 0.8 M, suitably about 0.4M. The compound of formula C''' is usually isolated as a salt, typically the di-triethylammonium salt.

An example of the third embodiment of this aspect comprises deprotecting, typically by hydrogenolysis, a compound of formula C' to give N-acetylglucosamine-4-phosphate:

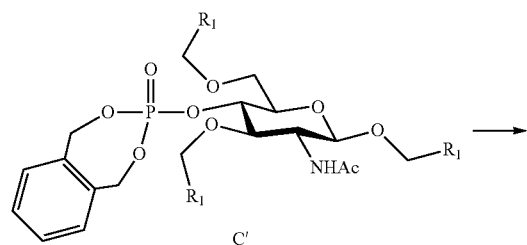

C'

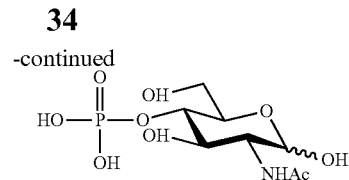

wherein $R_1$ is as defined above. Typically, the compound of formula C' is reacted with $H_2$ in the presence of a palladium catalyst such as 10% Pd/C or Pearlman's catalyst $Pd(OH)_2/C$, in an alcoholic solvent, for example MeOH or EtOH, and typically MeOH. The reaction is usually carried out at a pressure of from about 1 to about 5 atm, from about 1 to about 4 atm, from about 1 to about 3 atm, from about to about 2 atm, typically about 1 atm.

A further example of the third embodiment of this aspect comprises deprotecting, typically by hydrogenolysis, a compound of formula C'' to give N-acetylglucosamine-4-phosphate:

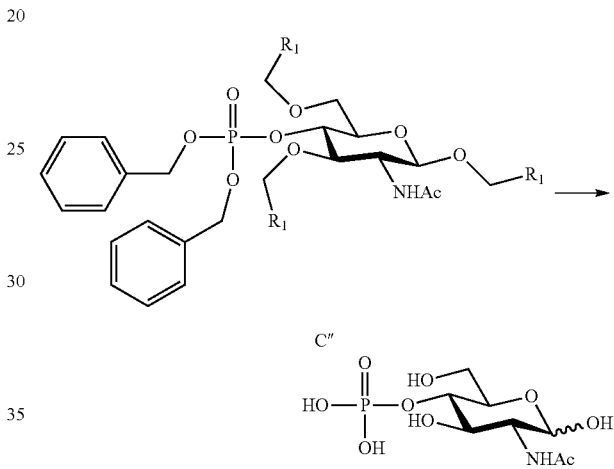

wherein $R_1$ is as defined above. Typically, the compound of formula C'' is reacted with $H_2$ in the presence of a palladium catalyst such as 10% Pd/C or Pearlman's catalyst $Pd(OH)_2/C$, in an alcoholic solvent, for example MeOH or EtOH, and typically MeOH. The reaction is usually carried out at a pressure of from about 1 to about 5 atm, from about 1 to about 4 atm, from about 1 to about 3 atm, from about to about 2 atm, typically about 1 atm.

A further example of the third embodiment of this aspect comprises deprotecting, typically by hydrogenolysis, a compound of formula C''', or the di-triethylammonium salt thereof, to give N-acetylglucosamine-4-phosphate:

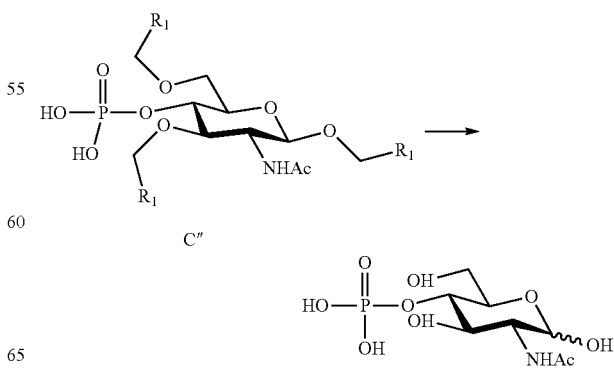

wherein $R_1$ is as defined above. Typically, the compound of formula C''' is reacted with $H_2$ in the presence of a palladium catalyst such as 10% Pd/C or Pearlman's catalyst $Pd(OH)_2$/C, in an alcoholic solvent, for example MeOH or EtOH, and typically MeOH. The reaction is usually carried out at a pressure of from about 1 to about 5 atm, from about 1 to about 4 atm, from about 1 to about 3 atm, from about to about 2 atm, typically about 1 atm.

The N-acetylglucosamine-4-phosphate may be purified, for example by crystallisation, or more typically chromatography, particularly chromotography using a hydrophobically modified silica stationary phase.

The invention also provides compounds and intermediates of the processes of this aspect, in particular, a compound of formula C, and more particularly a compound of formula C', C'' and C'''.

In a further embodiment, the process of this aspect may be as follows:

[Scheme showing compounds 1 through 6:
1: glucosamine hydrochloride (HO, HO, HO, OH, $NH_2$·HCl) → a →
2: benzylidene-protected sugar (Ph, O, O, BnO, OBn, NPhth) → b →
3: (BnO, HO, BnO, OBn, NPhth) → c →
4: (BnO, HO, BnO, OBn, NHAc) → d →
5: cyclic benzyl phosphate intermediate (BnO, BnO, OBn, NHAc with xylylene phosphate) → e →
6: N-acetylglucosamine-4-phosphate (HO-P(O)(OH)-O, HO, HO, OH, NHAc)]

Suitable reaction conditions for this embodiment are provided in the section "Modes for Carrying out the Invention" below (e.g. in Scheme 1).

General

The practice of the present invention will employ, unless otherwise indicated, conventional methods of chemistry, biochemistry, molecular biology, immunology and pharmacology, within the skill of the art. Such techniques are explained fully in the literature. See, e.g., references 225-232, etc.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed.

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

Where the invention provides a process involving multiple sequential steps, the invention can also provide a process involving less than the total number of steps. Similarly, where a starting polysaccharide material is already partially processed then the invention encompasses processes involving only the later steps of a method. These different steps can be performed at very different times by different people in different places (e.g. in different countries).

It will be appreciated that sugar rings can exist in open and closed form and that, whilst closed forms are shown in structural formulae herein, open forms are also encompassed by the invention. Similarly, it will be appreciated that sugars can exist in pyranose and furanose forms and that, whilst pyranose forms are shown in structural formulae herein, furanose forms are also encompassed. Different anomeric forms of sugars are also encompassed.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref. 233. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 234.

PARTICULAR EMBODIMENTS OF THE INVENTION

Particular embodiments of the invention include:
1. A conjugate of a *Neisseria meningitidis* serogroup X capsular polysaccharide and a carrier molecule.

2. The conjugate of embodiment 1, wherein the conjugate is obtainable by a process comprising the steps of: (a) oxidising a primary hydroxyl group in the capsular polysaccharide, to give an oxidised polysaccharide with an aldehyde group; and (b) coupling the oxidised polysaccharide to a carrier molecule via the aldehyde group, thereby giving the conjugate.

3. The conjugate of embodiment 2, where the oxidation in step (a) is of the primary hydroxyl group on between 1-10% of the residues in the capsular polysaccharide.

4. The conjugate of embodiment 3, where the oxidation is of the primary hydroxyl group on between 4-8% of the residues in the capsular polysaccharide.

5. The conjugate of any of embodiments 2-4, where the oxidation in step (a) is TEMPO-mediated oxidation.

6. The conjugate of any of embodiments 2-5, where the coupling in step (b) is direct.

7. The conjugate of embodiment 6, wherein the coupling in step (b) is by reductive amination between the aldehyde group and a primary amine group on the carrier molecule.

8. The conjugate of embodiment 1, wherein the conjugate is obtainable by a process comprising the steps of: (a) reductive amination of the reducing terminus of the capsular polysaccharide, to give a modified polysaccharide with a primary amine group bonded to the C-1 atom of the terminal subunit by a covalent bond; and (b) coupling the modified polysaccharide to a carrier molecule via the primary amine group, thereby giving the conjugate.

9. The conjugate of embodiment 8, where the coupling in step (b) is via a linker.

10. The conjugate of embodiment 1, wherein the conjugate is obtainable by a process comprising the steps of: (a) reduction of the reducing terminus of the capsular polysaccharide, to give a modified polysaccharide with two vicinal hydroxyl groups at that terminus; (b) oxidative cleavage of the vicinal hydroxyl groups, to give a further modified polysaccharide with an aldehyde group at the terminus; (c) reductive amination of the aldehyde group, to give a further modified polysaccharide with a primary amine group at the terminus and (d) coupling the further modified polysaccharide to a carrier molecule via the primary amine group, thereby giving the conjugate.

11. The conjugate of embodiment 10, wherein the primary amine group is bonded to the C-5 atom of the terminal subunit by a covalent bond.

12. The conjugate of embodiment 10, wherein the reductive amination in step (c) is between the aldehyde group and a terminal primary amine group of a bifunctional linker of the formula $X_1$-L-$X_2$, where $X_1$ comprises the terminal primary amine group; $X_2$ comprises a further terminal primary amine group; and L is a linking moiety.

13. The conjugate of embodiment 12, wherein the $X_1$ and $X_2$ groups are both —NHNH$_2$.

14. The conjugate of any of embodiments 10-13, where the coupling in step (d) is via a linker.

15. The conjugate of embodiment 9 or 14, wherein the coupling is via a bifunctional linker with a first group for coupling to the primary amine group and a second group for coupling to an amine in the carrier molecule.

16. The conjugate of embodiment 15, wherein the bifunctional linker is a homobifunctional linker of the formula X-L-X, where the two X groups are the same as each other and can react with the primary amines; and where L is a linking moiety in the linker.

17. The conjugate of embodiment 16, wherein the X group is N-oxysuccinimide.

18. The conjugate of any of embodiments 12, 13, 16 or 17, wherein L has formula -L'-$L^2$-L'-, where L' is carbonyl.

19. The conjugate of embodiment 18, wherein $L^2$ is —(CH$_2$)$_4$—.

20. The conjugate of any preceding embodiment, wherein the capsular polysaccharide is an oligosaccharide.

21. The conjugate of embodiment 20, wherein the oligosaccharide has a degree of polymerisation between 60 and 100 or between 10 and 20.

22. The conjugate of any preceding embodiment, wherein the carrier molecule is a diphtheria or tetanus toxoid, CRM197 or protein D.

23. The conjugate of any of embodiments 1-21, wherein the carrier molecule comprises a spr0096 antigen and a spr2021 antigen.

24. The conjugate of embodiment 23, wherein the spr0096 antigen comprises an amino acid sequence having 50% or more identity to SEQ ID NO: 1 or SEQ ID NO: 2.

25. The conjugate according to embodiment 23 or embodiment 24, wherein the spr2021 antigen comprises an amino acid sequence having 50% or more identity to SEQ ID NO: 3.

26. The conjugate according to any of embodiments 23-25, wherein the carrier molecule comprises the spr0096 antigen and the spr2021 antigen as a single polypeptide chain.

27. The conjugate according to embodiment 26, wherein the polypeptide chain is of the formula NH$_2$-A-{-X-L-}$_n$-B—COOH, wherein: A is an optional N terminal amino acid sequence; B is an optional C terminal amino acid sequence; n is an integer of 2 or more; each X is an amino acid sequence of an spr0096 antigen or an spr2021 antigen, wherein at least one X is an spr0096 antigen and at least one X is an spr2021 antigen; and L is an optional linker amino acid sequence.

28. The conjugate according to embodiment 27, wherein n is 2.

29. The conjugate according to embodiment 28, wherein $X_1$ is an spr0096 antigen and $X_2$ is an spr2021 antigen.

30. The conjugate according to embodiment 29, wherein the polypeptide chain comprises an amino acid sequence having 50% or more identity to SEQ ID NO: 9, particularly an amino acid sequence of SEQ ID NO: 9.

31. An immunogenic composition comprising a serogroup X capsular polysaccharide, particularly in the form of a conjugate as defined in any preceding embodiment.

32. The immunogenic composition of embodiment 31, further comprising one or more further antigens.

33. The immunogenic composition of embodiment 31 or embodiment 32, further comprising a serogroup A capsular polysaccharide.

34. The immunogenic composition of embodiment 33, wherein the serogroup A capsular polysaccharide is conjugated to a carrier molecule.

35. The immunogenic composition of any of embodiments 31-34, further comprising a serogroup W135 capsular polysaccharide.

36. The immunogenic composition of embodiment 35, wherein the composition comprises a serogroup A capsular polysaccharide conjugated to a carrier molecule.

37. The immunogenic composition of embodiment 35 or embodiment 36, wherein the serogroup W135 capsular polysaccharide is conjugated to a carrier molecule.

38. The composition of embodiment 34, 36 or 37, wherein the carrier molecule is as defined in embodiment 22.

39. The immunogenic composition of any of embodiments 31-38, further comprising a serogroup C capsular polysaccharide.

40. The immunogenic composition of any of embodiments 31-39, further comprising a serogroup Y capsular polysaccharide.
41. The immunogenic composition of embodiment 39 or embodiment 40, wherein the capsular polysaccharide is conjugated to a carrier molecule.
42. The composition of embodiment 41, wherein the carrier molecule is as defined in embodiment 22.
43. The immunogenic composition of any of embodiments 31-42, wherein the composition is in an aqueous formulation.
44. A vaccine comprising the immunogenic composition of any of embodiments 31-43.
45. A method of raising an immune response in a mammal comprising administering to the mammal the immunogenic composition of any of embodiments 31-44.
46. A process for preparing a conjugate of a serogroup X capsular polysaccharide and a carrier molecule, wherein the process is as defined in any of embodiments 2-19.
47. The process of embodiment 46, wherein the conjugate is as defined in any of embodiments 20-30.
48. A pharmaceutical composition comprising (a) a serogroup X capsular polysaccharide and (b) a pharmaceutically acceptable carrier, wherein the composition is in an aqueous formulation.
49. The pharmaceutical composition of embodiment 48, wherein the serogroup X capsular polysaccharide is in the form of a conjugate as defined in any of embodiments 1-30.
50. The pharmaceutical composition of embodiment 48 or embodiment 49, further comprising one or more further antigens as defined in any of embodiments 32-42.
51. A method for assaying a sample suspected to contain serogroup X capsular polysaccharide, comprising the steps of: (i) hydrolysing any serogroup X capsular polysaccharide in the sample, to give a hydrolysate; (ii) subjecting the hydrolysate to liquid chromatography; and (iii) detecting any glucosamine-4-phosphate separated in step (ii).
52. The method of embodiment 51, wherein the sample contains unconjugated serogroup X capsular polysaccharide and/or conjugated serogroup X capsular polysaccharide.
53. The method of embodiment 51 or embodiment 52, wherein conjugated and unconjugated serogroup X capsular polysaccharide in the sample are separated from each other prior to step (i).
54. The method of embodiment 53, wherein the separation uses solid phase extraction.
55. The method of any of embodiments 1-54, wherein step (ii) involves high performance anion exchange chromatography (HPAEC).
56. The method of any of embodiments 1-55, wherein step (iii) involves pulsed amperometric detection (PAD).
57. The method of any of embodiments 1-56, wherein step (i) involves acid hydrolysis.
58. The method of any of embodiments 1-57, wherein step (iii) is quantitative.
59. The method of any preceding embodiment, wherein the sample is prepared by separating conjugated and unconjugated serogroup X capsular polysaccharide in a specimen, and then using the unconjugated material as the sample.
60. A method for analysing a specimen suspected to contain serogroup X capsular polysaccharide, wherein the total serogroup X capsular polysaccharide content is measured by the method of any of embodiments 51-59 except embodiment 53, the unconjugated serogroup X capsular polysaccharide content is measured as described in any one of embodiments 53 to 59, and thus the ratio of unconjugated to total serogroup X capsular polysaccharide can be calculated.

BRIEF DESCRIPTION OF DRAWINGS

FIG. 3 shows a scheme for the conjugation of a serogroup X capsular polysaccharide to CRM197 by TEMPO oxidation followed by reductive amination, and an SDS PAGE analysis of the resultant conjugate.

FIG. 5 shows a scheme for the conjugation of a serogroup X capsular polysaccharide to CRM197 via SIDEA linker, and an SDS PAGE analysis of the resultant conjugate.

FIG. 6 shows a scheme for the conjugation of a serogroup X capsular polysaccharide to CRM197 via SIDEA linker using a different method, and an SDS PAGE analysis of the resultant conjugate.

FIG. 13 shows 2D 1H-31P HMBC NMR spectrum recorded at 400 MHz and 25±0.1° C. on MenA (a) and MenX (b) oligosaccharide generated by acidic hydrolysis. Peaks assignments are labelled.

FIG. 14 shows a) avDP and b) pH as a function of time collected for MenA and MenX capsular polysaccharides and C) O-acetyl status for MenA capsular polysaccharide only at 37° C. and 45° C.

FIG. 15 shows profiles of avDP as a function of time, collected for the stability study at 37° C. and 45° C. for a) MenA and b) MenX capsular polysaccharide at time points (a) 0, (b) 7, (c) 10, (d) 14, (e) 21 days at 45° C. and at (f) 7, (g) 14, (h) 21, (i) 28 days at 37° C. In addition a profile of experimentally degraded MenX capsular polysaccharide, obtained by acidic treatment (sodium acetate pH 4.0, at 80° C. for ~4 hrs), is shown in b) (l).

FIG. 17 shows a scheme for the conjugation of a serogroup X capsular polysaccharide to CRM197 using a further method, and an SDS PAGE analysis of the resultant conjugate.

MODES FOR CARRYING OUT THE INVENTION

Figure 1:
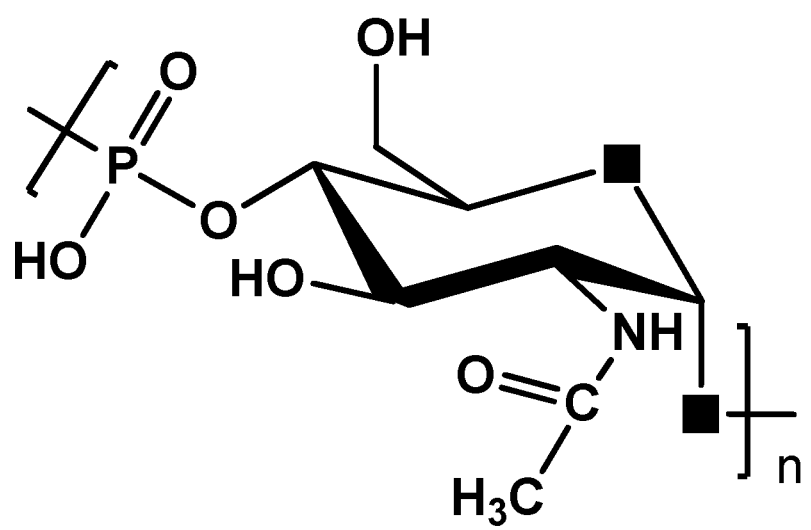
FIG. 1 shows the repeat unit of the serogroup X capsular polysaccharide.

Bacterial Growth for Serogroup X Capsular Polysaccharide Production

In order to identify optimal bacterial growth conditions for production and release of serogroup X capsular polysaccharide in the supernatant, three different media were tested using the MenX 5967 (ST 750) strain. Different growths were performed in flasks and monitored by Proton Nuclear Magnetic Resonance spectroscopy (1H NMR). Culture supernatants were analyzed by NMR sequence with a diffusion filter to cut off signals deriving from lower molecular weight (MW) species and highlight the signals of higher MW serogroup X capsular polysaccharide. Further analysis of the corresponding pellets by 1H High-Resolution Magic Angle Spinning NMR (HR-MAS NMR) in solid state did not show serogroup X capsular polysaccharide signals, indicating that the majority of the polysaccharide was released in the supernatant (considering the limit of detection of this assay, the maximum amount of polysaccharide remaining on the bacteria should be ⅛ of the starting amount). Similar results were obtained with the three media.

In addition to the NMR methodology, a more accurate method for serogroup X capsular polysaccharide quantification in the clarified culture broth was developed (see below) using High-Performance Anion-Exchange Chromatography with Pulsed Amperometric Detection (HPAEC-PAD). As shown in the table below, medium #3 resulted in the highest amount of polysaccharide. It was therefore selected for a higher scale (18 L) fermentation which yielded 356 μg/mL of serogroup X capsular polysaccharide in the supernatant.

| MenX 5967 (ST 750) strain growth in different media and relative polysaccharide production | | | |
| --- | --- | --- | --- |
| Growth medium* | OD(600 nm) | Saccharide (μg/mL) | μg saccharide/OD |
| #1 | 2 | 22.55 | 13.3 |
| #2 | 6 | 42.73 | 7.1 |
| #3 | 2.8 | 62.6 | 22.4 |

*1. modified Catlin v.6: casaminoacids 10 g/L, NaCl 5.8 g/L, glucose 10 g/L, $K_2HPO_4$ 4 g/L, $NH_4Cl$ 1 g/L, $K_2SO_4$ 1 g/L, $MgCl_2 \cdot 6 H_2O$ 0.4 g/L, $CaCl_2 \cdot 2 H_2O$ 0.03 g/L, Fe(III) citrate 0.5 mg/L, pH 7.2;

2. MCDM1: glucose 10 g/L, soy peptone 15 g/L, NaCl 5.80 g/L, $K_2SO_4$ 1 g/L, $K_2HPO_4$ 4 g/L, L-glutamic acid 5 g/L, L-arginine 0.3 g/L, L-serine 0.5 g/L, L-cysteine 0.23 g/L, $MgCl_2$ 0.19 g/L, $CaCl_2$ 0.021 g/L, $FeSO_4$ 0.002 g/L;

3. modified Frantz: L-Glutamic acid 1.6 g/L, $Na_2HPO_4 \cdot 2H_2O$ 15.5 g/L, KCl 0.09 g/L, $NH_4Cl$ 1.25 g/L, pH 7.6, supplemented with: glucose 50 g/L, $MgSO_4 \cdot 7H_2O$ 30 g/L, 25 g/L ultrafiltered yeast extract, L-cysteine 1.5 g/L.

Purification of Serogroup X Capsular Polysaccharide

The process for purifying serogroup X capsular polysaccharide was purified by a method adapted from reference 235.

Conjugate Production and Characterisation

Conjugates were made using polysaccharides of different chain lengths and different conjugation chemistries.

Figure 2:
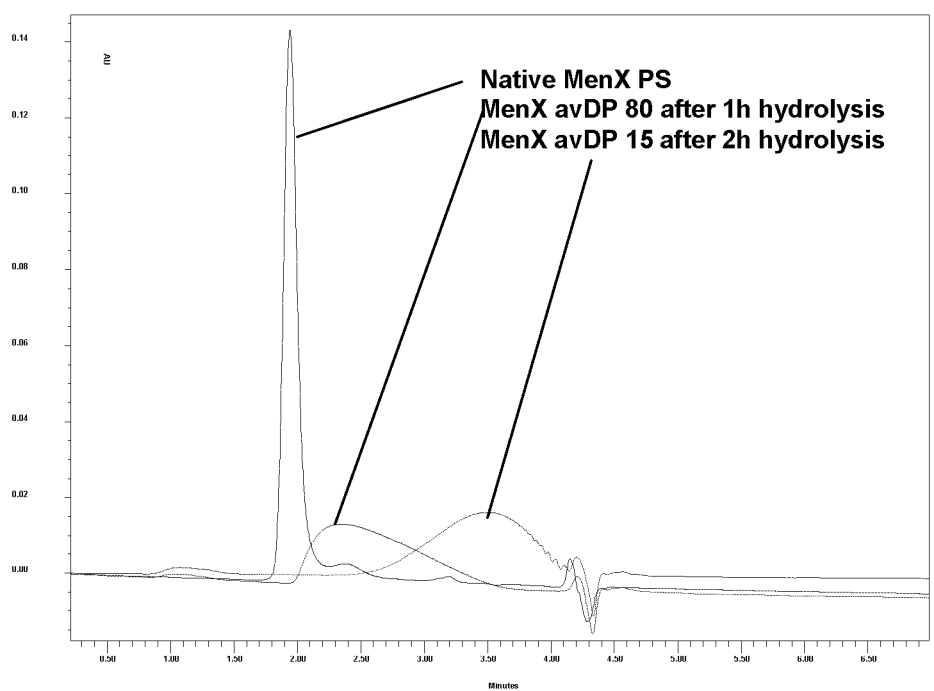
FIG. 2 shows an ultra performance liquid chromatogram for native and hydrolysed serogroup X capsular polysaccharide.

Conjugation by Oxidation and Reductive Amination (Method A):

Purified serogroup X capsular polysaccharide was hydrolysed in 50 mM sodium acetate at pH 4.7, 100° C. for 1 hour (FIG. 2). The average degree of polymerisation of the resulting oligosaccharide was determined to be 80, corresponding to a molecular weight of 25-30 kDa, by NMR. The polysaccharide depolymerization was monitored in process by Ultra Performance Liquid Chromatography-Size Exclusion Chromatography (UPLC-SEC) and phosphorus ($_{31}P$) NMR spectroscopy, and it was quenched by neutralization when the desired avDP was reached. The buffer was exchanged with tetrabutyl ammonium bromide to allow dissolution of the saccharide in dimethylformamide solvent. The saccharide was then oxidized with TEMPO (0.06 eq relative to the MenX repeating subunit), $NaHCO_3$ (9 eq relative to the MenX repeating subunit), TCC (2 eq relative to the MenX repeating subunit) at 0° C. overnight. This oxidation generates an aldehyde group at the C-6 position of individual subunits (FIG. 3). The oxidised saccharide was purified by precipitation with acetone/NaCl and gel filtration using a SEPHADEX G15 column. The saccharide was quantified using HPAEC-PAD and its structural identity confirmed using NMR. There were approximately 4.5 oxidized groups per chain, corresponding to a degree of oxidation of approximately 6% along the circa 80 residue chain. The molecular weight distribution of the oxidized saccharide was measured by UPLC-SEC.

Figure 4:
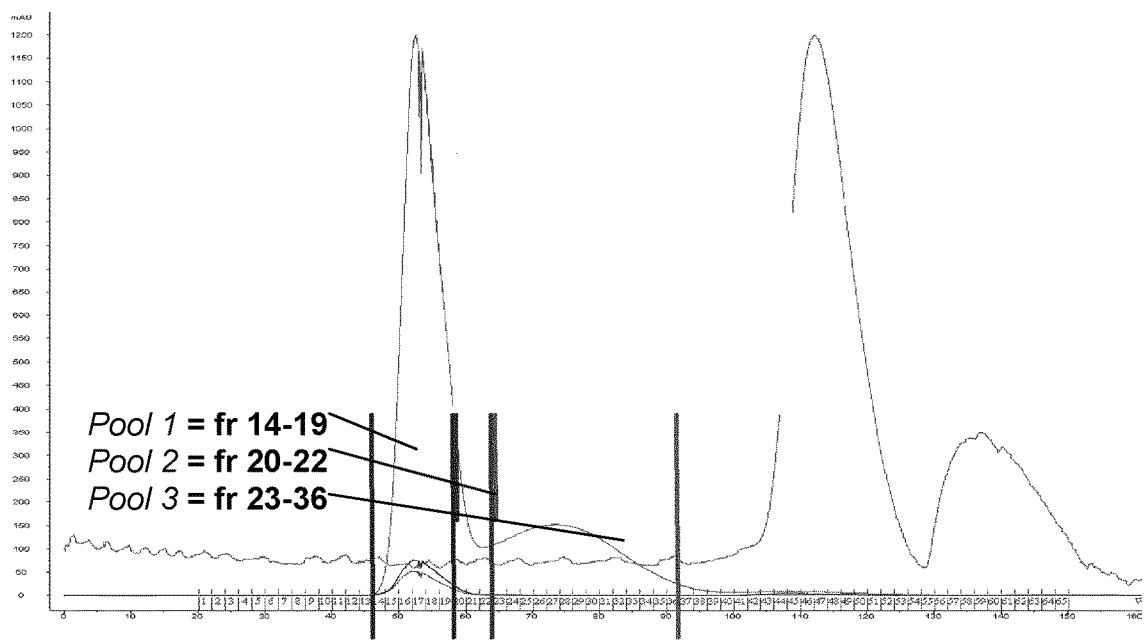
FIG. 4 shows a chromatogram of conjugation mixture run on a SEPHACRYL S300 column with phosphate buffered saline.

The aldehyde group was used for conjugation to carrier protein CRM197 by reductive amination (FIG. 3). Briefly, the saccharide was mixed with 10 mg/ml CRM197 at a 4:1 w/w ratio and $NaBH_3CN$ at a 1:1 w/w ratio in a NaPi 10 mM pH 7.2 buffer. The mixture was left for 72 hours with slow stirring at 37° C. Conjugates were purified on a SEPHACRYL S300 column with phosphate buffered saline and fractions collected into pools (FIG. 4). Conjugation was verified by SDS PAGE (FIG. 3). The properties of the purified conjugates (pool 1) are given below:

| MenX (μg/mL) | CRM197 (μg/mL) | Total mass MenX (mg) | Total mass CRM197 (mg) | MenX/CRM197 (w/w) | MenX yield (%) | CRM197 yield (%) | MenX/CRM197 (mol/mol) | Kd (SEC) | EU/μg (LAL) |
|---|---|---|---|---|---|---|---|---|---|
| 104.8 | 151.3 | 1.26 | 1.82 | 0.69 | 12.6 | 72.6 | 1.7 | 0.7 | 1.6 |

Conjugates were also made by this method in which the polysaccharides were not hydrolysed with sodium acetate and therefore had a native average degree of polymerisation. Further conjugates were made containing polysaccharides with an average degree of polymerisation of 130.

Conjugates were also made by this method in which the carrier protein was tetanus toxoid (TT) or SEQ ID NO: 9(SEQ9). The polysaccharides in these conjugates had an average degree of polymerisation of 130. Other characteristics of these conjugates are given below:

| Carrier | MenX (μg/mL) | Carrier (μg/mL) | MenX/carrier (w/w) | MenX/carrier (mol/mol) | EU/μg (LAL) |
|---|---|---|---|---|---|
| TT | 197.6 | 660.80 | 0.3 | 0.4 | 18.81 |
| SEQ9 | 159.7 | 757.70 | 0.21 | 0.3 | 6.57 |

Conjugation by Reductive Amination Followed by Reaction with SIDEA Linker (Method B):

Purified serogroup X capsular polysaccharide was hydrolysed in 50 mM sodium acetate at pH 4.7, 100° C. for 2 hours (FIG. 2). The average degree of polymerisation of the resulting oligosaccharide was determined to be 15, corresponding to a molecular weight of 5 kDa, by NMR. The saccharide was then solubilised at 5 mg/ml in 5 mM sodium acetate buffer at pH 6.5 with 300 mg/ml $NH_4OAc$ and 49 mg/ml $NaBH_3CN$ for 5 days at 37° C. This step resulted in reductive amination of the terminal aldehyde group to generate a primary amine group (FIG. 5). The reaction mixture was then purified by tangential flow filtration with a 200 cm² HYDROSART (cellulose) 2 kDa-cut off membrane against 1M NaCl and water. The primary amine group was then used for activation with SIDEA and subsequent conjugation to carrier protein CRM197 (FIG. 5). Briefly, the modified saccharide was dissolved in DMSO/water at 9:1 (v/v) with $NEt_3$ (at a molar ratio of $NEt_3$:total $NH_2$ groups of 5:1) at a mol SIDEA:total mol $NH_2$ groups of 12:1 for 3 hours at room temperature. The reaction mixture was then purified by precipitation with 90% dioxane (v/v). The SIDEA-modified saccharide was then reacted with 25 mg/ml CRM197 at a ratio of 13:1 (molar ratio active ester groups: CRM197) in a 25 mM NaPi buffer at pH 7.2. The mixture was left for 5 hours with slow stirring at room temperature. The conjugates were purified by precipitation with $(NH_4)_2SO_4$. Conjugation was verified by SDS PAGE (FIG. 5). The properties of one lot of these conjugates are given below:

Conjugation by Reduction, Oxidation and Reductive Amination Followed by Reaction with SIDEA Linker (Method C):

Purified serogroup X capsular saccharide was reacted at 15 mg/ml in 10 mM NaPi buffer at pH 8 with $NaBH_4$ (12 eq relative to the molecular weight of MenX, solid) for 1.5 hours at room temperature. This step resulted in reduction of the saccharide. The reduced saccharide was then reacted at 6-8 mg/ml in 10 mM NaPi buffer at pH 7.2 with $NaIO_4$ (10 eq relative to the molecular weight of MenX, solid) for 1.5 hours at room temperature. The combined effect of these two steps is the generation of an aldehyde group at the reducing terminus of the saccharide (FIG. 6). The modified saccharide is then subjected to reductive amination to provide a primary amine group that can be used for activation with SIDEA and subsequent conjugation to carrier protein CRM197 (FIG. 6). Briefly, the modified saccharide solubilised at 4-5 mg/ml in 10 mM NaPi buffer at pH 7 with 300 mg/ml $NH_4OAc$ and 49 mg/ml $NaBH_3CN$ for 5 days at 37° C. The modified saccharide was then dissolved in DMSO/water at 9:1 (v/v) with $NEt_3$ (at a molar ratio of $NEt_3$:total $NH_2$ groups of 5:1) at a mol SIDEA:total mol $NH_2$ groups of 12:1 for 3 hours at room temperature. The reaction mixture was then purified by precipitation with 80% acetone (v/v). The resulting SIDEA-modified saccharide was then reacted with 25 mg/ml CRM197 at a ratio of 13:1 (molar ratio active ester groups: CRM197) in a 100 mM NaPi buffer at pH 7.2. The mixture was left overnight with slow stirring at room temperature. The conjugates were purified by precipitation with $(NH_4)_2SO_4$. Conjugation was verified by SDS PAGE (FIG. 6). The properties of one lot of these conjugates are given below:

| MenX (μg/mL) | CRM197 (μg/mL) | MenX/ CRM197 (w/w) | MenX/ CRM197 (mol/mol) | Free saccharide (%) | EU/μg (LAL) |
|---|---|---|---|---|---|
| 129.60 | 628.70 | 0.21 | 2.1 | <6 | 0.01 |

Figure 7:
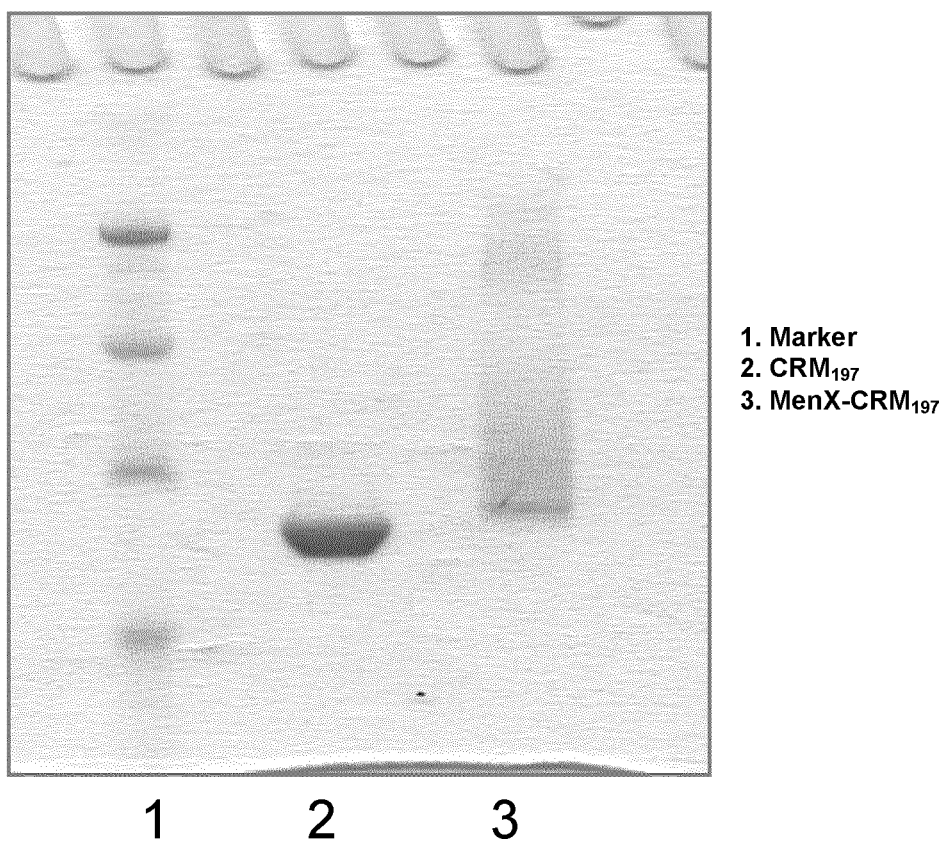
FIG. 7 shows an SDS PAGE analysis of a serogroup X capsular polysaccharide-CRM197 conjugate made using a different linker.

Conjugation Via Alternative Linker (Method D):

The purified serogroup X capsular polysaccharide with an average degree of polymerisation of 15, as described above, was also conjugated to CRM197 using a different linker according to the method of FIG. 7 in U.S. 61/534,751. Conjugation was verified by SDS PAGE (FIG. 7 herein).

Conjugation by Reduction, Oxidation and Reductive Amination with the Carrier (Method E):

Purified serogroup X capsular saccharide was reacted at 15 mg/ml in 10 mM NaPi buffer at pH 8 with $NaBH_4$ (12 eq relative to the molecular weight of MenX, solid) for 2 hours

| MenX (μg/mL) | CRM197 (μg/mL) | Total mass MenX (mg) | Total mass CRM197 (mg) | MenX/CRM197 (w/w) | MenX/CRM197 (mol/mol) | MenX yield (%) | Kd (SEC) | EU/μg (LAL) |
|---|---|---|---|---|---|---|---|---|
| 167.3 | 514.4 | 0.17 | 0.51 | 0.33 | 4.22 | 12.6 | 0.32 | 0.8 | at room temperature. This step resulted in reduction of the saccharide. The reduced saccharide was then reacted at 6-8 mg/ml in 10 mM NaPi buffer at pH 7.2 with NaIO$_4$ (10 eq relative to the molecular weight of MenX, solid) for 1.5 hours at room temperature. The combined effect of these two steps is the generation of an aldehyde group at the reducing terminus of the saccharide (FIG. 17). The modified saccharide is then subjected to reductive amination with carrier protein CRM197. Briefly, the modified saccharide at 2 mg/ml was dissolved in 300 mM NaPi buffer at pH 8 (at a weight ratio of saccharide:CRM197 of 8:1) and NaBH$_3$CN (at a weight ratio of saccharide:NaBH$_3$CN of 4:1) for 4 days at 37° C. Conjugation was verified by SDS PAGE (FIG. 17).

Immunisation Study (1)

General Assay Protocol:

Balb/c mice were immunized by subcutaneous injection according to the schedule described below. The injection volume was 200 μl and the injection contained alum phosphate adjuvant (120 μg per dose). Injections were carried out on days 1, 14 and 28, with bleeds taken at day 0 (for preimmune sera), 28 (post second immunisation sera) and 42 (post third sera).

| Grp | Mice per group | Immunogen | Antigen dose |
|-----|----------------|-----------|--------------|
| 1 | 8 | PBS | — |
| 2 | 16 | MenX-CRM197 (method A) | 1 μg |
| 3 | 16 | MenX-CRM197 (method D) | 1 μg |
| 4 | 16 | MenX-CRM197 (method B) | 1 μg |
| 5 | 16 | MenX-CRM197 (method A) + MenACWY | 1 μg + 2, 1, 1, 1 μg |
| 6 | 16 | MenX-CRM197 (method D) + MenACWY | 1 μg + 2, 1, 1, 1 μg |
| 7 | 16 | MenX-CRM197 (method B) + MenACWY | 1 μg + 2, 1, 1, 1 μg |
| 8 | 16 | MenACWY | 2, 1, 1, 1 μg |
| 9 | 16 | MenX-CRM197 (method D) | 0.1 μg |

MenACWY = mixture of MenA-CRM197, MenC-CRM197, MenW135-CRM197 and MenY-CRM197 prepared according to ref. 10.

Figure 8:
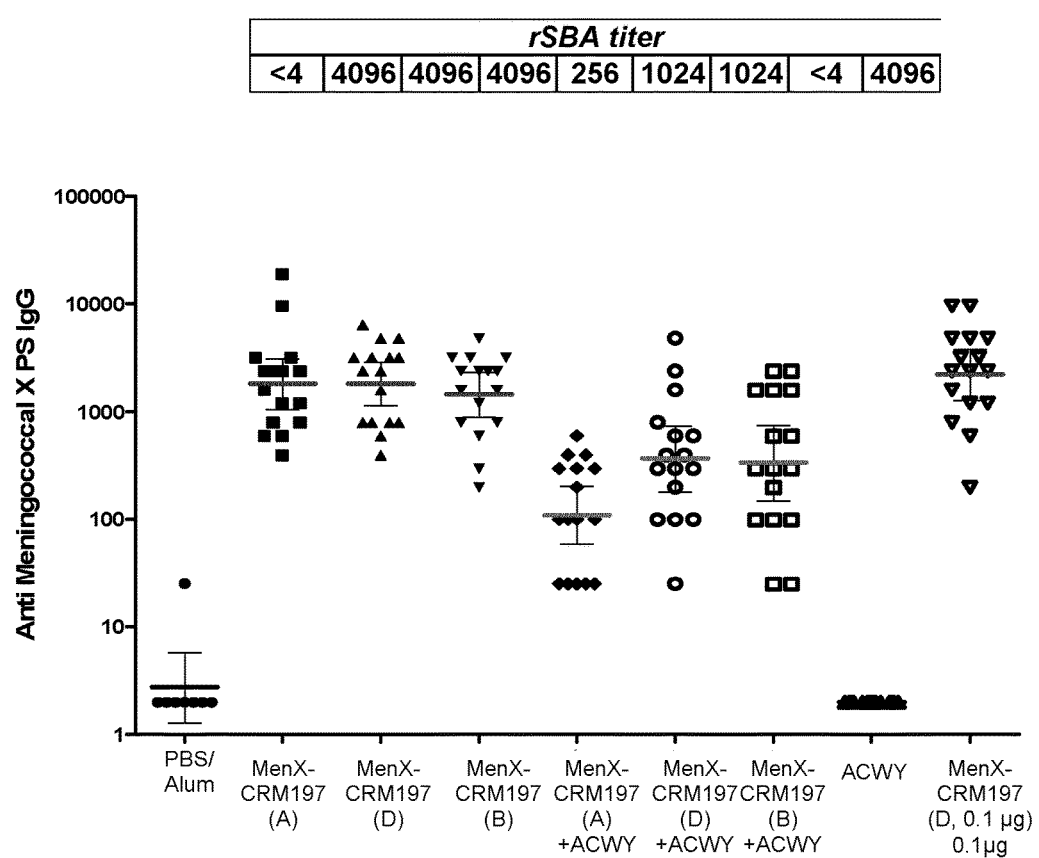
FIG. 8 shows IgG antibody titres against serogroup X capsular polysaccharide and serum bactericidal antibody titres against serogroup X following immunisation with a variety of N. meningitidis conjugates.
Figure 9:
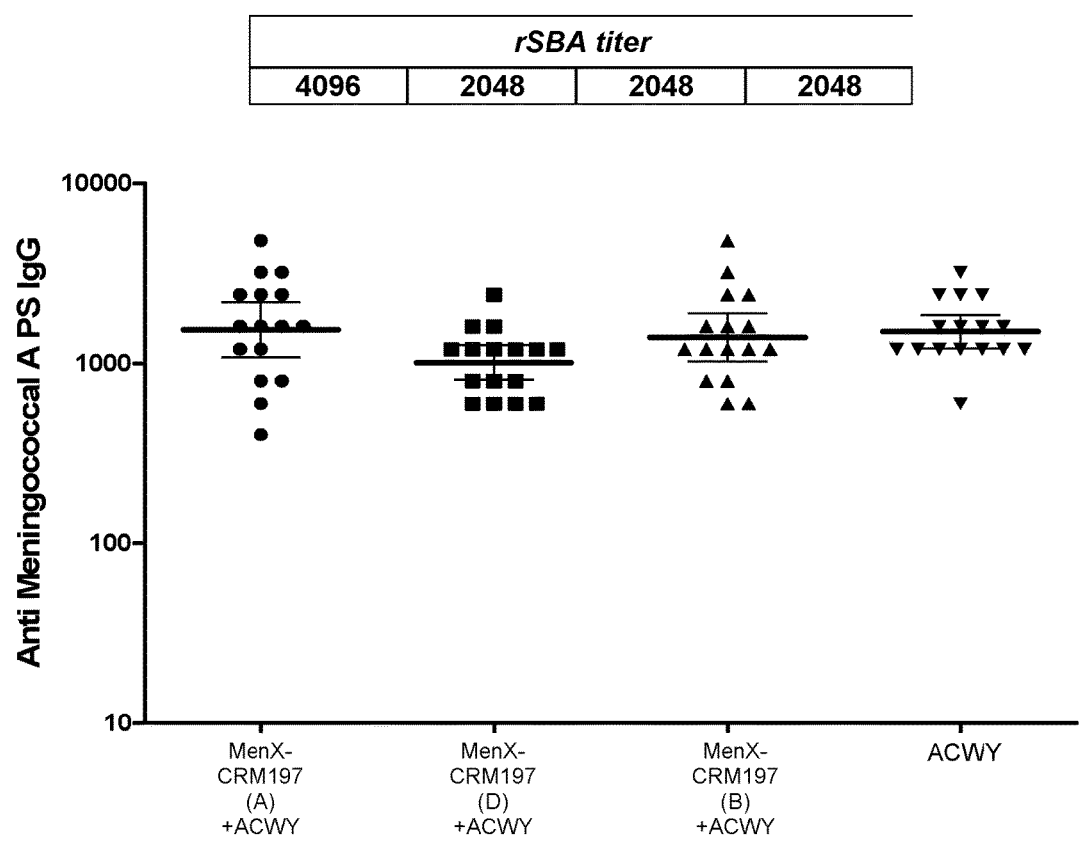
FIG. 9 shows IgG antibody titres against serogroup A capsular polysaccharide and serum bactericidal antibody titres against serogroup A from the same experiment.
Figure 10:
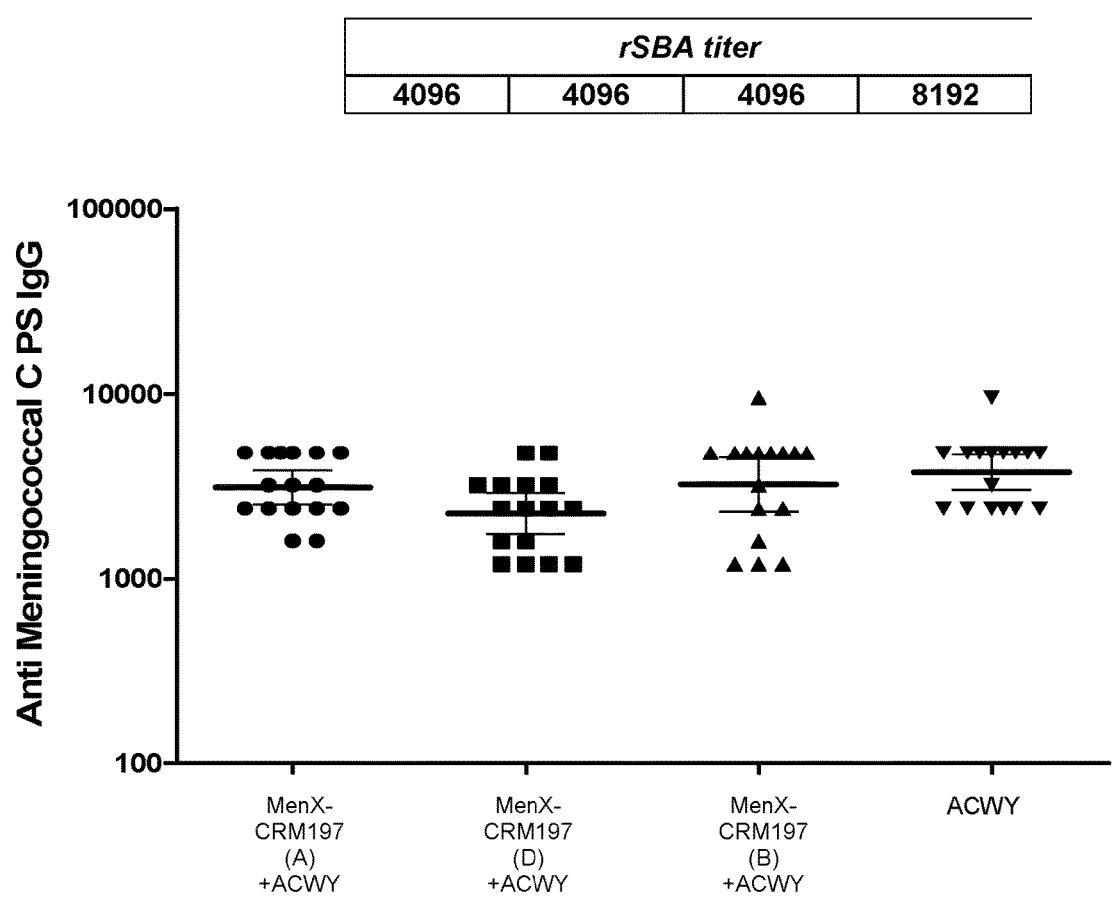
FIG. 10 shows IgG antibody titres against serogroup C capsular polysaccharide and serum bactericidal antibody titres against serogroup C from the same experiment.
Figure 11:
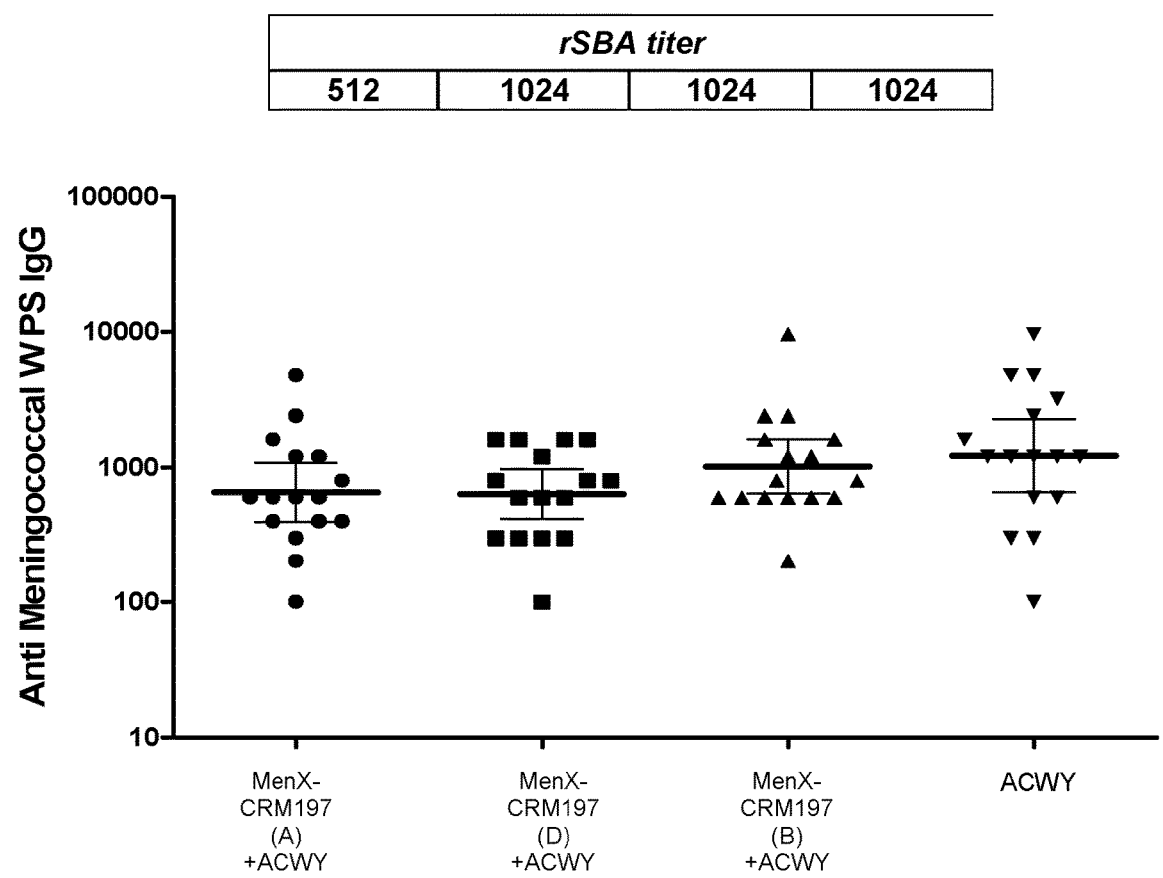
FIG. 11 shows IgG antibody titres against serogroup W135 capsular polysaccharide and serum bactericidal antibody titres against serogroup W135 from the same experiment.
Figure 12:
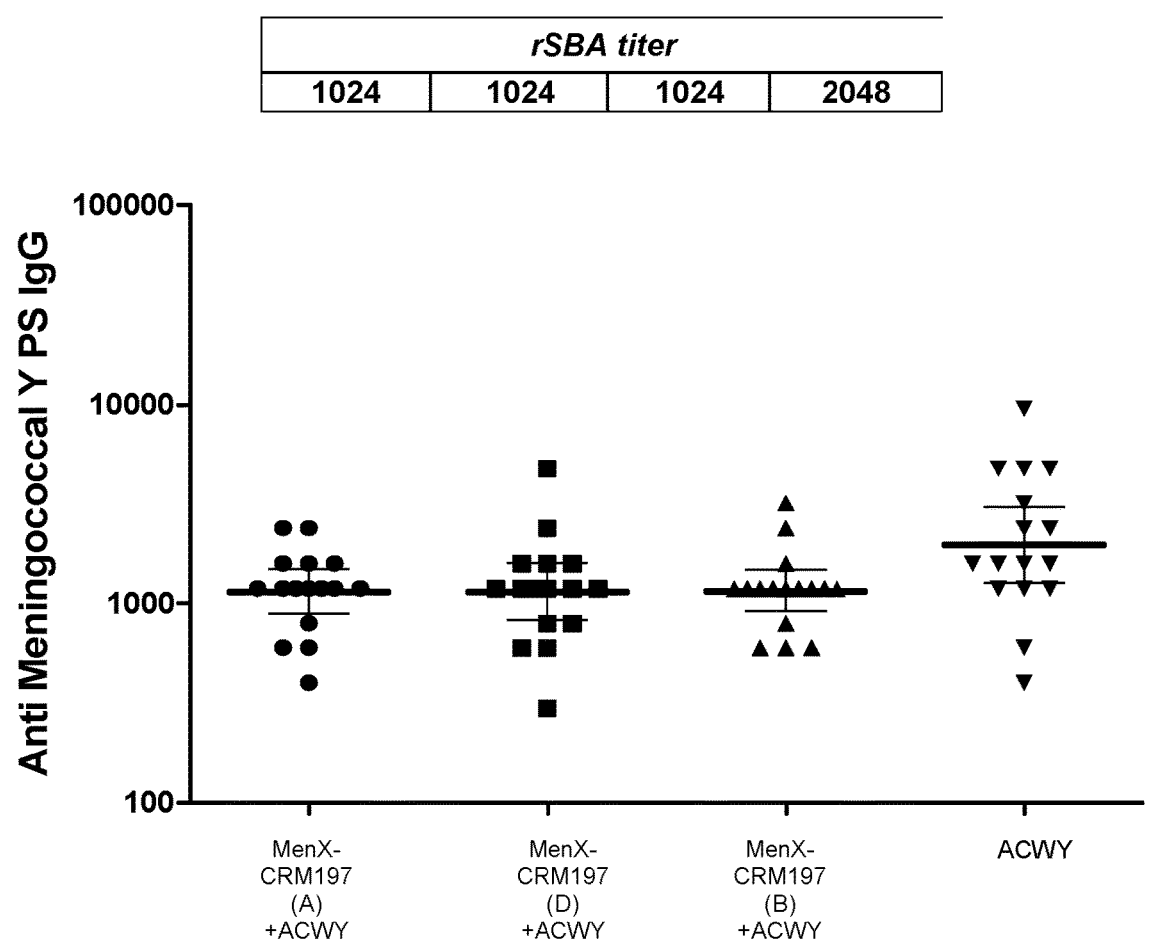
FIG. 12 shows IgG antibody titres against serogroup Y capsular polysaccharide and serum bactericidal antibody titres against serogroup Y from the same experiment.

The post third immunisation IgG antibody titre against serogroup X capsular polysaccharide and serum bactericidal antibody titre against serogroup X strain Z9615 are shown in FIG. 8. The serogroup X conjugates were immunogenic and induced bactericidal antibodies. The response was not diminished when the dose was reduced ten-fold (to 0.1 μg). Responses were slightly reduced when the conjugates were combined with conjugates derived from serogroups A, C, W135 and Y, but still well above controls. Accordingly, immune interference between these conjugates and the serogroup X conjugates appears to be relatively small.

The post third immunisation IgG antibody titres against serogroups A, C, W135 and Y capsular polysaccharides and serum bactericidal antibody titres against these serogroups (using strains F8238, 11, 240070 and 860800 respectively) were also measured for groups 5, 6, 7 and 8. Results are shown in FIGS. 9-12. The responses to the serogroup A, C, W135 and Y conjugates were generally not diminished when combined with the serogroup X conjugates. Once again, these results suggest that there is little immune interference between these conjugates and the serogroup X conjugates.

Anti-serogroup X capsular polysaccharide IgM ELISA units were found to be low for all the conjugates, as expected for conjugate vaccines due to effective isotype switching from IgM to IgG.

Figure 22:
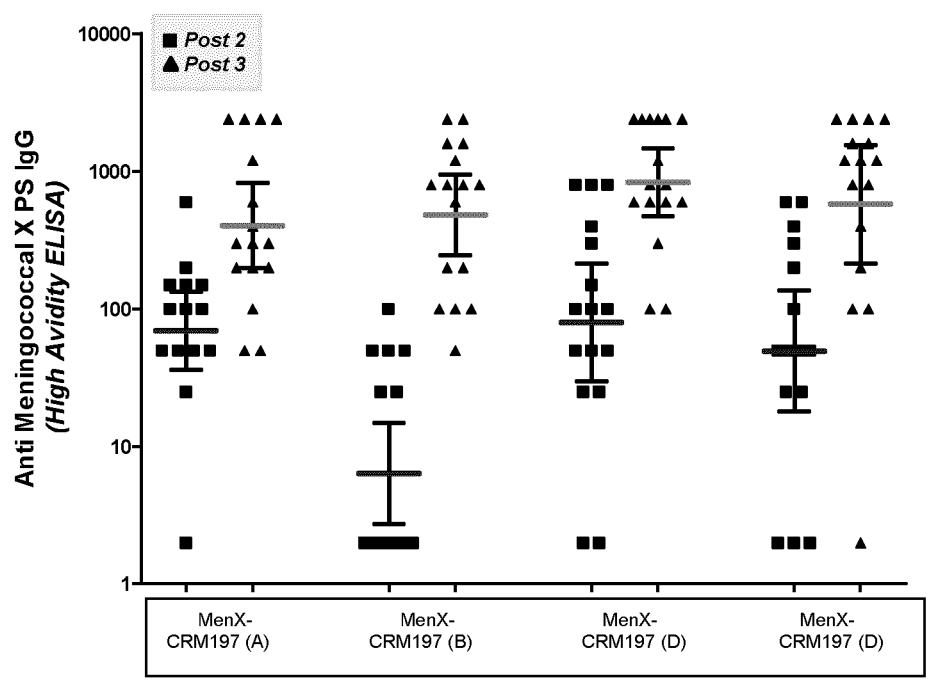
FIG. 22 shows high affinity IgG antibody titres against serogroup X capsular polysaccharide following immunisation with a variety of N. meningitidis conjugates.

A modified ELISA was used to measure higher avidity IgG antibodies only (FIG. 22). The modified ELISA uses a chaotropic salt to select and detect higher avidity IgG antibodies only. Anti-serogroup X capsular polysaccharide IgG ELISA units were low for all the conjugates both after the second and the third dose compared to the units by standard ELISA, but a statistically significant booster effect was observed after the third dose for all the conjugates (P from 0.0006 to <0.0001).

The following table summarises the rabbit complement serum bactericidal antibody titres against the various strains from the pooled post third immunisation sera.

| Antigen Name | Antigen Dose (μg) | MenX Z9615 | MenA F8238 | MenC 11 | MenW 240070 | MenY 860800 |
|---|---|---|---|---|---|---|
| PBS + AlumPhosphate | — | <4 | <16 | <16 | <16 | 32 |
| MenX-CRM197 (A) | 1 | 4096 | <16 | <16 | <16 | 32 |
| MenX-CRM197 (D) | 1 | 4096 | n/a | n/a | n/a | n/a |
| MenX-CRM197 (B) | 1 | 4096 | n/a | n/a | n/a | n/a |
| MenX-CRM197 (A) + MenACWY | 1 + 2, 1, 1, 1 | 256 | 4096 | 4096 | 512 | 1024 |
| MenX-CRM197 (D) + MenACWY | 1 + 2, 1, 1, 1 | 1024 | 2048 | 4096 | 1024 | 1024 |
| MenX-CRM197 (B) + MenACWY | 1 + 2, 1, 1, 1 | 1024 | 2048 | 4096 | 1024 | 1024 |
| MenACWY | 2, 1, 1, 1 | <4 | 2048 | 8192 | 1024 | 2048 |
| MenX-CRM197 (D) | 0.1 | 4096 | n/a | n/a | n/a | n/a |

Immunisation Study (2)

General Assay Protocol:

Balb/c mice were immunized by subcutaneous injection according to the schedule described below. The injection volume was 200 µl and the injection contained alum phosphate adjuvant.

| Group | Mice per group | Immunogen | Antigen dose |
|---|---|---|---|
| 1 | 1-8 | PBS | 1 µg |
| 2 | 9-16 | MenX-CRM197 (method A, native avDP) | 1 µg |
| 3 | 17-24 | MenX-CRM197 (method A, 80 avDP) | 1 µg |
| 4 | 25-32 | MenX-CRM197 (method A, 130 avDP) | 1 µg |
| 5 | 33-40 | MenX-TT (method A, 130 avDP) | 1 µg |
| 6 | 41-48 | MenX-SEQ9 (method A, 130 avDP) | 1 µg |
| 7 | 49-56 | MenX-CRM197 (method A, native avDP) + MenACWY | 1 µg + 2, 1, 1, 1 µg |
| 8 | 57-64 | MenX-CRM197 (method A, 80 avDP) + MenACWY | 1 µg + 2, 1, 1, 1 µg |
| 9 | 65-72 | MenX-CRM197 (method A, 130 avDP) + MenACWY | 1 µg + 2, 1, 1, 1 µg |
| 10 | 73-80 | MenX-TT (method A, 130 avDP) + MenACWY | 1 µg + 2, 1, 1, 1 µg |
| 11 | 81-88 | MenX-SEQ9 (method A, 130 avDP) + MenACWY | 1 µg + 2, 1, 1, 1 µg |

MenACWY = mixture of MenA-CRM197, MenC-CRM197, MenW135-CRM197 and MenY-CRM197 prepared according to ref. 10.

Figure 16:
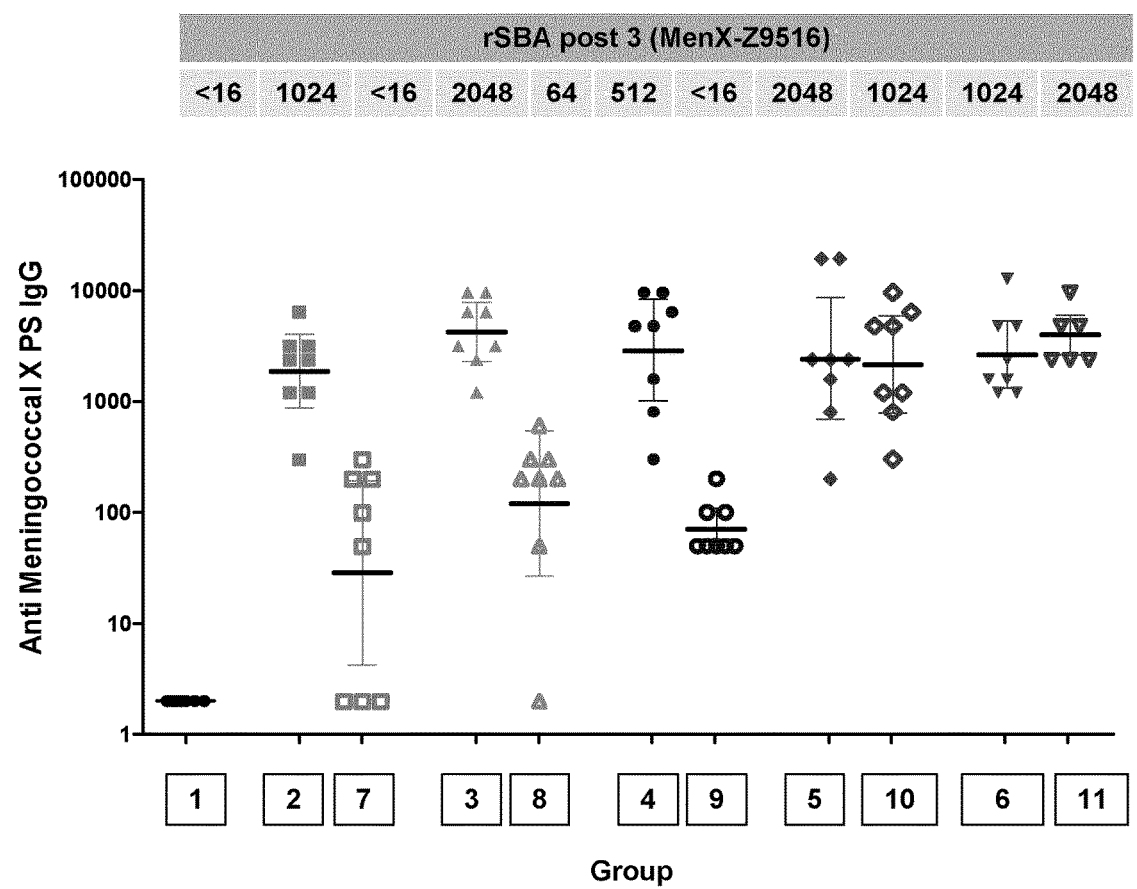
FIG. 16 shows IgG antibody titres against serogroup X capsular polysaccharide and serum bactericidal antibody titres against serogroup X following immunisation with a variety of N. meningitidis conjugates.

The post third immunisation IgG antibody titre against serogroup X capsular polysaccharide and serum bactericidal antibody titre against serogroup X strain Z9615 are shown in FIG. 16. The serogroup X conjugates were immunogenic and induced bactericidal antibodies. Responses were slightly reduced when the MenX-CRM197 conjugates were combined with conjugates derived from serogroups A, C, W135 and Y, but still well above controls. In contrast, little or no reduction was seen when MenX-TT or MenX-SEQ9 conjugates were combined with these conjugates. Accordingly, the use of a different carrier protein for the MenX polysaccharide may help to reduce any immune interference between the serogroup X conjugate and these conjugates.

Figure 18:
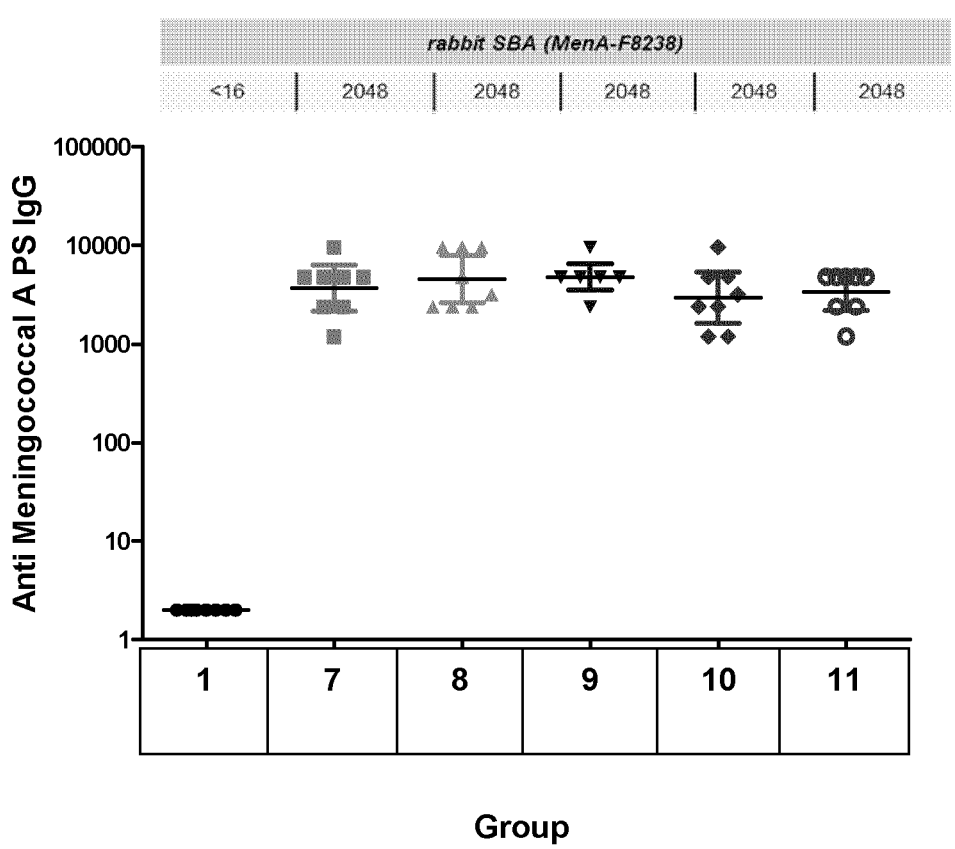
FIG. 18 shows IgG antibody titres against serogroup A capsular polysaccharide and serum bactericidal antibody titres against serogroup A following immunisation with a variety of N. meningitidis conjugates.
Figure 19:
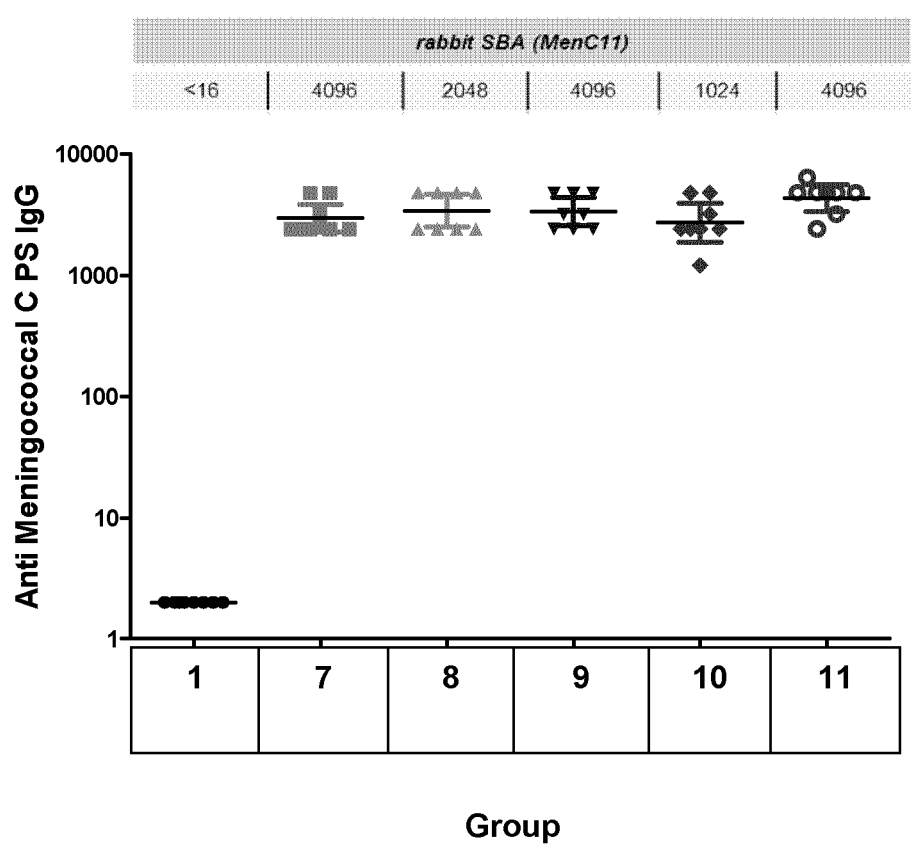
FIG. 19 shows IgG antibody titres against serogroup C capsular polysaccharide and serum bactericidal antibody titres against serogroup C following immunisation with a variety of N. meningitidis conjugates.
Figure 20:
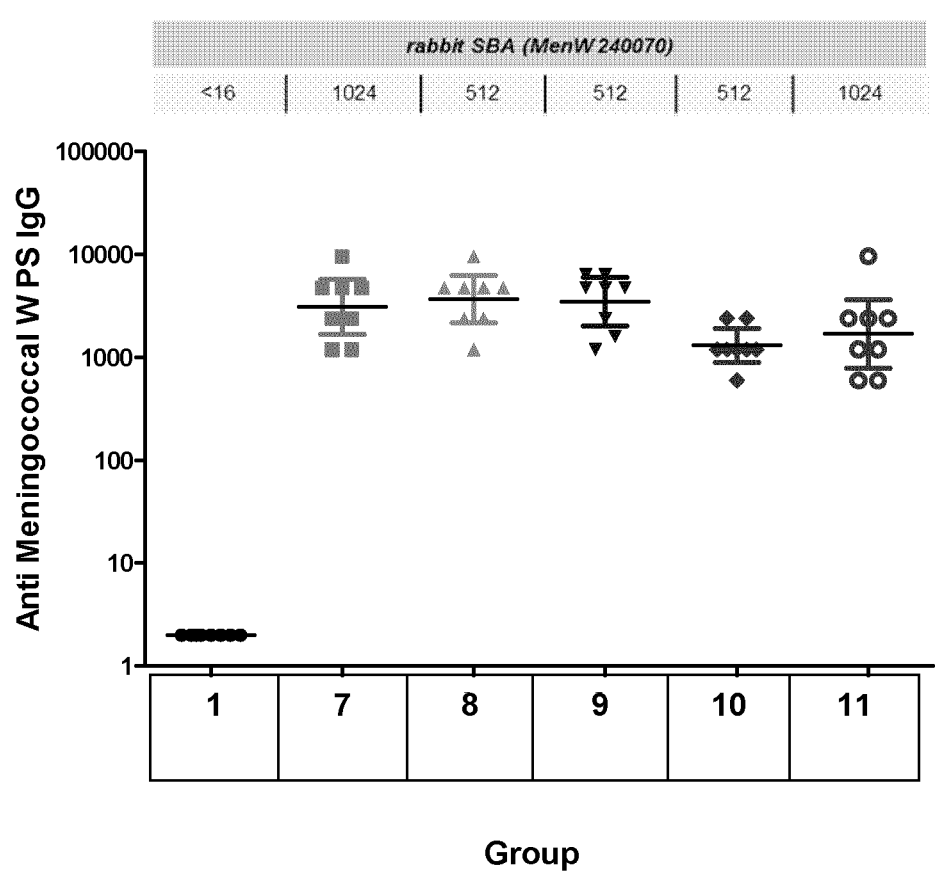
FIG. 20 shows IgG antibody titres against serogroup W135 capsular polysaccharide and serum bactericidal antibody titres against serogroup W135 following immunisation with a variety of N. meningitidis conjugates.
Figure 21:
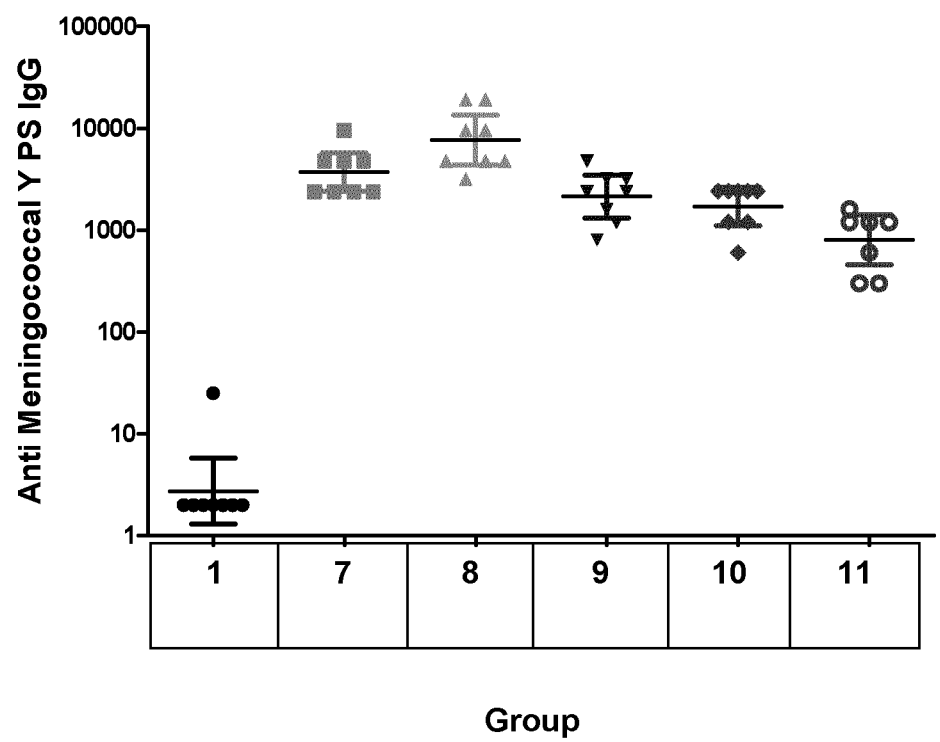
FIG. 21 shows IgG antibody titres against serogroup Y capsular polysaccharide following immunisation with a variety of N. meningitidis conjugates.

The post third immunisation IgG antibody titre against serogroup A capsular polysaccharide and serum bactericidal antibody titre against serogroup A strain F8238 when the MenX conjugates were combined with conjugates derived from serogroups A, C, W135 and Y are shown in FIG. 18. Corresponding data for serogroups C, W135 and Y are shown in FIGS. 19-21.

Stability Study (1)

Materials:

Purified MenA and MenX polysaccharides were obtained according to the method of ref. 10. The purity of the polysaccharide preparation was assessed by estimation of residual protein and nucleic acids contents, which were lower than 1% w/w of saccharide.

NMR Analyses:

1H, 13C and 31P NMR experiments were recorded on Bruker Avance III 400 MHz spectrometer, equipped with a high precision temperature controller, and using 5-mm broadband probe (Bruker). For data acquisition and processing, TOPSPIN version 2.6 software (Bruker) was used. 1H NMR spectra were collected at 25±0.1.degree. C. with 32 k data points over a 10 ppm spectral width, accumulating 128 scans. The spectra were weighted with 0.2 Hz line broadening and Fourier-transformed. The transmitter was set at the water frequency which was used as the reference signal (4.79 ppm). 13C NMR spectra were recorded at 100.6 MHz and 37±0.1° C., with 32 k data points over a 200 ppm spectral width, accumulating 4 k scans. The spectra were weighted with 0.2 Hz line broadening and Fourier-transformed. The transmitter was set at the acetone frequency which was used as the reference signal (30.89 ppm). 31P NMR spectra were recorded at 161.9 MHz at 25±0.1° C., with 32 k data points over a 20 ppm spectral width, accumulating approximately 1 k of scans. The spectra were weighted with 3.0 Hz line broadening and Fourier-transformed. 85% phosphoric acid in deuterium oxide was used as an external standard (0 ppm). All the 1H and 31P NMR spectra were obtained in quantitative manner using a total recycle time to ensure a full recovery of each signal (5.times. Longitudinal Relaxation Time T1). To confirm the degradation mechanism of MenA and MenX capsular polysaccharides and consequently to assign the 31P NMR peaks, bidimensional 1H-31P Heteronuclear Multiple-Bond Correlation (HMBC) experiments were acquired on MenA and MenX oligosaccharide samples, previously generated by acidic hydrolysis in 50 mM sodium acetate pH 4.8 (saccharide concentration of ~10 mg/mL) at 73° C. for ~2.5 hrs and pH 4.0 at 80° C. for ~5.5 hrs (saccharide concentration of ~2.5 mg/mL) respectively. The average degree of polymerization (avDP) of MenA and MenX oligosaccharides was ~12 and ~10 respectively, as estimated by 31P NMR analysis (see paragraph Stability experiments below). These NMR analytical samples were prepared by solubilizing approximately 10 mg of dried saccharide in 0.75 mL of deuterium oxide (99.9% atom D—Aldrich), with a standard pulse-program. 4096 and 512 data points were collected in F2 and F1 dimension respectively. 64 scans were accumulated prior to Fourier transformation to yield a digital resolution of 0.2 Hz and 5.0 Hz per point in F2 and F1 respectively.

HPLC Analyses:

HPLC analyses were conducted using CARBOPAC PA200 column (4 mm.times.250 mm; DIONEX) with guard column (4 mm×50 mm; DIONEX) connected to an ICS 3000 DIONEX system equipped with a Pulsed Amperometric Detector. 100 mM NaOH+10 mM sodium nitrate buffer was used for column equilibration and a three-step gradient with increasing amount of sodium nitrate (100 mM NaOH+ 10 mM, 250 mM, 500 mM sodium nitrate for 80, 15 and 3 min respectively) was used for elution. A flow rate of 0.4 mL/min was used for the entire run of 120 min. 20 .µL samples were injected at a concentration of approximately 1 mg/mL. The effluent was monitored using an electrochemical detector in the pulse amperometric mode with a gold working electrode and an Ag/AgCl reference electrode. A quadruple-potential waveform for carbohydrates was applied. The resulting chromatographic data were processed using Chromeleon software 6.8 (DIONEX).

Stability Experiments:

MenA and MenX polysaccharide solutions at a concentration of approximately 1 mg/mL in 100 mM potassium phosphate buffer pH 7.0 prepared with deuterated water were incubated at 37° C. and 45° C. respectively. At different time points, samples were withdrawn and analysed by NMR and HPLC. pH was also monitored at each time point. The avDP of MenA and MenX was monitored for polysaccharide stability. avDP values were calculated by the integration of 31P NMR spectra and expressed as [(Pde/Pme)+1], where Pde is molar concentration of the phosphodiester in chain groups and Pme the molar concentration of phosphomonoester end groups. The HPLC profiles were also evaluated semi-quantitatively in order to confirm the more accurate stability evaluation collected by 31P NMR assay Degradation Mechanism of MenA and MenX Polysaccharides The NMR $^1$H—$^{31}$P HMBC data on the MenA oligosaccharide, generated by mild acidic hydrolysis, are reported in FIG. 13(a). Due to the presence of O-acetyl groups at $C_3$ and $C_4$ of mannosamine residues, several spin systems were detected and assigned: (i) proton at C1 of 3- or 4-O-acetylated residues $(H_1—P_{de})^{3/4OAc}$; (ii) proton at $C_1$ of de-O-acetylated residues $(H_1—P_{de})^{deOAc}$; (iii) proton at $C_3$ and $C_4$ geminal of O-acetyl groups $(H_3/H_4—P_{de})^{3/4OAc}$; (iv) proton at $C_2$ of 3-O-acetylated residues $(H_2—P_{de})^{3OAc}$; (v) proton at $C_2$ of 4-O-acetylated residues $(H_2—P_{de})^{4OAc}$; (vi) proton at $C_2$ of de-O-acetylated residues $(H_2—P_{de})^{deOAc}$; (vii) protons at $C_5$ and $C_6$ of 3- or 4-O-acetylated residues $(H_{5/6}—P_{de})^{3/4OAc}$; (viii) protons at $C_3$, $C_4$, $C_5$ and $C_6$ of de-O-acetylated residues $(H_{3/4/5/6}—P_{de})^{deOAc}$. The attachment of phosphate at $C_6$, confirmed by the cross peaks of phosphomonoester to proton at $C_6$ of 3- or 4-O-acetylated residues $(H_6—P_{me})^{3/4OAc}$ and to proton at $C_6$ of de-O-acetylated residues $(H_6—P_{me})^{deOAc}$, indicated that during hydrolysis the phosphodiester bond is cleaved leaving a phosphate group attached to the non-reducing terminus, which is consistent with the lower stability of the phosphate-$C_1$ linkage. Because no other $^1$H—$^{31}$P scalar correlation was detected, no phosphate migration involving free hydroxyl groups at C4 or C3 occurred during hydrolysis. $^1$H—$^{31}$P HMBC on the MenX oligosaccharides (FIG. 13(b)) also indicated that the phosphate-$C_1$ linkage is less stable and in this case the non-reducing terminus has a phosphate group attached at $C_4$: the monoester phosphate shows cross-correlation only with proton at $C_4$. Also for MenX, no phosphate migration involving free hydroxyl groups at C3 or C6 occurred during hydrolysis. All the $^{31}$P spin systems were assigned, the phosphodiester and phosphomonoester signals at −1.40 and 4.65 ppm respectively. The proton NMR profile was assigned also by collecting the $^{31}$P-decoupled spectrum which reduces the peaks structure due to this scalar coupling. All the spectra assignments were in agreement with the published results mainly based on $^{13}$C NMR analysis (ref. 30). 13C NMR chemical shifts of MenX capsular polysaccharide were in agreement with published data (ref. 14), as shown in Table 1 below:

TABLE 1

13C NMR chemical shifts of MenX capsular polysaccharide.

| | $C_1$ | $C_2$ | $C_3$ | $C_4$ | $C_5$ | $C_6$ | $CH_3^{NAc}$ | $CO^{NAc}$ |
|---|---|---|---|---|---|---|---|---|
| Chemical shift (ppm) | 95.2 | 54.8 | 71.1 | 75.1 | 73.2 | 61.3 | 23.2 | 175.6 |

Thermal Stability of MenA and MenX Polysaccharides.

Degradation of MenA and MenX capsular polysaccharides, as the consequence of hydrolysis at phosphodiester bonds, results in fragments of lower avDP which expose newly-formed phosphomonoester end groups. In NMR experiments, these phosphomonester groups generate a $^{31}$P resonance signal at higher fields than that originated by the internal phosphodiester groups thus allowing the avDP calculation as described in Stability experiments above. The variation of avDP during storage is an indicator of the polysaccharide stability and so the avDP of samples of MenA and MenX capsular polysaccharides, taken at different time points during exposure at 37° C. and 45° C., was measured by $^{31}$P NMR (Table 2 and FIG. 14(a)):

TABLE 2 avDP estimated by 31P NMR analysis and pH values detected on MenA and MenX samples at different time points and temperatures of 37° C. and 45° C. O-acetylation status of MenA capsular polysaccharide, expressed as mol O-Acetyl groups per mol of repeating unit, is also reported.

| Temperature (° C.) | Time (days) | MenA PS | | | MenX PS | |
|---|---|---|---|---|---|---|
| | | pH | avDP | OAc (mol/mol) | pH | avDP |
| 37 | 0 | 6.97 | >100 | 0.932 | 6.96 | >100 |
| | 7 | 6.91 | 88.1 | 0.916 | 6.91 | >100 |
| | 14 | 6.91 | 68.2 | 0.916 | 6.89 | >100 |
| | 21 | 7.00 | 46.1 | 0.897 | 6.93 | >100 |
| | 28 | 6.96 | 22.9 | 0.883 | 6.91 | >100 |
| 45 | 0 | 6.97 | >100 | 0.932 | 6.96 | >100 |
| | 7 | 6.95 | 22.4 | 0.891 | 6.94 | >100 |
| | 10 | 6.93 | 15.1 | 0.886 | 6.86 | >100 |
| | 14 | 6.91 | 10.5 | 0.851 | 6.85 | >100 |
| | 21 | 6.90 | 5.1 | 0.826 | 6.87 | >100 |

At the sample concentration used, the sensitivity of the technique did not allow measurement of the avDP at time zero for both polysaccharides, when the avDP is higher than 100. For each time point sample the pH was maintained in the range of 7.0±0.1 (FIG. 14(b)).

At 37° C. MenA capsular polysaccharide degraded to an avDP of 22.9 after 28 days of incubation, while at 45° C. degradation was accelerated with an avDP of 5.1 after 21 days. Under the same conditions, MenX capsular polysaccharide did not show degradation (avDP>100 for all time points at both incubation temperatures; based on the assay sensitivity, 100 is the maximum avDP value detectable). HPLC profiles of MenA capsular polysaccharide incubated at 37° C. and 45° C. (FIG. 15) progressively showed increased intensity peaks of shorter oligosaccharides indicating depolymerisation of chains. In comparison, HPLC profiles collected on all MenX samples remain practically unmodified with a broad peak due to long chain polysaccharides at approximately 87 min which additionally demonstrates the higher stability of this carbohydrate. $^1$H NMR analysis confirmed that the incubation of MenA and MenX capsular polysaccharides at 37° C. and 45° C. did not alter the structure of the polysaccharide repeating units. Only a limited decreasing of O-acetylation level (O-acetyl groups are present in MenA capsular polysaccharide only), from 0.932 to 0.883 and 0.826 mol/mol repeating unit at 37° C. and 45° C. was respectively observed (Table 2 and FIG. 14(c)). Taken together, these NMR and HPLC data confirm the higher stability of MenX as compared to MenA capsular polysaccharide in aqueous solution.

Stability Study (2)

Materials:

MenX-CRM197 conjugates were prepared according to methods A, B and C above.

The conjugates prepared according to method A contained polysaccharides with an average degree of polymerisation of 100. Other characteristics of this conjugate lot are given below:

| MenX (µg/mL) | CRM197 (µg/mL) | MenX/CRM197 (w/w) | MenX/CRM197 (mol/mol) | Free saccharide (%) |
|---|---|---|---|---|
| 477.3 | 1378 | 0.35 | 0.7 | <2.3 |

The conjugates prepared according to method B had the following characteristics:

| MenX (µg) | CRM197 (mg) | MenX/CRM197 (w/w) | Free saccharide (%) |
|---|---|---|---|
| 383 | 1.71 | 0.22 | 5.8 |

The conjugates prepared according to method C contained polysaccharides with an average degree of polymerisation of 19. Other characteristics of this conjugate lot are given below:

| MenX (µg/mL) | CRM197 (µg/mL) | MenX/CRM197 (w/w) | MenX/CRM197 (mol/mol) | Free saccharide (%) |
|---|---|---|---|---|
| 129.6 | 628.7 | 0.21 | 2.1 | <6 |

Accelerated stability studies were performed to provide preliminary information on the stability of these conjugates. Stability studies of were performed at 37° C. for 28 days, the time points for measurement were every 7 days (0, 7, 14, 21, 28 days). Samples were monitored by measuring the free saccharide released from the conjugates. The separation of free saccharide was performed by SPE-C4 cartridge using as elution buffer ACN 10-20%+TFA 0.05%. The total and free saccharide was quantified by HPAEC-PAD analysis, allowing a % free saccharide to be calculated. Values for the three lots of conjugate are given below:

| Time (days) | % free saccharide | | |
|---|---|---|---|
| | Method A conjugates | Method B conjugates | Method C conjugates |
| 0 | <2.3 | 5.8 | <2.1 |
| 7 | 4.2 | 29.9 | 24.9 |
| 14 | 6.2 | 51.2 | 31.5 |
| 21 | 8.7 | 48.7 | 34.8 |
| 28 | 10.0 | 56.1 | 42.8 |

The conjugates made using method A were more stable than the conjugates made by methods B and C.

Analytical Study

Materials:

MenX polysaccharide was produced by bacterial growth of the *Neisseria meningitidis* X5967 strain (ST 750) and purified by a method adapted from reference 235. The purity of the polysaccharide preparation was assessed by estimation of residual protein and nucleic acid content using colorimetric assays (both were present at <1% w/w of saccharide), and endotoxin content using the LAL assay (<10 EU/µg of saccharide). Sodium acetate salt (Thermo Scientific Dionex), Sodium hydroxide 50% solution (J.T. Baker), Trifluoroacetic acid (Sigma), Water MilliQ grade (Millipore) were of pro analysis quality.

General Methods:

Total phosphorus content was measured according to the method of reference 24. Reactions were monitored by thin-layer chromatography (TLC) on Silica Gel 60 F254 (Sigma Aldrich); after exam under UV light, compounds were visualized by heating with 10% (v/v) ethanolic $H_2SO_4$. Column chromatography was performed using pre-packed silica cartridges REDISEP (Teledyne-Isco, 0.040-0.063 nm). Unless otherwise specified, a gradient 0→100% of the elution mixture was applied in a COMBIFLASH Rf (Teledyne-Isco) instrument.

$^1H$, $^{13}C$ and $^{31}P$ NMR experiments were recorded on Bruker Avance III 400 MHz spectrometer, equipped with a high precision temperature controller, and using 5-mm broadband probe (Bruker). For data acquisition and processing, TOPSPIN version 2.6 software (Bruker) was used.

$_1H$ NMR spectra were collected at 25±0.1° C. with 32 k data points over a 10 ppm spectral width. The spectra were weighted with 0.2 Hz line broadening and Fourier transformed. Chemical shift values were reported in ppm, relative to internal $Me_4Si$ (0.00 ppm, $CDCl_3$) or the solvent signal (4.79 ppm, D2O). $^{13}C$ NMR spectra were recorded at 100.6 MHz and 37±0.1° C., with 32 k data points over a 200 ppm spectral width. The spectra were weighted with 0.2 Hz line broadening and Fourier-transformed. Chemical shift values were reported in ppm relative to the signal of $CDCl_3$ (77.0 ppm, $CDCl_3$).

$^{31}P$ NMR spectra were recorded at 161.9 MHz at 25±0.1° C., with 32 k data points over a 20 ppm spectral width. The spectra were weighted with 3.0 Hz line broadening and Fourier-transformed. 85% phosphoric acid in deuterium oxide was used as an external standard (0 ppm).

Exact masses were measured by electron spray ionization cut-off spectroscopy, using a Q-Tof micro Macromass (Waters) instrument. Optical rotation was measured with a P-2000 Jasco polarimeter. Benzyl 3,6-di-O-benzyl-2-deoxy-2-phthalimido-β-D-glucopyranoside 3. The starting material 2 (ref. 236) (1.8 g, 3.1 mmol) was dissolved in acetonitrile (200 ml) under nitrogen, and treated with trimethylaminoborane (1.4 g, 18.4 mmol) and $BF_3.Et_2O$ (2.6 ml, 18.4 mmol) at 0° C. After stirring for 1 h at 0° C., the mixture was allowed to reach ambient temperature, at which time the reaction was complete (TLC, 7:3 cyclohexane-EtOAc). MeOH (3 ml) and triethylamine (3 ml) were added, and the mixture was concentrated. The residue was partitioned with aq $NaHCO_3$, and combined organic layers were concentrated and purified on silica gel (cyclohexane-EtOAc) to afford 1.5 g of product 3 (83%). $[\alpha]_D^{24}$=+1.9 (c 0.5, $CHCl_3$). $^1H$ NMR ($CDCl_3$, 400 MHz): δ=7.80-6.95 (m, 19H, Ph), 5.15 (d, 1H, $J_{1,2}$8.0 Hz, H-1), 4.78, 4.47 (2 d, 2H, $^2J$ 12.2 Hz, $CH_2Ph$), 4.72, 4.51 (2 d, 2H, $^2J$ 12.0 Hz, $CH_2Ph$), 4.67, 4.59 (2 d, 2H, $^2J$ 12.0 Hz, $CH_2Ph$), 4.26-4.18 (m, 2H, H-2,3), 3.87-3.88 (m, 3H, H-4,6), 3.66-3.62 (m, 1H, H-5), 2.89 (d, 1H, $J_{2,OH}$ 2.3 Hz, OH-4). $^{13}C$ NMR ($CDCl_3$, 100 MHz): δ=167.81 (CO), 138.15, 137.59, 137.10, 133.67, 131.61, 128.12, 127.91, 127.86, 127.81, 127.58, 127.40 (Ar), 97.35 (C-1), 78.49 (C-3), 74.37, 74.24 ($CH_2Ph$), 73.78 (C-5), 73.45 (C-4), 70.80 ($CH_2Ph$), 70.69 (C-6), 55.37 (C-2). ESI HR-MS ($C_{35}H_{33}NO_7$): m/z=([M+Na]$^+$ found 597.2547; calc 597.2601); ([M+Na]$^-$ found 618.1895; calc 618.1894).

Benzyl 2-acetamido-3,6-di-O-benzyl-2-deoxy-β-D-glucopyranoside 4

A mixture of N-phthalimido compound 3 (1 g, 1.7 mmol) in EtOH (20 ml), containing 1.2 ml of ethylenediamine, was refluxed overnight. After TLC (toluene-EtOAc 4:1) showed the reaction was complete, the mixture was concentrated and re-dissolved in 4:1 EtOH-Ac$_2$O (25 ml). The mixture was stirred for 3 h, then concentrated. Chromatography of the residue (cyclohexane-EtOAc) gave 740 mg of monosaccharide 4, whose NMR data were identical with those recently reported in literature [237].

Benzyl 2-acetamido-3,6-di-O-benzyl-4-(1,5-di-hydro-3-oxo-3λ$^5$-3H-2,4,3-benzodioxaphosphepin-3-yl)-β-D-glucopyranoside 5

N,N-diethyl-1,5-dihydro-3H-2,3,4-benzodioxaphosphepin-3-amine (717 mg, 3 mmol) was added to a solution of the monosaccharide (500 mg, 1 mmol) in CH$_2$Cl$_2$ (9 ml) and 0.45 M 1H-tetrazole in acetonitrile (9 ml) at 0° C. After 10 min the iced bath was removed and stirring was continued. After stirring further 3 h the reaction went to completion (TLC, 1:1 toluene-EtOAc). The mixture was cooled to −20° C. and m-CPBA was added. After 20 min some aq NaHCO$_3$ was added to quench it. The mixture was diluted with CH$_2$Cl$_2$ and extracted in a separatory funnel with aq NaHCO$_3$. Combined organic layers were concentrated and the residue was purified on silica gel (cyclohexane-EtOAc) to furnish 630 mg of product (92%). White crystals from EtOAc, m.p. 159-160° C.=[α]$_D^{24}$=+34.7 (c 0.1, CHCl$_3$). $^1$H NMR (CDCl$_3$, 400 MHz): δ=7.41-7.12 (m, 18H, Ph), 5.90 (d, 1H, J$_{1,2}$7.6 Hz, H-1), 5.17-5.12 (m, 2H, 2 CHPh), 5.00-4.78 (m, 4H, 4 CHPh), 4.65-4.58 (m, 5H, 4 CHPh, H-4), 4.32 (t, 1H, J 9.0 Hz, H-3), 3.89 (d, 1H, J$_{6a,5}$ 9.0 Hz, H-6a), 3.76-3.69 (m, 2H, H-5,6b), 3.46-3.42 (m, 1H, H-2), 1.80 (s, 3H, CH$_3$CO). $^{13}$C NMR (CDCl$_3$, 100 MHz): δ=170.61 (CO), 138.26, 137.36, 134.98, 128.94, 128.35, 127.95, 127.98, 127.80, 127.71, 127.57, 127.50 (Ar), 98.85 (C-1), 78.71 (C-3), 76.72 (C-4), 73.97 (C-5), 73.76, 73.42, 70.09 (CH$_2$Ph), 69.04 (C-6), 68.30, 60.25 (CH$_2$Ph), 56.95 (C-2), 23.40 (CH$_3$CO). $^{31}$P NMR (CDCl$_3$, 162 MHz): δ=0.32. ESI HR-MS (C$_{37}$H$_{40}$NO$_9$P): m/z=([M+H]$^+$ found 674.2476; calc 674.2519).

2-Acetamido-2-deoxy-β-D-glucopyranosyl Phosphate 6

The protected monosaccharide 5 (100 mg, 0.15 mmol) was dissolved in MeOH (10 ml) and hydrogenated over 10% Pd/C (30 mg). The mixture was stirred for 1 d, then it was filtered through a celite pad. The solvent was evaporated and the recovered crude material was purified on a C-18 Isolute SPE cartridge. Fractions containing the sugar were freeze-dried to give 42 mg of foamy product 6 (95%), whose NMR data were in agreement with those reported in literature [238].

High-Performance Anion-Exchange Chromatography with Pulsed Amperometric Detection (HPAEC-PAD) for MenX Quantification:

MenX samples were treated with TFA at a final concentration of 2 M diluted to a total volume of 600 µL in the range 0.5-8 µg/mL. Samples were heated at 100° C. for 2.5 hours in a closed screw-cap test tube, then chilled at 2-8° C. for about 30 minutes, added 700 µL NaOH 2 M and filtered with 0.45 µm ACRODISC (PALL) filters before analysis. A pure preparation of MenX PS or the synthetic monomer 4-GlcNAc-4P, titered through the colorimetric method for total phosphorus content, were used for building the calibration curve, set up with standards in the range of 0.5-8 µg/mL. HPAEC-PAD was performed with a DIONEX ICS3000 equipped with a CarboPac PA1 column (4×250 mm; DIONEX) coupled with PA1 guard column (4×50 mm; DIONEX). Samples were run with a flow rate of 1 mL/min, using a gradient in 10 minutes from 100 mM to 500 mM AcONa in 100 mM NaOH. The effluent was monitored using an electrochemical detector in the pulse amperometric mode with a gold working electrode and an Ag/AgCl reference electrode. A quadruple-potential waveform for carbohydrates was applied. The resulting chromatographic data were processed using CHROMELION software 6.8.

Acid Hydrolysis of MenX Polysaccharide and GlcNAc-4P and NMR Characterization:

A large scale acid hydrolysis was conducted on MenX polysaccharide and on the synthetic monomer (10 mg). Both the samples were dissolved in 2 mL 2 M TFA and hydrolysed at 100° C. for 2.5 hours. The samples were dried and exchanged with D$_2$O for three times before analysis.

Selection of Hydrolysis Conditions:

To identify the optimal conditions for MenX hydrolysis able to completely release the monomer subunits and minimize their degradation, different reaction times for the hydrolysis of MenX polysaccharide (from 1 to 6 hours) performing the hydrolysis in 2 M TFA at 100° C. were explored. A pure preparation of MenX polysaccharide, titered through the colorimetric method for total phosphorus content, was used at two different concentrations (0.5 and 2 µg/mL). One prevalent peak was detected by HPAEC-PAD analysis. The area of the peak increased over time, with a maximum among two and three hours, before decreasing for longer times. Eventually 2.5 hours was selected as optimal time of hydrolysis The linearity of the method was verified in the range 0.5-8 µg/mL (R$^2$=99.807). The method was successfully applied to purification process intermediates, including fermentation broths, and in order to determine the accuracy of the method a recovery study was conducted. Known amounts of polysaccharide were added to standard samples that were subjected to the analysis. The recovery was calculated based on the difference between the total concentration determined for the spiked samples and the concentration found in the un-spiked samples. The mean recovery ranged from 98 to 102%, indicating a high grade of accuracy. Repeatability inter-analysis was performed by analyzing the same sample four times with a CV of 1% and a corresponding average CV of 0.5%.

Synthesis of 4P-GlcNAc:

As shown in Scheme 1, the synthesis of target compound 6 commenced from the regioselective ring opening of protected GlcN 2 (92% yield), which was prepared from galactosamine hydrochloride as described in reference 236. Removal of the N-phthalimido protection by means of ethylenediamine, followed by selective N-acetylation provided known compound 4 in 87% yield [237]. Reaction of 4 with N,N-diethyl-1,5-dihydro-3H-2,3,4-benzodioxaphosphepin-3-amine and 1H-tetrazole and subsequent oxidation with m-chloroperbenzoic acid (m-CPBA) enabled the phosphate group introduction in significantly higher yield than previously reported with other methods [238] and furnished crystalline shelf stable compound 5 (m. p. 159-160° C.). A phosphomonoester peak at 0.32 ppm in the $^{31}$P NMR spectrum, which correlated with the H-4 signal at 4.58 ppm and two couples of CH systems (5.13, 4.98 and 5.14, 4.99 ppm respectively) in the $^1$H—$^{31}$P HMBC NMR spectrum allowed to assess the structure of 5. Finally hydrogenolysis over 10% Pd—C provided the target 4P-GlcNAc 6 in excellent yield (95%) respect to 50% yield attained when unprotected phosphate was present. NMR data of the final product were in good agreement with those reported in literature [239].

Scheme 1.

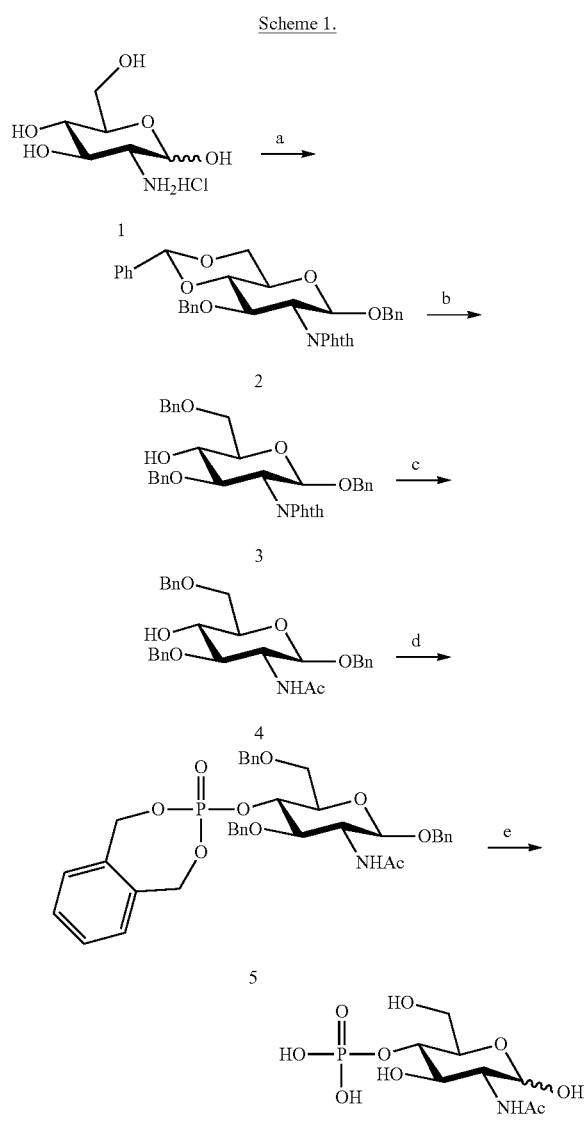

a. Ref. 236; b. trimethylamineborane, BF$_3$·Et$_2$O, CH$_3$CN, 0° C., 83%;
c. H$_2$NCH$_2$CH$_2$NH$_2$, EtOH, reflux; Ac$_2$O, pyridine, 87% (over 2 steps);
d. N,N-diethyl-1,5-dihydro-3H-2,3,4-benzodioxaphosphepin-3-amine,
1H-tetrazole, CH$_2$Cl$_2$; m-CPBA, CH$_2$Cl$_2$, H$_2$O, 92%; e. H$_2$, 10%
Pd—C, 95%.

NMR Characterization of the Products Formed by Acid Hydrolysis of MenX Polysaccharide or 4P-GlcNAc:

MenX polysaccharide and the synthetic monomer 6 were hydrolyzed at larger scale according to the procedure optimized for the HPAEC-PAD analysis in order to confirm the structure of the resulting species by NMR analysis. In both cases 4P-GlcNH was assessed as the prevalent species.

$^1$H NMR spectrum of 4P-GlcNAc 6 showed the α/β anomeric peaks at 5.19 and 4.72 ppm respectively, and the proton signals in the range 4.00-3.69 ppm. H-2α and H-2β were assigned at 3.91 ppm and 3.72 ppm signals by homonuclear COSY NMR correlation. One single peak for phosphate monoester at 0.58 ppm was detected at the $^{31}$P NMR.

After hydrolysis of both the standard 6 and the native MenX PS, $^1$H NMR analysis of the attained 4P-GlcN showed two major anomeric signals corresponding at α/β mixtures in the ratio of 5.5:4.5 and 6.7:3.3 at 5.40 and 4.92 ppm, respectively. Remaining ring proton signals fell between 4.08 and 3.44 ppm, while H-2α (dd, J 3.7 and 10.3 Hz, at 3.91 ppm) and H-2β (dd, J 8.5 and 10.5 Hz, at 3.06 ppm) were shifted up-field due to the loss of the acetyl group. Furthermore, no N-acetyl CH$_3$ signals were detected indicating that hydrolysis resulted in total de-N-acetylation.

Bidimensional $^1$H—$^{31}$P HMBC NMR evidenced two overlapping cross peaks, assigned to the phosphate monoester signals at 0.68 and 0.14 ppm of the $^{31}$P NMR spectrum, correlating with H-4α and H-4β at 3.94 and 3.96 ppm, respectively, in the $^1$H NMR.

Use of 4P-GlcNAc as Standard for MenX Quantification by HPAEC-PAD:

The synthetic monomer 6 was quantified by the colorimetric method for total phosphorus content and then used for building a calibration curve (in the range 0.5-8 μg/mL) in comparison to the native MenX polysaccharide. After subjecting the synthetic monomer and the native polysaccharide to the same hydrolysis conditions optimized for MenX polysaccharide samples, the same peak was detected by HPAEC-PAD and the curves obtained perfectly overlapped. The concentration of unknown samples and intermediates of the polysaccharide purification process was consistent independently from the curve used for the quantification (the difference in saccharide concentration values was <2% for all the tested samples). Mixtures of hydrolyzed MenX polysaccharide and synthetic monomer were also analyzed by HPAEC-PAD on a CARBOPAC PA1 column, eluting with 10 mM sodium hydroxide, to verify the eventual formation of GlcN in the hydrolysis conditions used [26]. Formation of GlcN was less than 5% in moles both for native MenX and synthetic monomer samples.

We also verified the possibility to use the commercially available glucosamine-6-phosphate (6P-GlcN) as standard for the analysis, using the same hydrolysis conditions optimized for MenX. The resulting calibration curve overlapped those obtained with native MenX and its synthetic monomer, but the elution time of the resulting peak detected by HPAEC-PAD was different (8.97 min against 9.88 min for MenX), demonstrating that utilization of 4P-GlcNAc is more straightforward.

This method for MenX polysaccharide quantification is a crucial analytical tool for monitoring the saccharide content of purification process intermediates and a final conjugate vaccine. In addition to allowing the process yield to be calculated, the quantification allows calculation of the saccharide/protein ratio of the conjugate and the % of free saccharide, both of which are important parameters for verifying the quality and consistency of a final vaccine formulation.

The use of a synthetic monomer means that there is no need for the standardization of a batch of polysaccharide for the analysis. The overall method is rapid, permits detection of very low concentrations of sugar (≥0.5 μg/mL of polysaccharide), with minimal sample clean-up and has been verified to work well for the characterization of purification process intermediates, including fermentation broths. The method may be suitable for the quantification of intermediates of conjugation processes and for the characterization of the final vaccine formulations.

It will be understood that the invention has been described by way of example only and modifications may be made whilst remaining within the scope and spirit of the invention.

REFERENCES

[1] Armand et al. (1982) *J. Biol. Stand.* 10:335-339.
[2] Cadoz et al. (1985) *Vaccine* 3:340-342.

[3] *MMWR* (1997) 46(RR-5) 1-10.
[4] Baklaic et al. (1983) *Infect. Immun.* 42:599-604.
[5] Jones (2001) *Curr Opin Investig Drugs* 2:47-49.
[6] Costantino et al. (1992) *Vaccine* 10:691-8.
[7] Lieberman et al. (1996) *JAMA* 275:1499-503.
[8] WO2005/000345.
[9] WO02/058737.
[10] WO03/007985.
[11] Rennels et al. (2002) *Pediatr Infect Dis J* 21:978-979.
[12] WO2004/013400.
[13] Campbell et al. (2002) *J Infect Dis* 186:1848-1851.
[14] Bundle et al. (1974) *J Biol Chem.* 249(15):4797-801.
[15] Delrieu et al. (2011) PLoS One. 6(5):e19513. Epub 2011 May 20.
[16] Chen et al. (2008) Chin Med J (Engl). 121(7):664-6.
[17] Gagneux et al. (2002) Emerg Infect Dis. 8(5):462-6.
[18] WO 2008/102173
[19] Bundle et al. (1974) *J Biol Chem* 249:2275-81.
[20] Tiesjema et al. (1977) *Bull World Health Organ* 55:3578-48.
[21] Teodorović P. *Synthesis of oligosaccharides related to the capsular polysaccharide of Neisseria meningitidis serotype A.* Doctoral Thesis—Stockholm University 2005.
[22] Zon et al. (1982) *Infect Immun* 1982; 37:89-103.
[23] Egan et al. (1982) *J Am Chem Soc* 104:2898-910.
[24] Chen et al. (1956) *Anal. Chem.* 28:1756-1758.
[25] Garrido et al. (2012) *J. Pharm. Biomed. Anal.* 70:295-300.
[26] Xie et al. (2012) *Vaccine* 2012 (30) 5812-5582.
[27] Frash (1990) p. 123-145 of *Advances in Biotechnological Processes* vol. 13 (eds. Mizrahi & Van Wezel)
[28] Inzana (1987) *Infect. Immun.* 55:1573-1579.
[29] WO 2011/023764.
[30] Lemercinier and Jones (1996) *Carbohydrate Res.* 296: 83-96.
[31] Jones and Lemercinier (2002) *J Pharm Biomed Anal.* 30(4):1233-47.
[32] Ravenscroft et al. (1999) *Vaccine* 17:2802-2816.
[33] Costantino et al. (1999) *Vaccine* 17:1251-1263.
[34] Ramsay et al. (2001) *Lancet* 357(9251):195-196.
[35] Lindberg (1999) *Vaccine* 17 Suppl 2:S28-36.
[36] Buttery & Moxon (2000) *J R Coll Physicians Lond* 34:163-168.
[37] Ahmad & Chapnick (1999) *Infect Dis Clin North Am* 13:113-33, vii.
[38] Goldblatt (1998) *J. Med. Microbiol.* 47:563-567.
[39] European patent 0477508.
[40] U.S. Pat. No. 5,306,492.
[41] WO98/42721.
[42] Dick et al. in *Conjugate Vaccines* (eds. Cruse et al.) Karger, Basel, 1989, 10:48-114.
[43] Hermanson *Bioconjugate Techniques*, Academic Press, San Diego (1996) ISBN: 0123423368.
[44] *Research Disclosure,* 453077 (January 2002)
[45] EP-A-0594610.
[46] Ruan et al. (1990) *J Immunol* 145:3379-3384.
[47] WO00/56360.
[48] EP-A-0372501.
[49] EP-A-0378881.
[50] EP-A-0427347.
[51] WO93/17712
[52] WO94/03208.
[53] WO98/58668.
[54] EP-A-0471177.
[55] WO91/01146
[56] Falugi et al. (2001) *Eur J Immunol* 31:3816-3824.
[57] Baraldo et al. (2004) *Infect Immun* 72(8):4884-7.
[58] WO02/091998.
[59] Kuo et al. (1995) *Infect Immun* 63:2706-13.
[60] Michon et al. (1998) *Vaccine.* 16:1732-41.
[61] WO01/72337
[62] WO00/61761.
[63] WO2004/041157.
[64] WO02/34771.
[65] U.S. patent application No. 61/556,456.
[66] International patent application no. PCT/IB2012/056240.
[67] Kato et al. (2003) *Carbohydr. Polym.* 51:69-75.
[68] Angelin et al. (2006) *Eur. J. Org. Chem.,* 4323-4326.
[69] U.S. Pat. No. 4,711,779.
[70] WO00/10599.
[71] U.S. Pat. No. 4,057,685.
[72] WO96/40242.
[73] Lei et al. (2000) *Dev Biol (Basel)* 103:259-264.
[74] WO00/38711; U.S. Pat. No. 6,146,902.
[75] WO99/42130.
[76] WO2004/011027.
[77] Watson (2000) *Pediatr Infect Dis J* 19:331-332.
[78] Rubin (2000) *Pediatr Clin North Am* 47:269-285, v.
[79] Jedrzejas (2001) *Microbiol Mol Biol Rev* 65:187-207.
[80] Bell (2000) *Pediatr Infect Dis J* 19:1187-1188.
[81] Iwarson (1995) *APMIS* 103:321-326.
[82] Gerlich et al. (1990) *Vaccine* 8 Suppl:S63-68 & 79-80.
[83] Hsu et al. (1999) *Clin Liver Dis* 3:901-915.
[84] Gustafsson et al. (1996) *N. Engl. J. Med.* 334:349-355.
[85] Rappuoli et al. (1991) *TIBTECH* 9:232-238.
[86] *Vaccines* (2004) eds. Plotkin & Orenstein. ISBN 0-7216-9688-0.
[87] WO02/02606.
[88] Kalman et al. (1999) *Nature Genetics* 21:385-389.
[89] Read et al. (2000) *Nucleic Acids Res* 28:1397-406.
[90] Shirai et al. (2000) *J Infect. Dis.* 181(Suppl 3):S524-S527.
[91] WO99/27105.
[92] WO00/27994.
[93] WO00/37494.
[94] WO99/28475.
[95] Ross et al. (2001) *Vaccine* 19:4135-4142.
[96] Sutter et al. (2000) *Pediatr Clin North Am* 47:287-308.
[97] Zimmerman & Spann (1999) *Am Fam Physician* 59:113-118, 125-126.
[98] Dreesen (1997) *Vaccine* 15 Suppl:S2-6.
[99] *MMWR Morb Mortal Wkly Rep* 1998 Jan. 16; 47(1):12, 19.
[100] McMichael (2000) *Vaccine* 19 Suppl 1:S101-107.
[101] WO02/34771.
[102] Dale (1999) *Infect Dis Clin North Am* 13:227-43, viii.
[103] Ferretti et al. (2001) *PNAS USA* 98: 4658-4663.
[104] WO03/093306.
[105] WO02004/018646.
[106] WO2004/041157.
[107] Ichiman and Yoshida (1981) *J. Appl. Bacteriol.* 51:229.
[108] U.S. Pat. No. 4,197,290
[109] Ichiman et al. (1991) *J. Appl. Bacteriol.* 71:176.
[110] Robinson & Torres (1997) *Seminars in Immunology* 9:271-283.
[111] Donnelly et al. (1997) *Annu Rev Immunol* 15:617-648.
[112] Scott-Taylor & Dalgleish (2000) *Expert Opin Investig Drugs* 9:471-480.
[113] Apostolopoulos & Plebanski (2000) *Curr Opin Mol Ther* 2:441-447.
[114] Ilan (1999) *Curr Opin Mol Ther* 1:116-120.

[115] Dubensky et al. (2000) *Mol Med* 6:723-732.
[116] Robinson & Pertmer (2000) *Adv Virus Res* 55:1-74.
[117] Donnelly et al. (2000) *Am J Respir Crit Care Med* 162(4 Pt 2):S190-193.
[118] Davis (1999) *Mt. Sinai J. Med.* 66:84-90.
[119] Paoletti et al. (2001) *Vaccine* 19:2118-2126.
[120] WO00/56365.
[121] Gennaro (2000) *Remington: The Science and Practice of Pharmacy.* 20th edition, ISBN: 0683306472.
[122] WO03/009869.
[123] Almeida & Alpar (1996) *J. Drug Targeting* 3:455-467.
[124] Agarwal & Mishra (1999) *Indian J Exp Biol* 37:6-16.
[125] WO00/53221.
[126] Jakobsen et al. (2002) *Infect Immun* 70:1443-1452.
[127] Bergquist et al. (1998) *APMIS* 106:800-806.
[128] Baudner et al. (2002) *Infect Immun* 70:4785-4790.
[129] Ugozzoli et al. (2002) *J Infect Dis* 186:1358-1361.
[130] *Vaccine Design* . . . (1995) eds. Powell & Newman. ISBN: 030644867X. Plenum.
[131] WO00/23105.
[132] WO90/14837.
[133] Podda (2001) *Vaccine* 19:2673-80.
[134] Frey et al. (2003) *Vaccine* 21:4234-7.
[135] U.S. Pat. No. 6,299,884.
[136] U.S. Pat. No. 6,451,325.
[137] U.S. Pat. No. 5,057,540.
[138] WO96/33739.
[139] EP-A-0109942.
[140] WO96/11711.
[141] WO00/07621.
[142] Barr et al. (1998) *Advanced Drug Delivery Reviews* 32:247-271.
[143] Sjolanderet et al. (1998) *Advanced Drug Delivery Reviews* 32:321-338.
[144] Niikura et al. (2002) *Virology* 293:273-280.
[145] Lenz et al. (2001) *J Immunol* 166:5346-5355.
[146] Pinto et al. (2003) *J Infect Dis* 188:327-338.
[147] Gerber et al. (2001) *Virol* 75:4752-4760.
[148] WO03/024480
[149] WO03/024481
[150] Gluck et al. (2002) *Vaccine* 20:B10-B16.
[151] EP-A-0689454.
[152] Johnson et al. (1999) *Bioorg Med Chem Lett* 9:2273-2278.
[153] Evans et al. (2003) *Expert Rev Vaccines* 2:219-229.
[154] Meraldi et al. (2003) *Vaccine* 21:2485-2491.
[155] Pajak et al. (2003) *Vaccine* 21:836-842.
[156] Kandimalla et al. (2003) *Nucleic Acids Research* 31:2393-2400.
[157] WO02/26757.
[158] WO99/62923.
[159] Krieg (2003) *Nature Medicine* 9:831-835.
[160] McCluskie et al. (2002) *FEMS Immunology and Medical Microbiology* 32:179-185.
[161] WO98/40100.
[162] U.S. Pat. No. 6,207,646.
[163] U.S. Pat. No. 6,239,116.
[164] U.S. Pat. No. 6,429,199.
[165] Kandimalla et al. (2003) *Biochemical Society Transactions* 31 (part 3):654-658.
[166] Blackwell et al. (2003) *J Immunol* 170:4061-4068.
[167] Krieg (2002) *Trends Immunol* 23:64-65.
[168] WO01/95935.
[169] Kandimalla et al. (2003) *BBRC* 306:948-953.
[170] Bhagat et al. (2003) *BBRC* 300:853-861.
[171] WO03/035836.
[172] WO95/17211.
[173] WO98/42375.
[174] Beignon et al. (2002) *Infect Immun* 70:3012-3019.
[175] Pizza et al. (2001) *Vaccine* 19:2534-2541.
[176] Pizza et al. (2000) *Int J Med Microbiol* 290:455-461.
[177] Scharton-Kersten et al. (2000) *Infect Immun* 68:5306-5313.
[178] Ryan et al. (1999) *Infect Immun* 67:6270-6280.
[179] Partidos et al. (1999) *Immunol Lett* 67:209-216.
[180] Peppoloni et al. (2003) *Expert Rev Vaccines* 2:285-293.
[181] Pine et al. (2002) *J Control Release* 85:263-270.
[182] Domenighini et al. (1995) *Mol Microbiol* 15:1165-1167.
[183] WO99/40936.
[184] WO99/44636.
[185] Singh et al] (2001) *J Cont Release* 70:267-276.
[186] WO99/27960.
[187] U.S. Pat. No. 6,090,406
[188] U.S. Pat. No. 5,916,588
[189] EP-A-0626169.
[190] WO99/52549.
[191] WO01/21207.
[192] WO01/21152.
[193] Andrianov et al. (1998) *Biomaterials* 19:109-115.
[194] Payne et al. (1998) *Adv Drug Delivery Review* 31:185-196.
[195] Stanley (2002) *Clin Exp Dermatol* 27:571-577.
[196] Jones (2003) *Curr Opin Investig Drugs* 4:214-218.
[197] WO04/60308
[198] WO04/64759.
[199] WO99/11241.
[200] WO94/00153.
[201] WO98/57659.
[202] European patent applications 0835318, 0735898 and 0761231.
[203] Hoskins et al. (2001) J. Bacteriol. 183:5709-5717.
[204] Falugi et al. (2001) *Eur J Immunol.* 31(12):3816-24.
[205] Geysen et al. (1984) *PNAS USA* 81:3998-4002.
[206] Carter (1994) *Methods Mol Biol* 36:207-23.
[207] Jameson, B A et al. 1988, *CABIOS* 4(1):181-186.
[208] Raddrizzani & Hammer (2000) *Brief Bioinform* 1(2):179-89.
[209] De Lalla et al. (1999) *J. Immunol.* 163:1725-29.
[210] Brusic et al. (1998) *Bioinformatics* 14(2):121-30
[211] Meister et al. (1995) *Vaccine* 13(6):581-91.
[212] Roberts et al. (1996) *AIDS Res Hum Retroviruses* 12(7):593-610.
[213] Maksyutov & Zagrebelnaya (1993) *Comput Appl Biosci* 9(3):291-7.
[214] Feller & de la Cruz (1991) *Nature* 349(6311):720-1.
[215] Hopp (1993) *Peptide Research* 6:183-190.
[216] Welling et al. (1985) *FEBS Lett.* 188:215-218.
[217] Davenport et al. (1995) *Immunogenetics* 42:392-297.
[218] WO2004/092209.
[219] WO2008/061953.
[220] WO2005/090985
[221] Hardy et al. (1988) *Anal Biochem* 170:54-62.
[222] Wang et al. (1990) *Anal Biochem* 190:182-187.
[223] WO2005/114171.
[224] T. W. Greene and P. G. M. Wuts in "Protective groups in organic chemistry" John Wiley and Sons, 4th Edition, 2006.
[225] Gennaro (2000) *Remington: The Science and Practice of Pharmacy.* 20th edition, ISBN: 0683306472.
[226] *Methods In Enzymology* (S. Colowick and N. Kaplan, eds., Academic Press, Inc.)

[227] *Handbook of Experimental Immunology*, Vols. I-IV (D. M. Weir and C. C. Blackwell, eds, 1986, Blackwell Scientific Publications)
[228] Sambrook et al. (2001) *Molecular Cloning: A Laboratory Manual,* 3rd edition (Cold Spring Harbor Laboratory Press).
[229] *Handbook of Surface and Colloidal Chemistry* (Birdi, K. S. ed., CRC Press, 1997)
[230] Ausubel et al. (eds) (2002) *Short protocols in molecular biology,* 5th edition (Current Protocols).
[231] *Molecular Biology Techniques: An Intensive Laboratory Course,* (Ream et al., eds., 1998, Academic Press)
[232] *PCR (Introduction to Biotechniques Series)*, 2nd ed. (Newton & Graham eds., 1997, Springer Verlag)
[233] *Current Protocols in Molecular Biology* (F. M. Ausubel et al., eds., 1987) Supplement 30
[234] Smith & Waterman (1981) *Adv. Appl. Math.* 2: 482-489.
[235] Micoli et al. (2012) Vaccine 30: 853-861.
[236] Debenham et al. (1997) *J. Org. Chem.* 62:4591-4600.
[237] Bera et al. (2011) *J. Org. Chem.* 76:3181-3193.
[238] Bundle et al. (1974) *Can. J. Biochem.* 52(9):723-725.
[239] Berti et al. (2012) Vaccine 30: 6409-6415.

The invention claimed is:

1. A composition comprising a conjugate of a *Neisseria meningitidis* serogroup X capsular polysaccharide and a carrier protein, wherein conjugation of the capsular polysaccharide to the carrier protein is direct, wherein the carrier protein is conjugated to oxidized primary hydroxyl group of 1-10% of the residues in the capsular polysaccharide, and wherein the conjugate comprises less than 50% free saccharide released from the conjugate after 28 days at 37° C.

2. The composition of claim 1, wherein the conjugation is with a primary amine group on the carrier protein.

3. The composition of claim 1, wherein a hydroxyl group in the polysaccharide is covalently linked to an amino group in the carrier protein.

4. The composition of claim 1, wherein the carrier protein is a diphtheria toxoid, tetanus toxoid, CRM197 or *Haemophilus influenzae* protein D.

5. The composition of claim 1, further comprising one or more additional antigens.

6. The composition of claim 1, further comprising a *Neisseria meningitidis* serogroup A capsular polysaccharide.

7. The composition of claim 1, wherein the composition is in an aqueous formulation.

8. A vaccine comprising the composition of claim 1, wherein the conjugate is purified.

9. A method of raising an immune response to a *Neisseria meningitidis* serogroup X capsular polysaccharide in a mammal comprising administering to the mammal an immunologically effective amount of the composition of claim 1.

10. A pharmaceutical composition comprising (a) the composition of claim 1 and (b) a pharmaceutically acceptable carrier, wherein the composition is in an aqueous formulation.

11. The pharmaceutical composition of claim 10, further comprising one or more additional antigens.

* * * * *

SEQUENCE LISTING

```
<160> NUMBER OF SEQ ID NOS: 10

<210> SEQ ID NO 1
<211> LENGTH: 167
<212> TYPE: PRT
<213> ORGANISM: Streptococcus pneumoniae

<400> SEQUENCE: 1

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
                20                  25                  30

Ser Thr Tyr Thr Val Lys Glu Gly Asp Thr Leu Ser Glu Ile Ala Glu
            35                  40                  45

Thr His Asn Thr Thr Val Glu Lys Leu Ala Glu Asn Asn His Ile Asp
        50                  55                  60

Asn Ile His Leu Ile Tyr Val Asp Gln Glu Leu Val Ile Asp Gly Pro
65                  70                  75                  80

Val Ala Pro Val Ala Thr Pro Ala Pro Ala Thr Tyr Ala Ala Pro Ala
                85                  90                  95

Ala Gln Asp Glu Thr Val Ser Ala Pro Val Ala Glu Thr Pro Val Val
                100                 105                 110

Ser Glu Thr Val Val Ser Thr Val Ser Gly Ser Glu Ala Glu Ala Lys
            115                 120                 125

Glu Trp Ile Ala Gln Lys Glu Ser Gly Gly Ser Tyr Thr Ala Thr Asn
        130                 135                 140

Gly Arg Tyr Ile Gly Arg Tyr Gly Ser Trp Thr Ala Ala Lys Asn Phe
145                 150                 155                 160

Trp Leu Asn Asn Gly Trp Tyr
                165

<210> SEQ ID NO 2
<211> LENGTH: 195
<212> TYPE: PRT
<213> ORGANISM: Streptococcus pneumoniae

<400> SEQUENCE: 2

Met Lys Ser Ile Thr Lys Lys Ile Lys Ala Thr Leu Ala Gly Val Ala
1               5                   10                  15

Ala Leu Phe Ala Val Phe Ala Pro Ser Phe Val Ser Ala Gln Glu Ser
                20                  25                  30

Ser Thr Tyr Thr Val Lys Glu Gly Asp Thr Leu Ser Glu Ile Ala Glu
            35                  40                  45

Thr His Asn Thr Thr Val Glu Lys Leu Ala Glu Asn Asn His Ile Asp
        50                  55                  60
```

```
Asn Ile His Leu Ile Tyr Val Asp Gln Glu Leu Val Ile Asp Gly Pro
 65                  70                  75                  80

Val Ala Pro Val Ala Thr Pro Ala Pro Ala Tyr Ala Ala Pro Ala
                 85                  90                  95

Ala Gln Asp Glu Thr Val Ser Ala Pro Val Ala Glu Thr Pro Val Val
            100                 105                 110

Ser Glu Thr Val Val Ser Thr Val Ser Gly Ser Glu Ala Glu Ala Lys
            115                 120                 125

Glu Trp Ile Ala Gln Lys Glu Ser Gly Gly Ser Tyr Thr Ala Thr Asn
        130                 135                 140

Gly Arg Tyr Ile Gly Arg Tyr Gln Leu Thr Asp Ser Tyr Leu Asn Gly
145                 150                 155                 160

Asp Tyr Ser Ala Glu Asn Gln Glu Arg Val Ala Asp Ala Tyr Val Ala
                165                 170                 175

Gly Arg Tyr Gly Ser Trp Thr Ala Ala Lys Asn Phe Trp Leu Asn Asn
            180                 185                 190

Gly Trp Tyr
        195

<210> SEQ ID NO 3
<211> LENGTH: 392
<212> TYPE: PRT
<213> ORGANISM: Streptococcus pneumoniae

<400> SEQUENCE: 3

Met Lys Lys Lys Ile Leu Ala Ser Leu Leu Ser Thr Val Met Val
  1               5                  10                  15

Ser Gln Val Ala Val Leu Thr Thr Ala His Ala Glu Thr Thr Asp Asp
                 20                  25                  30

Lys Ile Ala Ala Gln Asp Asn Lys Ile Ser Asn Leu Thr Ala Gln Gln
             35                  40                  45

Gln Glu Ala Gln Lys Gln Val Asp Gln Ile Gln Glu Gln Val Ser Ala
         50                  55                  60

Ile Gln Ala Glu Gln Ser Asn Leu Gln Ala Glu Asn Asp Arg Leu Gln
 65                  70                  75                  80

Ala Glu Ser Lys Lys Leu Glu Gly Glu Ile Thr Glu Leu Ser Lys Asn
                 85                  90                  95

Ile Val Ser Arg Asn Gln Ser Leu Glu Lys Gln Ala Arg Ser Ala Gln
            100                 105                 110

Thr Asn Gly Ala Val Thr Ser Tyr Ile Asn Thr Ile Val Asn Ser Lys
        115                 120                 125

Ser Ile Thr Glu Ala Ile Ser Arg Val Ala Ala Met Ser Glu Ile Val
130                 135                 140

Ser Ala Asn Asn Lys Met Leu Glu Gln Gln Lys Ala Asp Lys Lys Ala
145                 150                 155                 160

Ile Ser Glu Lys Gln Val Ala Asn Asn Asp Ala Ile Asn Thr Val Ile
                165                 170                 175

Ala Asn Gln Gln Lys Leu Ala Asp Asp Ala Gln Ala Leu Thr Thr Lys
            180                 185                 190

Gln Ala Glu Leu Lys Ala Ala Glu Leu Ser Leu Ala Ala Glu Lys Ala
        195                 200                 205

Thr Ala Glu Gly Glu Lys Ala Ser Leu Leu Glu Gln Lys Ala Ala
    210                 215                 220

Glu Ala Glu Ala Arg Ala Ala Ala Val Ala Glu Ala Ala Tyr Lys Glu
225                 230                 235                 240
```

Lys Arg Ala Ser Gln Gln Ser Val Leu Ala Ser Ala Asn Thr Asn
                245                 250                 255

Leu Thr Ala Gln Val Gln Ala Val Ser Glu Ser Ala Ala Pro Val
            260                 265                 270

Arg Ala Lys Val Arg Pro Thr Tyr Ser Thr Asn Ala Ser Ser Tyr Pro
        275                 280                 285

Ile Gly Glu Cys Thr Trp Gly Val Lys Thr Leu Ala Pro Trp Ala Gly
        290                 295                 300

Asp Tyr Trp Gly Asn Gly Ala Gln Trp Ala Thr Ser Ala Ala Ala Ala
305                 310                 315                 320

Gly Phe Arg Thr Gly Ser Thr Pro Gln Val Gly Ala Ile Ala Cys Trp
            325                 330                 335

Asn Asp Gly Gly Tyr Gly His Val Ala Val Thr Ala Val Glu Ser
            340                 345                 350

Thr Thr Arg Ile Gln Val Ser Glu Ser Asn Tyr Ala Gly Asn Arg Thr
            355                 360                 365

Ile Gly Asn His Arg Gly Trp Phe Asn Pro Thr Thr Thr Ser Glu Gly
        370                 375                 380

Phe Val Thr Tyr Ile Tyr Ala Asp
385                 390

<210> SEQ ID NO 4
<211> LENGTH: 366
<212> TYPE: PRT
<213> ORGANISM: Streptococcus pneumoniae

<400> SEQUENCE: 4

Ala Glu Thr Thr Asp Asp Lys Ile Ala Ala Gln Asp Asn Lys Ile Ser
1               5                   10                  15

Asn Leu Thr Ala Gln Gln Glu Ala Gln Lys Gln Val Asp Gln Ile
            20                  25                  30

Gln Glu Gln Val Ser Ala Ile Gln Ala Glu Gln Ser Asn Leu Gln Ala
            35                  40                  45

Glu Asn Asp Arg Leu Gln Ala Glu Ser Lys Lys Leu Glu Gly Glu Ile
50                  55                  60

Thr Glu Leu Ser Lys Asn Ile Val Ser Arg Asn Gln Ser Leu Glu Lys
65                  70                  75                  80

Gln Ala Arg Ser Ala Gln Thr Asn Gly Ala Val Thr Ser Tyr Ile Asn
                85                  90                  95

Thr Ile Val Asn Ser Lys Ser Ile Thr Glu Ala Ile Ser Arg Val Ala
            100                 105                 110

Ala Met Ser Glu Ile Val Ser Ala Asn Asn Lys Met Leu Glu Gln Gln
        115                 120                 125

Lys Ala Asp Lys Lys Ala Ile Ser Glu Lys Gln Val Ala Asn Asn Asp
130                 135                 140

Ala Ile Asn Thr Val Ile Ala Asn Gln Gln Lys Leu Ala Asp Asp Ala
145                 150                 155                 160

Gln Ala Leu Thr Thr Lys Gln Ala Glu Leu Lys Ala Ala Glu Leu Ser
                165                 170                 175

Leu Ala Ala Glu Lys Ala Thr Ala Gly Glu Lys Ala Ser Leu Leu
            180                 185                 190

Glu Gln Lys Ala Ala Ala Glu Ala Glu Ala Arg Ala Ala Ala Val Ala
        195                 200                 205

Glu Ala Ala Tyr Lys Glu Lys Arg Ala Ser Gln Gln Gln Ser Val Leu

```
                210                 215                 220
Ala Ser Ala Asn Thr Asn Leu Thr Ala Gln Val Gln Ala Val Ser Glu
225                 230                 235                 240

Ser Ala Ala Ala Pro Val Arg Ala Lys Val Arg Pro Thr Tyr Ser Thr
                245                 250                 255

Asn Ala Ser Ser Tyr Pro Ile Gly Glu Cys Thr Trp Gly Val Lys Thr
                260                 265                 270

Leu Ala Pro Trp Ala Gly Asp Tyr Trp Gly Asn Gly Ala Gln Trp Ala
            275                 280                 285

Thr Ser Ala Ala Ala Gly Phe Arg Thr Gly Ser Thr Pro Gln Val
        290                 295                 300

Gly Ala Ile Ala Cys Trp Asn Asp Gly Gly Tyr Gly His Val Ala Val
305                 310                 315                 320

Val Thr Ala Val Glu Ser Thr Thr Arg Ile Gln Val Ser Glu Ser Asn
                325                 330                 335

Tyr Ala Gly Asn Arg Thr Ile Gly Asn His Arg Gly Trp Phe Asn Pro
                340                 345                 350

Thr Thr Thr Ser Glu Gly Phe Val Thr Tyr Ile Tyr Ala Asp
            355                 360                 365

<210> SEQ ID NO 5
<211> LENGTH: 6
<212> TYPE: PRT
<213> ORGANISM: Artificial Sequence
<220> FEATURE:
<223> OTHER INFORMATION: synthetic linker

<400> SEQUENCE: 5

Gly Ser Gly Gly Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic linker

<400> SEQUENCE: 6

Gly Ser Gly Ser Gly Gly Gly Gly
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic linker

<400> SEQUENCE: 7

Ala Ala Ala Leu Glu
1               5

<210> SEQ ID NO 8
<211> LENGTH: 6
<212> TYPE: PRT
<213> ORGANISM: Artificial Sequence
<220> FEATURE:
<223> OTHER INFORMATION: synthetic histidine tag

<400> SEQUENCE: 8

His His His His His His
```

<210> SEQ ID NO 9
<211> LENGTH: 555
<212> TYPE: PRT
<213> ORGANISM: Streptococcus pneumoniae

<400> SEQUENCE: 9

```
Met Val Ser Ala Gln Glu Ser Ser Thr Tyr Thr Val Lys Glu Gly Asp
1               5                   10                  15

Thr Leu Ser Glu Ile Ala Glu Thr His Asn Thr Thr Val Glu Lys Leu
            20                  25                  30

Ala Glu Asn Asn His Ile Asp Asn Ile His Leu Ile Tyr Val Asp Gln
        35                  40                  45

Glu Leu Val Ile Asp Gly Pro Val Ala Pro Val Ala Thr Pro Ala Pro
    50                  55                  60

Ala Thr Tyr Ala Ala Pro Ala Ala Gln Asp Glu Thr Val Ser Ala Pro
65                  70                  75                  80

Val Ala Glu Thr Pro Val Val Ser Glu Thr Val Val Ser Thr Val Ser
                85                  90                  95

Gly Ser Glu Ala Glu Ala Lys Glu Trp Ile Ala Gln Lys Glu Ser Gly
            100                 105                 110

Gly Ser Tyr Thr Ala Thr Asn Gly Arg Tyr Ile Gly Arg Tyr Gln Leu
        115                 120                 125

Thr Asp Ser Tyr Leu Asn Gly Asp Tyr Ser Ala Glu Asn Gln Glu Arg
    130                 135                 140

Val Ala Asp Ala Tyr Val Ala Gly Arg Tyr Gly Ser Trp Thr Ala Ala
145                 150                 155                 160

Lys Asn Phe Trp Leu Asn Asn Gly Trp Tyr Gly Ser Gly Ser Gly Gly
                165                 170                 175

Gly Gly Ala Glu Thr Thr Asp Asp Lys Ile Ala Ala Gln Asp Asn Lys
            180                 185                 190

Ile Ser Asn Leu Thr Ala Gln Gln Gln Glu Ala Gln Lys Gln Val Asp
        195                 200                 205

Gln Ile Gln Glu Gln Val Ser Ala Ile Gln Ala Glu Gln Ser Asn Leu
    210                 215                 220

Gln Ala Glu Asn Asp Arg Leu Gln Ala Glu Ser Lys Lys Leu Glu Gly
225                 230                 235                 240

Glu Ile Thr Glu Leu Ser Lys Asn Ile Val Ser Arg Asn Gln Ser Leu
                245                 250                 255

Glu Lys Gln Ala Arg Ser Ala Gln Thr Asn Gly Ala Val Thr Ser Tyr
            260                 265                 270

Ile Asn Thr Ile Val Asn Ser Lys Ser Ile Thr Glu Ala Ile Ser Arg
        275                 280                 285

Val Ala Ala Met Ser Glu Ile Val Ser Ala Asn Asn Lys Met Leu Glu
    290                 295                 300

Gln Gln Lys Ala Asp Lys Lys Ala Ile Ser Glu Lys Gln Val Ala Asn
305                 310                 315                 320

Asn Asp Ala Ile Asn Thr Val Ile Ala Asn Gln Gln Lys Leu Ala Asp
                325                 330                 335

Asp Ala Gln Ala Leu Thr Thr Lys Gln Ala Glu Leu Lys Ala Ala Glu
            340                 345                 350

Leu Ser Leu Ala Ala Glu Lys Ala Thr Ala Glu Gly Glu Lys Ala Ser
        355                 360                 365
```

```
Leu Leu Glu Gln Lys Ala Ala Glu Ala Glu Ala Arg Ala Ala Ala
    370             375             380

Val Ala Glu Ala Ala Tyr Lys Glu Lys Arg Ala Ser Gln Gln Ser
385             390             395             400

Val Leu Ala Ser Ala Asn Thr Asn Leu Thr Ala Gln Val Gln Ala Val
                405             410             415

Ser Glu Ser Ala Ala Ala Pro Val Arg Ala Lys Val Arg Pro Thr Tyr
                420             425             430

Ser Thr Asn Ala Ser Ser Tyr Pro Ile Gly Glu Cys Thr Trp Gly Val
                435             440             445

Lys Thr Leu Ala Pro Trp Ala Gly Asp Tyr Trp Gly Asn Gly Ala Gln
450             455             460

Trp Ala Thr Ser Ala Ala Ala Gly Phe Arg Thr Gly Ser Thr Pro
465             470             475             480

Gln Val Gly Ala Ile Ala Cys Trp Asn Asp Gly Gly Tyr Gly His Val
                485             490             495

Ala Val Val Thr Ala Val Glu Ser Thr Thr Arg Ile Gln Val Ser Glu
                500             505             510

Ser Asn Tyr Ala Gly Asn Arg Thr Ile Gly Asn His Arg Gly Trp Phe
                515             520             525

Asn Pro Thr Thr Thr Ser Glu Gly Phe Val Thr Tyr Ile Tyr Ala Asp
                530             535             540

Ala Ala Leu Glu His His His His His
545             550             555

<210> SEQ ID NO 10
<211> LENGTH: 552
<212> TYPE: PRT
<213> ORGANISM: Streptococcus pneumoniae

<400> SEQUENCE: 10

Met Ala Glu Thr Thr Asp Asp Lys Ile Ala Ala Gln Asp Asn Lys Ile
1               5               10              15

Ser Asn Leu Thr Ala Gln Gln Glu Ala Gln Lys Gln Val Asp Gln
            20              25              30

Ile Gln Glu Gln Val Ser Ala Ile Gln Ala Glu Gln Ser Asn Leu Gln
            35              40              45

Ala Glu Asn Asp Arg Leu Gln Ala Glu Ser Lys Lys Leu Glu Gly Glu
        50              55              60

Ile Thr Glu Leu Ser Lys Asn Ile Val Ser Arg Asn Gln Ser Leu Glu
65              70              75              80

Lys Gln Ala Arg Ser Ala Gln Thr Asn Gly Ala Val Thr Ser Tyr Ile
            85              90              95

Asn Thr Ile Val Asn Ser Lys Ser Ile Thr Glu Ala Ile Ser Arg Val
            100             105             110

Ala Ala Met Ser Glu Ile Val Ser Ala Asn Asn Lys Met Leu Glu Gln
            115             120             125

Gln Lys Ala Asp Lys Lys Ala Ile Ser Glu Lys Gln Val Ala Asn Asn
        130             135             140

Asp Ala Ile Asn Thr Val Ile Ala Asn Gln Gln Lys Leu Ala Asp Asp
145             150             155             160

Ala Gln Ala Leu Thr Thr Lys Gln Ala Glu Leu Lys Ala Ala Glu Leu
            165             170             175

Ser Leu Ala Ala Glu Lys Ala Thr Ala Glu Gly Glu Lys Ala Ser Leu
            180             185             190
```

```
Leu Glu Gln Lys Ala Ala Ala Glu Ala Glu Ala Arg Ala Ala Ala Val
            195                 200                 205

Ala Glu Ala Ala Tyr Lys Glu Lys Arg Ala Ser Gln Gln Gln Ser Val
        210                 215                 220

Leu Ala Ser Ala Asn Thr Asn Leu Thr Ala Gln Val Gln Ala Val Ser
225                 230                 235                 240

Glu Ser Ala Ala Ala Pro Val Arg Ala Lys Val Arg Pro Thr Tyr Ser
                245                 250                 255

Thr Asn Ala Ser Ser Tyr Pro Ile Gly Glu Cys Thr Trp Gly Val Lys
                260                 265                 270

Thr Leu Ala Pro Trp Ala Gly Asp Tyr Trp Gly Asn Gly Ala Gln Trp
            275                 280                 285

Ala Thr Ser Ala Ala Ala Ala Gly Phe Arg Thr Gly Ser Thr Pro Gln
            290                 295                 300

Val Gly Ala Ile Ala Cys Trp Asn Asp Gly Gly Tyr Gly His Val Ala
305                 310                 315                 320

Val Val Thr Ala Val Glu Ser Thr Thr Arg Ile Gln Val Ser Glu Ser
                325                 330                 335

Asn Tyr Ala Gly Asn Arg Thr Ile Gly Asn His Arg Gly Trp Phe Asn
            340                 345                 350

Pro Thr Thr Thr Ser Glu Gly Phe Val Thr Tyr Ile Tyr Ala Asp Gly
            355                 360                 365

Ser Gly Ser Gly Gly Gly Val Ser Ala Gln Glu Ser Ser Thr Tyr
        370                 375                 380

Thr Val Lys Glu Gly Asp Thr Leu Ser Glu Ile Ala Glu Thr His Asn
385                 390                 395                 400

Thr Thr Val Glu Lys Leu Ala Glu Asn Asn His Ile Asp Asn Ile His
                405                 410                 415

Leu Ile Tyr Val Asp Gln Glu Leu Val Ile Asp Gly Pro Val Ala Pro
            420                 425                 430

Val Ala Thr Pro Ala Pro Ala Thr Tyr Ala Ala Pro Ala Ala Gln Asp
            435                 440                 445

Glu Thr Val Ser Ala Pro Val Ala Glu Thr Pro Val Val Ser Glu Thr
            450                 455                 460

Val Val Ser Thr Val Ser Gly Ser Glu Ala Glu Ala Lys Glu Trp Ile
465                 470                 475                 480

Ala Gln Lys Glu Ser Gly Gly Ser Tyr Thr Ala Thr Asn Gly Arg Tyr
                485                 490                 495

Ile Gly Arg Tyr Gln Leu Thr Asp Ser Tyr Leu Asn Gly Asp Tyr Ser
            500                 505                 510

Ala Glu Asn Gln Glu Arg Val Ala Asp Ala Tyr Val Ala Gly Arg Tyr
            515                 520                 525

Gly Ser Trp Thr Ala Ala Lys Asn Phe Trp Leu Asn Asn Gly Trp Tyr
        530                 535                 540

Leu Glu His His His His His His
545                 550
```